(12) United States Patent
Manwaring et al.

(10) Patent No.: US 10,149,712 B2
(45) Date of Patent: *Dec. 11, 2018

(54) LAYERED FERROMAGNETIC COATED CONDUCTOR THERMAL SURGICAL TOOL

(71) Applicant: Domain Surgical, Inc., Salt Lake City, UT (US)

(72) Inventors: Kim Manwaring, Phoenix, AZ (US); Philip Eggers, Salt Lake City, UT (US); Mark Stringham, Kearns, UT (US); Paul Hammond, Salt Lake City, UT (US); David J. McNally, Salt Lake City, UT (US)

(73) Assignee: Domain Surgical, Inc., Salt Lake City, UT (US)

( * ) Notice: Subject to any disclaimer, the term of this patent is extended or adjusted under 35 U.S.C. 154(b) by 583 days.

This patent is subject to a terminal disclaimer.

(21) Appl. No.: 14/804,343

(22) Filed: Jul. 21, 2015

(65) Prior Publication Data

US 2016/0030103 A1 Feb. 4, 2016

Related U.S. Application Data

(60) Division of application No. 13/441,614, filed on Apr. 6, 2012, now Pat. No. 9,131,977, which is a
(Continued)

(51) Int. Cl.
*A61B 18/04* (2006.01)
*A61B 18/08* (2006.01)
(Continued)

(52) U.S. Cl.
CPC ............ *A61B 18/082* (2013.01); *A61B 18/10* (2013.01); *C23C 28/02* (2013.01); *A61B 18/1442* (2013.01);
(Continued)

(58) Field of Classification Search
CPC .............. A61B 1/07; A61B 17/320068; A61B 17/320072; A61B 17/320084;
(Continued)

(56) References Cited

U.S. PATENT DOCUMENTS

| 300,155 A | 6/1884 | Starr |
| 770,368 A | 9/1904 | Heath |

(Continued)

FOREIGN PATENT DOCUMENTS

| EP | 0033958 | 8/1981 |
| EP | 0 130 671 | 9/1985 |

(Continued)

OTHER PUBLICATIONS

Center for Research in Scientific Computation. *A Domain Wall Theory for Ferroelectric Hysteresis*, Jan. 1999.

(Continued)

*Primary Examiner* — Jaymi Della
(74) *Attorney, Agent, or Firm* — Seed Intellectual Property Law Group LLP

(57) ABSTRACT

A thermal surgical tool comprising a conductor having a ferromagnetic material attached thereto is provided. The conductor may include a support of sufficiently high Young's modulus to resist bending when the surgical tool is being used to treat tissue. One or more intervening layers may be disposed between the support and the ferromagnetic material. Each of the intervening layers may be selected for a property that facilitates construction of the surgical tool and/or enhances a functionality of the surgical tool. The thermal surgical tool can be used for separating tissue, coagulation, tissue destruction or achieving other desired tissue effects in numerous surgical procedures.

18 Claims, 34 Drawing Sheets

Related U.S. Application Data continuation-in-part of application No. 12/647,344, filed on Dec. 24, 2009, now Pat. No. 8,377,052.

(60) Provisional application No. 61/170,203, filed on Apr. 17, 2009, provisional application No. 61/170,220, filed on Apr. 17, 2009, provisional application No. 61/170,207, filed on Apr. 17, 2009, provisional application No. 61/473,729, filed on Apr. 8, 2011.

(51) Int. Cl.
| | | |
|---|---|---|
| *A61B 18/10* | (2006.01) | |
| *C23C 28/02* | (2006.01) | |
| *A61B 18/00* | (2006.01) | |
| *A61B 18/14* | (2006.01) | |
| *A61B 17/00* | (2006.01) | |

(52) U.S. Cl.
CPC .............. *A61B 2017/00526* (2013.01); *A61B 2018/00107* (2013.01); *A61B 2018/00148* (2013.01); *A61B 2018/00601* (2013.01); *A61B 2018/00642* (2013.01); *A61B 2018/1407* (2013.01); *A61B 2018/1412* (2013.01); *A61B 2018/1417* (2013.01)

(58) Field of Classification Search
CPC ............ A61B 17/320092; A61B 18/04; A61B 18/18; A61B 2002/2864; A61B 2018/00089; A61B 2018/00095; A61B 2018/00214; A61B 2018/0022; A61B 2018/00601; A61B 2018/00876; A61B 2018/046; A61B 2018/00107; A61F 2002/2864; A61F 2002/4651; A61F 7/123; A61F 9/0079; A61M 2205/368; A61M 2205/3693; A61N 1/40; A61N 1/403; A61N 2/02
See application file for complete search history.

(56) References Cited

U.S. PATENT DOCUMENTS

| | | | |
|---|---|---|---|
| 1,104,053 A | 7/1914 | Lea | |
| 1,280,052 A | 9/1918 | Lidberg | |
| 1,335,987 A | 4/1920 | Reid | |
| 1,366,231 A | 1/1921 | Winter et al. | |
| 1,401,104 A | 12/1921 | Kruesheld | |
| 1,794,296 A | 2/1931 | Hyams | |
| 2,027,854 A | 1/1936 | Breth et al. | |
| 2,050,904 A | 8/1936 | Trice | |
| 2,120,598 A | 6/1938 | Beuoy | |
| 2,250,602 A | 7/1941 | Pierce | |
| 2,278,633 A | 4/1942 | Bagnall | |
| 2,375,154 A | 5/1945 | Volterra | |
| 2,412,977 A | 12/1946 | Eskin | |
| 2,501,499 A | 3/1950 | Crowley | |
| 2,670,425 A | 12/1954 | Stone | |
| 2,735,797 A | 2/1956 | Schjeldahl | |
| 2,782,290 A | 2/1957 | Lannan et al. | |
| 2,831,242 A | 4/1958 | Kieffer et al. | |
| 2,846,560 A | 8/1958 | Jacoby et al. | |
| 2,863,036 A | 12/1958 | Mitchell et al. | |
| 2,947,345 A | 8/1960 | Schjeldahl | |
| 2,960,592 A | 11/1960 | Pierce | |
| 3,084,242 A | 4/1963 | Vogler et al. | |
| 3,213,259 A | 10/1965 | Bennet et al. | |
| 3,350,544 A | 10/1967 | Lennox | |
| 3,352,011 A | 11/1967 | Alexander et al. | |
| 3,400,252 A | 9/1968 | Hayakawa | |
| 3,404,202 A | 10/1968 | Carlson et al. | |
| 3,413,442 A | 11/1968 | Buiting et al. | |
| 3,414,705 A | 12/1968 | Marcoux | |
| 3,434,476 A | 3/1969 | Shaw et al. | |
| 3,501,619 A | 3/1970 | Buiting et al. | |
| 3,515,837 A | 6/1970 | Ando | |
| 3,520,043 A | 7/1970 | Darling | |
| 3,556,953 A | 1/1971 | Schulz | |
| 3,768,482 A | 10/1973 | Shaw | |
| 3,825,004 A | 7/1974 | Durden, III | |
| 3,826,263 A | 7/1974 | Cage et al. | |
| 3,834,392 A | 9/1974 | Lampman et al. | |
| 3,978,312 A | 8/1976 | Barton et al. | |
| RE29,088 E | 12/1976 | Shaw | |
| 4,089,336 A | 5/1978 | Cage et al. | |
| 4,091,813 A | 5/1978 | Shaw et al. | |
| RE30,190 E | 1/1980 | Shaw | |
| 4,185,632 A | 1/1980 | Shaw | |
| 4,196,734 A | 4/1980 | Harris | |
| 4,198,957 A | 4/1980 | Cage et al. | |
| 4,206,759 A | 6/1980 | Shaw | |
| 4,207,896 A | 6/1980 | Shaw | |
| 4,209,017 A | 6/1980 | Shaw | |
| 4,256,945 A | 3/1981 | Carter et al. | |
| 4,359,052 A | 11/1982 | Staub | |
| 4,364,390 A | 12/1982 | Shaw | |
| 4,371,861 A | 2/1983 | Abdelrahman et al. | |
| 4,374,517 A | 2/1983 | Hagiwara | |
| RE31,723 E | 11/1984 | Shaw | |
| 4,481,057 A | 11/1984 | Beard | |
| 4,485,810 A | 12/1984 | Beard | |
| 4,492,231 A | 1/1985 | Auth | |
| 4,493,320 A | 1/1985 | Treat | |
| 4,523,084 A | 6/1985 | Tamura et al. | |
| 4,549,073 A | 10/1985 | Tamura et al. | |
| 4,600,018 A | 7/1986 | James et al. | |
| 4,622,966 A | 11/1986 | Beard | |
| 4,658,819 A | 4/1987 | Harris et al. | |
| 4,658,820 A | 4/1987 | Klicek | |
| 4,701,587 A | 10/1987 | Carter et al. | |
| 4,752,673 A | 6/1988 | Krumme | |
| 4,807,620 A | 2/1989 | Strul | |
| 4,839,501 A | 6/1989 | Cowell | |
| 4,848,337 A | 7/1989 | Shaw et al. | |
| 4,860,745 A | 8/1989 | Farin et al. | |
| 4,877,944 A | 10/1989 | Cowell et al. | |
| 4,914,267 A | 4/1990 | Derbyshire | |
| 4,915,100 A | 4/1990 | Green | |
| 4,927,413 A | 5/1990 | Hess | |
| 4,938,761 A | 7/1990 | Ensslin | |
| 5,003,991 A | 4/1991 | Takayama et al. | |
| 5,047,025 A | 9/1991 | Taylor et al. | |
| 5,053,595 A | 10/1991 | Derbyshire | |
| 5,057,106 A | 10/1991 | Kasevich et al. | |
| 5,071,419 A | 12/1991 | Rydell et al. | |
| 5,087,256 A | 2/1992 | Taylor et al. | |
| 5,087,804 A | 2/1992 | McGaffigan | |
| 5,098,429 A | 3/1992 | Sterzer | |
| 5,107,095 A | 4/1992 | Derbyshire | |
| 5,182,427 A | 1/1993 | McGaffigan | |
| 5,189,271 A | 2/1993 | Derbyshire | |
| 5,197,649 A | 3/1993 | Bessler et al. | |
| 5,203,782 A | 4/1993 | Gudov et al. | |
| 5,209,725 A | 5/1993 | Roth | |
| 5,211,646 A | 5/1993 | Alperovich et al. | |
| 5,217,460 A | 9/1993 | Knoepfler | |
| 5,300,068 A | 4/1994 | Rosar et al. | |
| 5,300,750 A | 4/1994 | Carter, Jr. et al. | |
| 5,308,311 A | 5/1994 | Eggers et al. | |
| 5,318,564 A | 6/1994 | Eggers | |
| 5,364,392 A | 11/1994 | Warner et al. | |
| 5,370,645 A | 12/1994 | Klicek et al. | |
| 5,370,675 A | 12/1994 | Edwards et al. | |
| 5,376,094 A | 12/1994 | Kline | |
| 5,382,247 A | 1/1995 | Cimino et al. | |
| 5,400,267 A | 3/1995 | Denen et al. | |
| 5,411,508 A | 5/1995 | Bessler et al. | |
| 5,423,808 A | 6/1995 | Edwards et al. | |
| 5,425,731 A | 6/1995 | Daniel et al. | |
| 5,445,635 A | 8/1995 | Denen et al. | |
| 5,472,443 A | 12/1995 | Cordis et al. | |
| 5,475,203 A | 12/1995 | McGaffigan | |
| 5,480,397 A | 1/1996 | Eggers | |

(56) References Cited

U.S. PATENT DOCUMENTS

| | | |
|---|---|---|
| 5,480,398 A | 1/1996 | Eggers |
| 5,496,312 A | 3/1996 | Klicek |
| 5,496,314 A | 3/1996 | Eggers |
| 5,507,743 A | 4/1996 | Edwards et al. |
| 5,540,679 A | 7/1996 | Fram et al. |
| 5,540,681 A | 7/1996 | Strul et al. |
| 5,542,916 A | 8/1996 | Hirsch et al. |
| 5,571,153 A | 11/1996 | Wallsten |
| 5,573,533 A | 11/1996 | Strul |
| 5,593,406 A | 1/1997 | Eggers et al. |
| 5,595,565 A | 1/1997 | Treat et al. |
| 5,611,798 A | 3/1997 | Eggers |
| 5,628,771 A | 5/1997 | Mizukawa et al. |
| 5,674,219 A | 10/1997 | Monson et al. |
| 5,707,369 A | 1/1998 | Vaitekunas et al. |
| 5,707,402 A | 1/1998 | Heim |
| 5,807,392 A | 9/1998 | Eggers |
| 5,807,393 A | 9/1998 | Williamson, IV et al. |
| 5,827,269 A | 10/1998 | Saadat |
| 5,836,874 A | 11/1998 | Swanson et al. |
| 5,836,943 A | 11/1998 | Miller, III |
| 5,843,019 A | 12/1998 | Eggers et al. |
| 5,855,061 A | 1/1999 | Malis et al. |
| 5,911,719 A | 6/1999 | Eggers |
| 5,951,546 A | 9/1999 | Lorentzen |
| 5,964,759 A | 10/1999 | Yamanashi et al. |
| 6,004,316 A | 12/1999 | Laufer |
| 6,006,755 A | 12/1999 | Edwards |
| 6,015,415 A | 1/2000 | Avellanet |
| 6,035,238 A | 3/2000 | Ingle et al. |
| 6,038,017 A | 3/2000 | Pinsukanjana et al. |
| 6,039,733 A | 3/2000 | Buysse et al. |
| 6,066,138 A | 5/2000 | Sheffer et al. |
| 6,161,048 A | 12/2000 | Sluijter et al. |
| 6,190,382 B1 | 2/2001 | Ormsby et al. |
| 6,210,403 B1 | 4/2001 | Klicek |
| 6,228,084 B1 | 5/2001 | Kirwan, Jr. |
| 6,241,723 B1 | 6/2001 | Heim et al. |
| 6,287,305 B1 | 9/2001 | Heim et al. |
| 6,290,697 B1 | 9/2001 | Tu et al. |
| 6,350,262 B1 | 2/2002 | Ashley |
| 6,358,273 B1 | 3/2002 | Strul et al. |
| 6,454,781 B1 | 9/2002 | Witt et al. |
| 6,533,781 B2 | 3/2003 | Heim et al. |
| 6,602,252 B2 | 8/2003 | Mollenauer |
| 6,604,003 B2 | 8/2003 | Fredricks et al. |
| 6,626,901 B1 | 9/2003 | Treat et al. |
| 6,632,182 B1 | 10/2003 | Treat |
| 6,692,489 B1 | 2/2004 | Heim et al. |
| 6,723,094 B1 | 4/2004 | Desinger |
| 6,726,683 B1 | 4/2004 | Shaw |
| 6,821,273 B2 | 11/2004 | Mollenauer |
| 6,860,880 B2 | 3/2005 | Treat et al. |
| 6,908,463 B2 | 6/2005 | Treat et al. |
| 6,911,026 B1 | 6/2005 | Hall et al. |
| 6,912,911 B2 | 7/2005 | Oh et al. |
| 6,980,862 B2 | 12/2005 | Fredricks et al. |
| 6,980,865 B1 | 12/2005 | Wang et al. |
| 7,011,656 B2 | 3/2006 | McGaffigan |
| 7,025,065 B2 | 4/2006 | McGaffigan et al. |
| 7,083,613 B2 | 8/2006 | Treat |
| 7,112,201 B2 | 9/2006 | Truckai et al. |
| 7,122,030 B2 | 10/2006 | Flores et al. |
| 7,164,968 B2 | 1/2007 | Treat et al. |
| 7,175,621 B2 | 2/2007 | Heim et al. |
| 7,211,079 B2 | 5/2007 | Treat |
| 7,211,080 B2 | 5/2007 | Treat et al. |
| 7,235,073 B2 | 6/2007 | Levine et al. |
| 7,300,452 B2 | 11/2007 | Gleich |
| 7,317,275 B2 | 1/2008 | Treat |
| 7,326,202 B2 | 2/2008 | McGaffigan |
| 7,329,255 B2 | 2/2008 | McGaffigan |
| 7,377,919 B2 | 5/2008 | Heim et al. |
| 7,396,356 B2 | 7/2008 | Mollenauer |
| 7,435,249 B2 | 10/2008 | Buysse et al. |
| 7,473,250 B2 | 1/2009 | Makin et al. |
| 7,473,253 B2 | 1/2009 | Dycus et al. |
| 7,494,492 B2 | 2/2009 | Da Silva et al. |
| 7,528,663 B2 | 5/2009 | Naletov et al. |
| 7,533,719 B2 | 5/2009 | Hinson |
| 7,540,324 B2 | 6/2009 | de Rouffignac |
| 7,549,470 B2 | 6/2009 | Vinegar |
| 7,553,309 B2 | 6/2009 | Buysse et al. |
| 7,556,095 B2 | 7/2009 | Vinegar |
| 7,556,096 B2 | 7/2009 | Vinegar |
| 7,559,367 B2 | 7/2009 | Vinegar |
| 7,559,368 B2 | 7/2009 | Vinegar |
| 7,562,706 B2 | 7/2009 | Li et al. |
| 7,562,707 B2 | 7/2009 | Miller |
| 7,578,815 B2 | 8/2009 | Howell |
| 7,581,589 B2 | 9/2009 | Roes et al. |
| 7,584,789 B2 | 9/2009 | Mo et al. |
| 7,588,565 B2 | 9/2009 | Marchitto et al. |
| 7,588,566 B2 | 9/2009 | Treat et al. |
| 7,591,310 B2 | 9/2009 | Minderhoud |
| 7,597,147 B2 | 10/2009 | Vitek |
| 7,604,052 B2 | 10/2009 | Roes |
| 7,610,962 B2 | 11/2009 | Fowler |
| 7,613,523 B2 | 11/2009 | Eggers et al. |
| 7,631,689 B2 | 12/2009 | Vinegar |
| 7,631,690 B2 | 12/2009 | Vinegar |
| 7,632,295 B2 | 12/2009 | Flores |
| 7,635,023 B2 | 12/2009 | Goldberg |
| 7,635,024 B2 | 12/2009 | Karanikas |
| 7,635,025 B2 | 12/2009 | Vinegar |
| 7,678,105 B2 | 3/2010 | McGreevy et al. |
| 7,699,842 B2 | 4/2010 | Buysse et al. |
| 7,702,397 B2 | 4/2010 | Fredricks et al. |
| 7,776,035 B2 | 8/2010 | Rick et al. |
| 7,828,798 B2 | 11/2010 | Buysse et al. |
| 7,871,406 B2 | 1/2011 | Nields et al. |
| 7,879,033 B2 | 2/2011 | Sartor et al. |
| 7,887,535 B2 | 2/2011 | Lands et al. |
| 7,922,713 B2 | 4/2011 | Geisel |
| 7,931,649 B2 | 4/2011 | Couture et al. |
| 7,938,779 B2 | 5/2011 | Sakurai et al. |
| 7,951,149 B2 | 5/2011 | Carlton |
| 7,951,150 B2 | 5/2011 | Johnson et al. |
| 7,959,633 B2 | 6/2011 | Sartor et al. |
| 7,963,965 B2 | 6/2011 | Buysse et al. |
| 7,972,334 B2 | 7/2011 | McGreevy et al. |
| 7,972,335 B2 | 7/2011 | McGreevy et al. |
| 7,981,113 B2 | 7/2011 | Truckai et al. |
| 8,062,290 B2 | 11/2011 | Buysse et al. |
| 8,100,896 B2 | 1/2012 | Rodhajsky |
| 8,100,908 B2 | 1/2012 | McGaffigan et al. |
| 8,104,956 B2 | 1/2012 | Blaha |
| 8,105,323 B2 | 1/2012 | Buysse et al. |
| 8,211,105 B2 | 7/2012 | Buysse et al. |
| 8,241,284 B2 | 8/2012 | Dycus et al. |
| 8,287,528 B2 | 10/2012 | Wham et al. |
| 8,292,879 B2 | 10/2012 | Manwaring et al. |
| 8,372,066 B2 | 2/2013 | Marwaring et al. |
| 8,377,052 B2 | 2/2013 | Manwaring et al. |
| 8,377,057 B2 | 2/2013 | Rick et al. |
| 8,414,569 B2 | 4/2013 | Manwaring et al. |
| 8,419,724 B2 | 4/2013 | Manwaring et al. |
| 8,425,503 B2 | 4/2013 | Manwaring et al. |
| 8,430,870 B2 | 4/2013 | Manwaring et al. |
| 8,460,870 B2 | 6/2013 | Zocchi |
| 8,480,666 B2 | 7/2013 | Buysse et al. |
| 8,491,578 B2 | 7/2013 | Manwaring et al. |
| 8,506,561 B2 | 8/2013 | Manwaring et al. |
| 8,523,850 B2 | 9/2013 | Manwaring et al. |
| 8,523,851 B2 | 9/2013 | Manwaring et al. |
| 8,568,402 B2 | 10/2013 | Buysse et al. |
| 8,617,151 B2 | 12/2013 | Dennis et al. |
| 8,667,674 B2 | 3/2014 | Buysse |
| 8,672,938 B2 | 3/2014 | Buysse et al. |
| 8,932,279 B2 | 1/2015 | Stringham et al. |
| 9,078,655 B2 | 7/2015 | Manwaring et al. |
| 9,107,666 B2 | 8/2015 | Manwaring et al. |
| 9,220,557 B2 | 12/2015 | Manwaring et al. |
| 9,265,553 B2 | 2/2016 | Manwaring et al. |

(56) References Cited

U.S. PATENT DOCUMENTS

| | | |
|---|---|---|
| 9,265,554 B2 | 2/2016 | Manwaring et al. |
| 9,265,555 B2 | 2/2016 | Manwaring et al. |
| 9,265,556 B2 | 2/2016 | Manwaring et al. |
| 2001/0014804 A1 | 8/2001 | Goble et al. |
| 2002/0016591 A1 | 2/2002 | Levine |
| 2002/0019627 A1 | 2/2002 | Maguire et al. |
| 2002/0019644 A1 | 2/2002 | Hastings et al. |
| 2002/0026188 A1 | 2/2002 | Balbierz et al. |
| 2002/0029037 A1 | 3/2002 | Kim |
| 2002/0029062 A1 | 3/2002 | Satake |
| 2002/0068931 A1 | 6/2002 | Wong et al. |
| 2002/0087156 A1 | 7/2002 | Maguire et al. |
| 2002/0120261 A1 | 8/2002 | Balbierz et al. |
| 2002/0133148 A1 | 9/2002 | Daniel et al. |
| 2002/0165529 A1 | 11/2002 | Danek |
| 2002/0173787 A1 | 11/2002 | Buysse et al. |
| 2003/0004507 A1 | 1/2003 | Francischelli et al. |
| 2003/0055417 A1 | 3/2003 | Truckai et al. |
| 2003/0055424 A1 | 3/2003 | Ciarrocca |
| 2003/0060818 A1 | 3/2003 | Kannenberg et al. |
| 2003/0073987 A1 | 4/2003 | Sakurai et al. |
| 2003/0073989 A1 | 4/2003 | Hoey et al. |
| 2003/0109871 A1 | 6/2003 | Johnson et al. |
| 2003/0139741 A1 | 7/2003 | Goble et al. |
| 2003/0144660 A1 | 7/2003 | Mollenauer |
| 2003/0171747 A1 | 9/2003 | Kanehira et al. |
| 2003/0176873 A1 | 9/2003 | Chernenko et al. |
| 2003/0195499 A1 | 10/2003 | Prakash et al. |
| 2003/0199755 A1 | 10/2003 | Halperin |
| 2003/0208199 A1 | 11/2003 | Keane |
| 2003/0212389 A1 | 11/2003 | Durgin |
| 2004/0006335 A1 | 1/2004 | Garrison |
| 2004/0030330 A1 | 2/2004 | Brassell et al. |
| 2004/0034349 A1 | 2/2004 | Kirwan, Jr. et al. |
| 2004/0049185 A1 | 3/2004 | Latterell et al. |
| 2004/0059345 A1 | 3/2004 | Nakao et al. |
| 2004/0073256 A1 | 4/2004 | Marchitto |
| 2004/0167506 A1 | 8/2004 | Chen |
| 2004/0176756 A1 | 9/2004 | McGaffigan |
| 2004/0187875 A1 | 9/2004 | He et al. |
| 2004/0243120 A1 | 12/2004 | Orszulak et al. |
| 2005/0021016 A1 | 1/2005 | Malecki et al. |
| 2005/0033338 A1 | 2/2005 | Ferree |
| 2005/0072827 A1 | 4/2005 | Mollenauer |
| 2005/0090817 A1 | 4/2005 | Phan |
| 2005/0107776 A1 | 5/2005 | Mcgaffigan et al. |
| 2005/0113824 A1 | 5/2005 | Sartor et al. |
| 2005/0197661 A1 | 9/2005 | Carrison et al. |
| 2005/0245919 A1 | 11/2005 | Van der Welde |
| 2005/0273111 A1 | 12/2005 | Ferree et al. |
| 2005/0283067 A1 | 12/2005 | Sobe |
| 2005/0283149 A1 | 12/2005 | Thorne et al. |
| 2005/0288659 A1 | 12/2005 | Kimura et al. |
| 2006/0004356 A1 | 1/2006 | Bilski |
| 2006/0127706 A1 | 6/2006 | Goebel et al. |
| 2006/0142824 A1 | 6/2006 | Zikorus et al. |
| 2006/0161149 A1 | 7/2006 | Privitera et al. |
| 2006/0167450 A1 | 7/2006 | Johnson et al. |
| 2006/0212030 A1 | 9/2006 | McGaffigan |
| 2006/0212031 A1 | 9/2006 | McGaffigan et al. |
| 2006/0217700 A1 | 9/2006 | Garito et al. |
| 2006/0217706 A1 | 9/2006 | Lau et al. |
| 2006/0241587 A1 | 10/2006 | Heim et al. |
| 2006/0241588 A1 | 10/2006 | Heim et al. |
| 2006/0241589 A1 | 10/2006 | Heim et al. |
| 2006/0271037 A1 | 11/2006 | Maroney et al. |
| 2006/0287649 A1 | 12/2006 | Ormsby |
| 2007/0005054 A1 | 1/2007 | Heim et al. |
| 2007/0005055 A1 | 1/2007 | Heim et al. |
| 2007/0005056 A1 | 1/2007 | Heim et al. |
| 2007/0005057 A1 | 1/2007 | Heim et al. |
| 2007/0005058 A1 | 1/2007 | Heim et al. |
| 2007/0005059 A1 | 1/2007 | Heim et al. |
| 2007/0005060 A1 | 1/2007 | Heim et al. |
| 2007/0016181 A1 | 1/2007 | van der Weide et al. |
| 2007/0016272 A1 | 1/2007 | Thompson et al. |
| 2007/0060920 A1 | 3/2007 | Weitzner |
| 2007/0073282 A1 | 3/2007 | McGaffigan et al. |
| 2007/0100336 A1 | 5/2007 | McFarlin et al. |
| 2007/0100405 A1 | 5/2007 | Thompson et al. |
| 2007/0106294 A1 | 5/2007 | Nesbitt |
| 2007/0127897 A1 | 6/2007 | John et al. |
| 2007/0131428 A1 | 6/2007 | Boestert |
| 2007/0173811 A1 | 7/2007 | Couture et al. |
| 2007/0208339 A1 | 9/2007 | Arts et al. |
| 2007/0219544 A1 | 9/2007 | Gowda et al. |
| 2007/0239151 A1 | 10/2007 | Atalar et al. |
| 2007/0270924 A1 | 11/2007 | McCann et al. |
| 2008/0017380 A1 | 1/2008 | Vinegar |
| 2008/0033419 A1 | 2/2008 | Nields et al. |
| 2008/0035346 A1 | 2/2008 | Nair et al. |
| 2008/0035347 A1 | 2/2008 | Brady |
| 2008/0035705 A1 | 2/2008 | Menotti |
| 2008/0038144 A1 | 2/2008 | Maziasz |
| 2008/0077129 A1 | 3/2008 | Van Wyk et al. |
| 2008/0119841 A1 | 5/2008 | Geisel |
| 2008/0128134 A1 | 6/2008 | Mudunuri et al. |
| 2008/0135253 A1 | 6/2008 | Vinegar |
| 2008/0135254 A1 | 6/2008 | Vinegar |
| 2008/0142216 A1 | 6/2008 | Vinegar |
| 2008/0142217 A1 | 6/2008 | Pieterson |
| 2008/0161800 A1 | 7/2008 | Wang et al. |
| 2008/0173444 A1 | 7/2008 | Stone et al. |
| 2008/0174115 A1 | 7/2008 | Lambirth |
| 2008/0185147 A1 | 8/2008 | Vinegar |
| 2008/0187989 A1 | 8/2008 | McGreevy et al. |
| 2008/0217003 A1 | 9/2008 | Kuhlman |
| 2008/0217016 A1 | 9/2008 | Stegemeier |
| 2008/0228135 A1 | 9/2008 | Snoderly |
| 2008/0236831 A1 | 10/2008 | Hsu |
| 2008/0255642 A1 | 10/2008 | Zarins et al. |
| 2008/0277113 A1 | 11/2008 | Stegemeier |
| 2008/0281310 A1 | 11/2008 | Dunning et al. |
| 2008/0281315 A1 | 11/2008 | Gines |
| 2008/0281386 A1 | 11/2008 | Herbette |
| 2008/0319438 A1 | 12/2008 | DeCarlo |
| 2009/0014180 A1 | 1/2009 | Stegemeier |
| 2009/0014181 A1 | 1/2009 | Vinegar |
| 2009/0093811 A1 | 4/2009 | Koblish et al. |
| 2009/0112200 A1 | 4/2009 | Eggers |
| 2009/0118729 A1 | 5/2009 | Auth et al. |
| 2009/0118730 A1 | 5/2009 | Mollenauer |
| 2009/0198224 A1 | 8/2009 | McGaffigan |
| 2009/0248002 A1 | 10/2009 | Takashino et al. |
| 2009/0292347 A1 | 11/2009 | Asmus et al. |
| 2009/0306644 A1 | 12/2009 | Mayse et al. |
| 2009/0312753 A1 | 12/2009 | Shadduck |
| 2010/0004650 A1 | 1/2010 | Ormsby et al. |
| 2010/0082022 A1 | 4/2010 | Haley et al. |
| 2010/0152725 A1 | 6/2010 | Pearson et al. |
| 2010/0198216 A1 | 8/2010 | Palanker |
| 2010/0228244 A1 | 9/2010 | Hancock et al. |
| 2010/0268205 A1 | 10/2010 | Manwaring et al. |
| 2010/0268206 A1 | 10/2010 | Manwaring et al. |
| 2010/0268207 A1 | 10/2010 | Manwaring et al. |
| 2010/0268208 A1 | 10/2010 | Manwaring et al. |
| 2010/0268209 A1 | 10/2010 | Manwaring et al. |
| 2010/0268210 A1 | 10/2010 | Manwaring et al. |
| 2010/0268211 A1 | 10/2010 | Manwaring et al. |
| 2010/0268212 A1 | 10/2010 | Manwaring et al. |
| 2010/0268213 A1 | 10/2010 | Manwaring et al. |
| 2010/0268214 A1 | 10/2010 | Manwaring et al. |
| 2010/0268215 A1 | 10/2010 | Manwaring et al. |
| 2010/0268216 A1 | 10/2010 | Manwaring et al. |
| 2010/0268218 A1 | 10/2010 | Ormsby et al. |
| 2011/0004204 A1 | 1/2011 | Dodde et al. |
| 2011/0054456 A1 | 3/2011 | Thompson et al. |
| 2011/0092971 A1 | 4/2011 | Sartor et al. |
| 2011/0152857 A1 | 6/2011 | Ingle |
| 2012/0059367 A1 | 3/2012 | Buysse et al. |
| 2012/0071712 A1 | 3/2012 | Manwaring et al. |
| 2012/0071870 A1 | 3/2012 | Salahieh et al. |
| 2012/0130256 A1 | 5/2012 | Buysse et al. |
| 2012/0150170 A1 | 6/2012 | Buysse et al. |

(56) References Cited

U.S. PATENT DOCUMENTS

| | | | |
|---|---|---|---|
| 2012/0226270 | A1 | 9/2012 | Manwaring et al. |
| 2012/0259323 | A1 | 10/2012 | Manwaring et al. |
| 2012/0296326 | A1 | 11/2012 | Manwaring et al. |
| 2012/0303026 | A1 | 11/2012 | Dycus et al. |
| 2012/0330295 | A1 | 12/2012 | Manwaring et al. |
| 2013/0006240 | A1 | 1/2013 | McNally et al. |
| 2013/0012934 | A1 | 1/2013 | Manwaring et al. |
| 2013/0023866 | A1 | 1/2013 | Stringham et al. |
| 2013/0041367 | A1 | 2/2013 | Wham et al. |
| 2013/0066310 | A1 | 3/2013 | Manwaring et al. |
| 2013/0218152 | A1 | 8/2013 | Manwaring et al. |
| 2014/0052119 | A1 | 2/2014 | Stewart et al. |
| 2014/0058381 | A1 | 2/2014 | Wham et al. |
| 2014/0058384 | A1 | 2/2014 | Buysse et al. |
| 2014/0058385 | A1 | 2/2014 | Wham et al. |
| 2014/0074082 | A1 | 3/2014 | Denis et al. |
| 2014/0100559 | A1 | 4/2014 | Wham et al. |
| 2014/0180266 | A1 | 6/2014 | Buysse et al. |
| 2015/0327907 | A1 | 11/2015 | Stringham et al. |
| 2016/0030102 | A1 | 2/2016 | Manwaring et al. |
| 2016/0192977 | A1 | 7/2016 | Manwaring et al. |
| 2016/0249971 | A1 | 9/2016 | Manwaring et al. |
| 2017/0189094 | A9 | 7/2017 | Manwaring et al. |
| 2017/0196617 | A1 | 7/2017 | Denis et al. |
| 2017/0209200 | A1 | 7/2017 | Manwaring et al. |

FOREIGN PATENT DOCUMENTS

| | | |
|---|---|---|
| EP | 2036512 | 3/2009 |
| EP | 2070486 | 6/2009 |
| GB | 2 022 974 | 12/1978 |
| GB | 1 546 624 | 5/1979 |
| JP | 03051179 | 8/1996 |
| JP | 2558584 | 9/1996 |
| JP | H10277050 | 10/1998 |
| RU | 2 072 118 | 1/1997 |
| WO | WO-82/00746 | 3/1982 |
| WO | WO-92/017121 | 10/1992 |
| WO | WO-93/021839 | 11/1993 |
| WO | 94/08524 A1 | 4/1994 |
| WO | WO-96/026677 | 11/1996 |
| WO | WO 9937227 A1 | 7/1999 |
| WO | WO-01/006943 | 2/2001 |
| WO | WO-04/014217 | 2/2004 |
| WO | WO-04/076146 | 9/2004 |
| WO | WO-06/017517 | 2/2006 |
| WO | WO-06/029649 | 3/2006 |
| WO | WO 2007080578 A2 | 7/2007 |
| WO | WO-08/060668 | 5/2008 |

OTHER PUBLICATIONS

Metcal Soldering Iron Catalog—2006.
URSI EMTS 2004, pp. 489-491, *Electromagnetic Probes for Living Tissue Cauterization*.
"High Temp Metals." NI2001201 Technical Data. High Temp Metals, Inc., n.d. Web. Jul. 13, 2012. <http://www.hightempmetals.com/techdatafnitempNi200data.php.
International Preliminary Report on Patentability from related PCT Patent Application No. PCT/US2010/031114, dated Nov. 1, 2011.
International Preliminary Report on Patentability from related PCT Patent Application No. PCT/US2010/031114, dated Jan. 21, 2011.
International Preliminary Report on Patentability from related PCT Patent Application No. PCT/US2011/050417, dated Apr. 12, 2012.
International Preliminary Report on Patentability from related PCT Patent Application No. PCT/US2012/032656, dated Oct. 23, 2012.
International Preliminary Report on Patentability from related PCT Patent Application No. PCT/US2012/032659, dated Nov. 23, 2012.
International Preliminary Report on Patentability from related PCT Patent Application No. PCT/US2012/038005, dated Nov. 23, 2012.
International Preliminary Report on Patentability from related PCT Patent Application No. PCT/US2012/055229, dated Feb. 1, 2013.
Written Opinion of the International Preliminary Examining Authority from related PCT Patent Application No. PCT/US2011/050417, dated Feb. 6, 2013.
International Preliminary Report on Patentability from related PCT Patent Application No. PCT/US2012/068027, dated Feb. 25, 2013.
Visioli, Antonio. Practice PID Control: London: Springer-Verlag, 2006. 1-18. Print.
International Search Report and Written Opinion from related PCT Application US2012/032661, dated Aug. 19, 2013.
International Search Report and Written Opinion from related PCT Application US2012/032659, dated Oct. 8, 2013.
International Search Report and Written Opinion from related PCT Application US2012/032565, dated Oct. 8, 2013.
International Preliminary Report on Patentability from related PCT Application US2012/038005, dated Nov. 19, 2013.
International Preliminary Report on Patentability from related PCT Application US2012/068027, dated Jun. 19, 2014.
Translation of Office Action from related Japanese Patent Application No. 2012-506188, PCT US2010-031114.
European Search Report from European Application No. 12865504.0-1652, dated Nov. 28, 2014.
Supplemental European Search Report from European Application No. 12767458, dated Jan. 30, 2015.
Supplementary European Search Report from related European patent application No. EP 10 76 5134, dated Nov. 10, 2016.
Denis et al., "System and Method of Controlling Power Delivery to an Electrosurgical Instrument," U.S. Appl. No. 61/669,671, filed Jul. 10, 2012, 59 pages.
Denis et al., "Thermal Surgical Tool," U.S. Appl. No. 61/567,603, filed Dec. 6, 2011, 33 pages.
International Preliminary Report on Patentability, dated Oct. 8, 2013, for International Application No. PCT/US2012/032661, 8 pages.
International Search Report and Written Opinion, dated Feb. 1, 2013, for International Application No. PCT/US2012/055229, 11 pages.
International Search Report and Written Opinion, dated Feb. 15, 2013, for International Application No. PCT/US2012/068027, 8 pages.
International Search Report and Written Opinion, dated Jan. 21, 2011, for International Application No. PCT/US2010/031114, 12 pages.
International Search Report and Written Opinion, dated Nov. 23, 2012, for International Application No. PCT/US2012/038005, 9 pages.
International Search Report and Written Opinion, dated Oct. 23, 2012, for International Application No. PCT/US2012/032656, 13 pages.
Manwaring et al., "Adjustable Ferromagnetic Coated Conductor Thermal Surgical Tool," U.S. Appl. No. 61/170,203, filed Apr. 17, 2009, 36 pages.
Manwaring et al., "Surgical Multi-Mode Tool With Ferromagnetic Coated Conductor for Adjustable Thermal Energy Delivery," U.S. Appl. No. 61/170,207, filed Apr. 17, 2009, 43 pages.
Manwaring et al., "Thermally Adjustable Surgical or Therapeutic Tool and Method of Use," U.S. Appl. No. 61/170,220, filed Apr. 17, 2009, 41 pages.

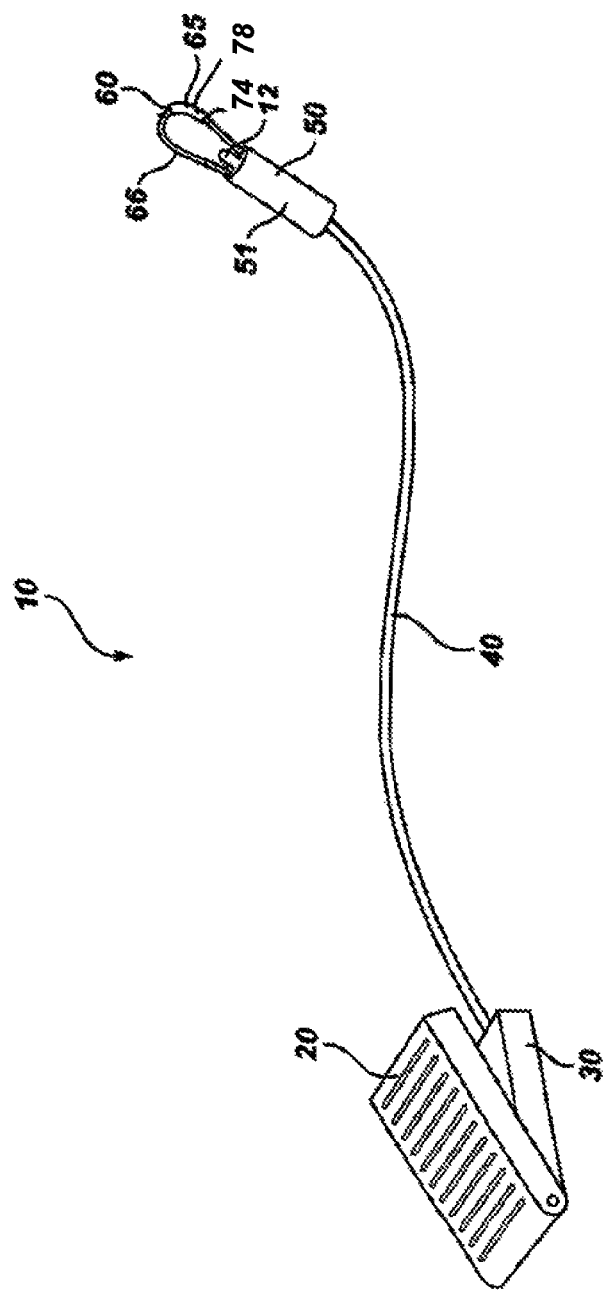

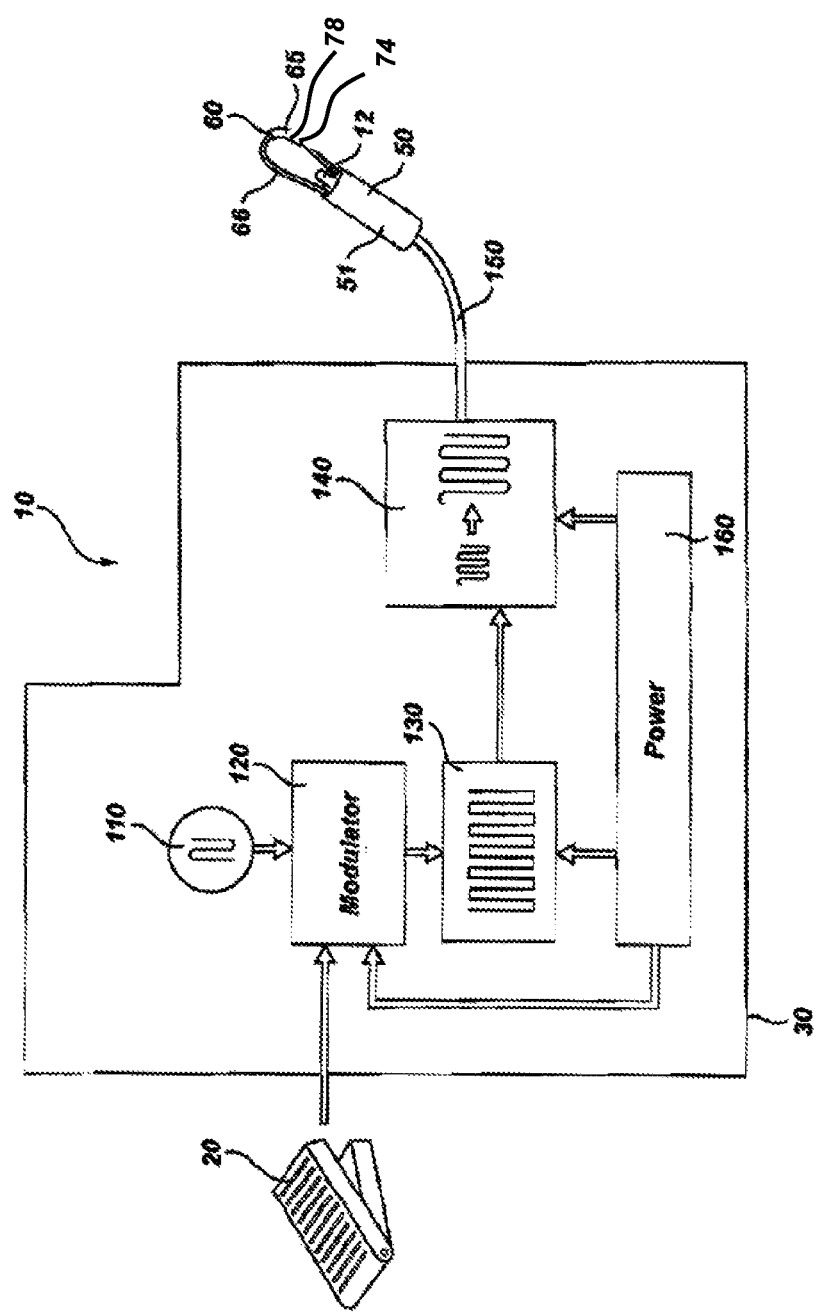

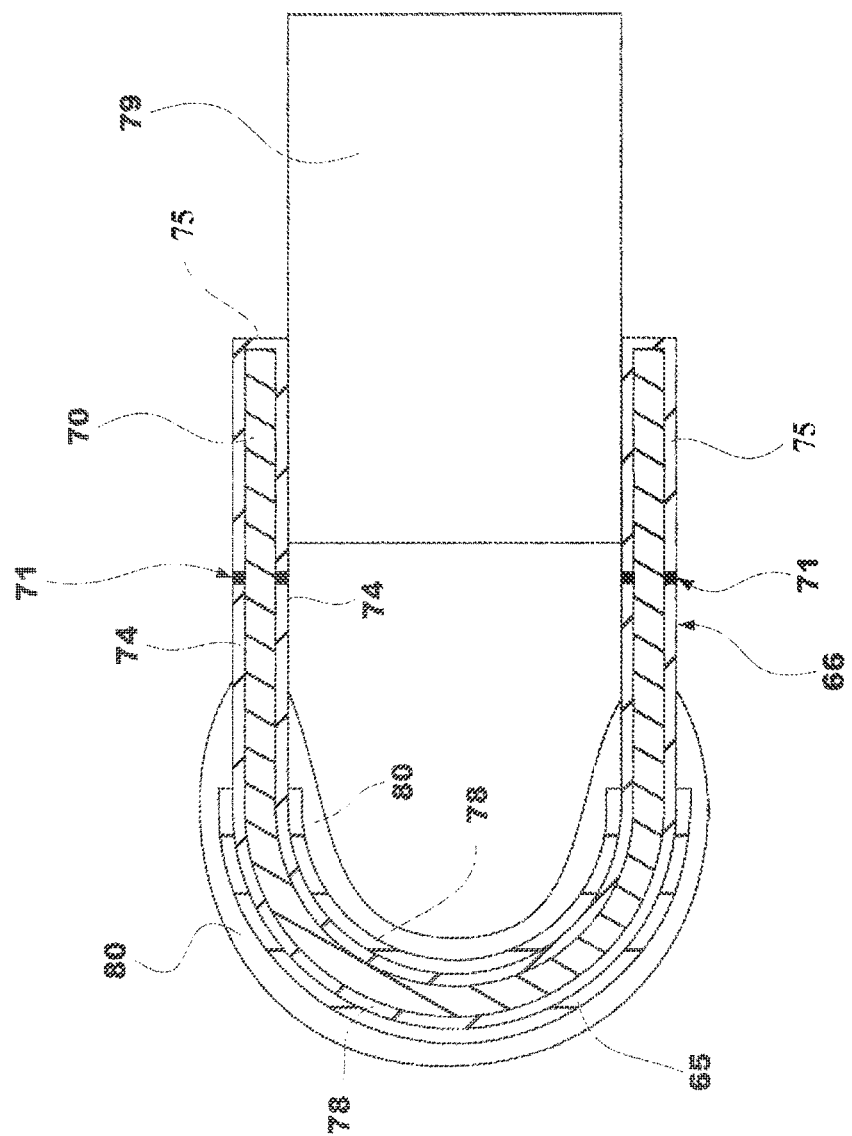

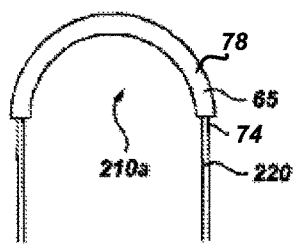 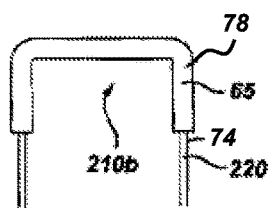 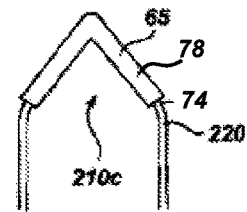
*Fig. 7A*   *Fig. 7B*   *Fig. 7C*
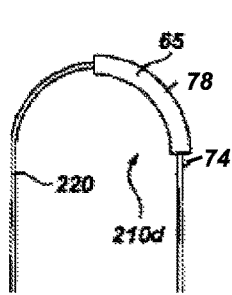 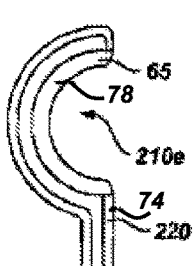 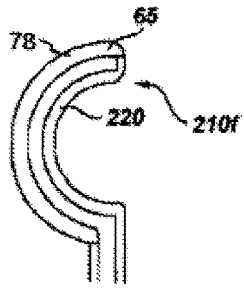 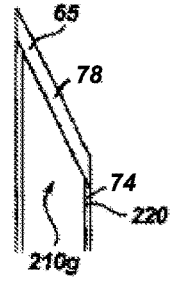
*Fig. 7D*   *Fig. 7E*   *Fig. 7F*   *Fig. 7G*

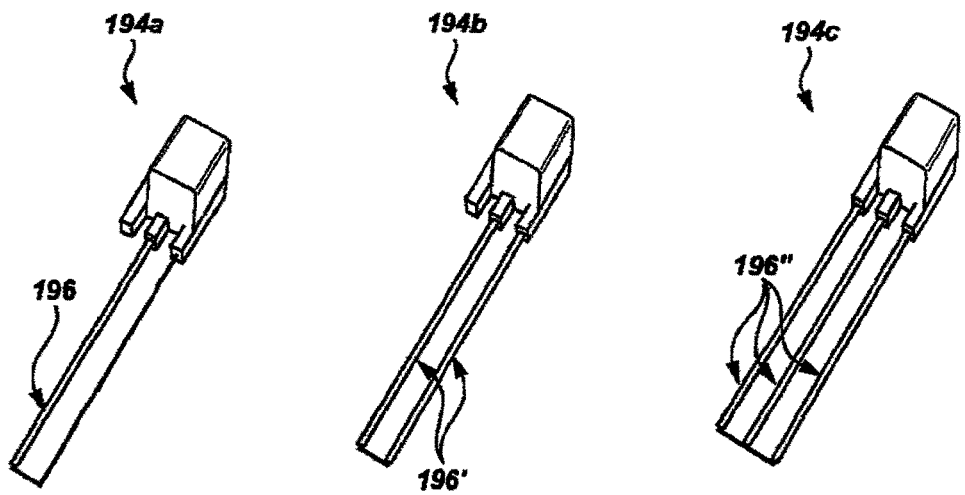
Fig. 18A  Fig. 18B  Fig. 18C
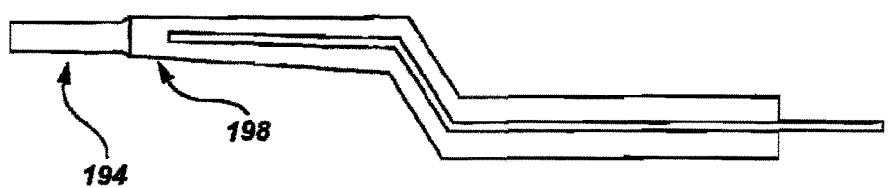
Fig. 18D

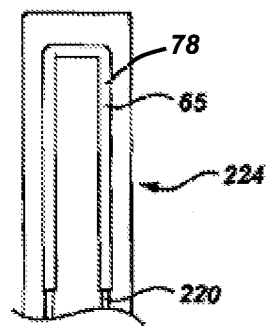 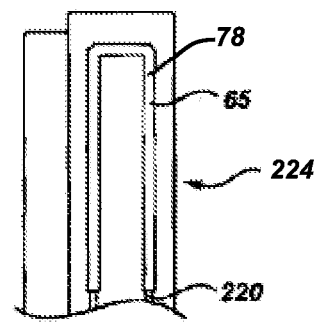
Fig. 20A  Fig. 20B
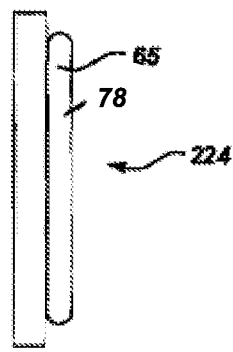 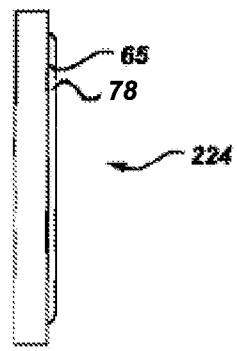
Fig. 20C  Fig. 20D

LAYERED FERROMAGNETIC COATED CONDUCTOR THERMAL SURGICAL TOOL

BACKGROUND OF THE INVENTION

1. The Field of the Invention

The present invention relates to surgical tools. More specifically, the present invention relates to thermal surgical tools used in open and minimally invasive surgical procedures and interventional surgical and therapeutic procedures and methods for making the same.

2. State of the Art

Surgery generally involves cutting, repairing and/or removing tissue or other materials. These applications are generally performed by cutting tissue, fusing tissue, or tissue destruction. There are currently a number of electrosurgery modalities used for cutting, coagulating, desiccating, ablating, or fulgurating tissue, which have undesirable side effects and drawbacks. These include monopolar and bipolar electrosurgery modalities, electrocautery resistive heating elements, ferrite beads and alloy mixes in ceramics, lasers, and microwave antenna.

Tissue destruction instruments generally heat tissue to a predetermined temperature for a period of time to kill, or ablate, the tissue. However, each of these modalities has inherent disadvantages.

A significant improvement in electrosurgery was developed wherein a thin ferromagnetic coating is placed over a conductor. As an oscillating electrical energy source is passed through the conductor, inductive and/or other types of heating may be caused in the ferromagnetic coating. Moreover, the surgeon may be able to quickly turn the surgical or therapeutic tool on and off due to a small heat latency in the thin ferromagnetic coating. A detailed discussion of the design and use of ferromagnetic surgical instruments is contained in U.S. Patent Publication Nos. 2010-0268207, 2010-0268214, 2010-0268208, 2010-0268209, 2010-0268215, 2010-0268205, 2010-0268210, 2010-0268212, 2010-0268213, 2010-0268211, and 2010-0268216, 2010-0268206, which are applications related to the present application and are incorporated herein by reference.

One challenge with ferromagnetic electrosurgery instruments is obtaining a proper rigidity in the working element, and in ensuring proper conductivity and attachment of the ferromagnetic layer. While some materials work well for rigidity, such as tungsten, their less desirable conductivity may cause resistive heating in the conductor. This can create latent heat in the electrosurgical instrument and reduce the ability of the instrument to cool down when the working element is not active.

Additionally, some materials are difficult to securely attach the ferromagnetic material to. If the ferromagnetic material does not adhere well, there is a risk of some of the material coming off in the patient.

Still another concern with electrosurgical instruments is that the material should be biocompatible. While some materials work well as a ferromagnetic coating to create the desired heat, they may not be desirable for direct contact with human tissues. Thus, there is a need for an improved ferromagnetic electrosurgical instrument.

SUMMARY OF THE INVENTION

It is an object of the present invention to provide an improved thermally adjustable surgical or therapeutic tool. For ease of references, the device will be referred to as a surgical tool and the user referred to as surgeon. It will be understood however, the devices may be used for therapeutic purposes other than surgery and may be used for a variety of non-medical purposes as well.

According to one aspect of the invention, a thermal surgical tool is provided with a support which forms part of a working element of the surgical tool. At least one conductive intervening layer is disposed on the support with a ferromagnetic coating disposed in communication with the at least one conductive intervening layer. The support may be selected from a material with desired rigidity/flexibility characteristics for the particular procedure being performed and may be conductive or non-conductive. The tool is typically disposed in communication with a source of oscillating electrical energy to cause heating of the ferromagnetic coating. The ferromagnetic coating may heat rapidly when the surgical tool is actuated, e.g. oscillating electrical energy is directed through the conductor. The surgical tool may also cool rapidly once the oscillating electrical energy is no longer passed through the conductor due to a small heat latency. This may provide the advantage of allowing a surgeon to deliver a thermal effect only at desired locations, and also limit or prevent the accidental delivery of undesired thermal effects to a patient while waiting for the surgical tool to cool.

According to one aspect of the invention the at least one intervening layer is a highly conductive material, such as copper, silver or other highly conductive materials, so that the intervening layer forms a conductor through which the majority of the energy is passed to thereby heat the ferromagnetic layer. A highly conductive intervening layer allows use of a variety of materials for the support, including non-conductive materials and materials which are conductive but might be prone to resistive heating or have other undesirable properties.

According to another aspect of the invention, at least one intervening layer may be an attachment or bonding layer which helps in the attachment of the ferromagnetic material. A desirable bonding layer may include, for example, nickel strike plate, gold flash or other materials to which a particular ferromagnetic material or other intervening layers can be more easily attached.

According to another aspect of the invention, a plurality of intervening layers may be used to both increase conductivity of energy and to increase the attachability of the ferromagnetic material. Thus, for example, a conductor may include a tungsten support having a bonding layer, such as nickel strike or gold flash, attached to the support and extending along at least a portion of the support. The bonding layer may then have one or more conductive layers, such as copper, silver, gold, etc., attached to the bonding layer and extending along at least a portion of the bonding layer. The ferromagnetic material may then be attached to the conductor via the one or more conductive layers. Such a configuration may improve the connection of the ferromagnetic material to the conductor. Additionally, by constructing the conductor from several materials which may form a plurality of layers, a conductor having optimal desired properties can be achieved, e.g. resistance to bending (i.e. Young's Modulus), electrical and thermal conductivity, resistivity, attachability of the ferromagnetic layer, heat capacity, etc.

According to yet another aspect of the invention, the ferromagnetic coating may be a first material and may be coated with a second material made of a different material which is biocompatible. The biocompatible layer may also minimize oxidation of underlying materials, e.g. the plurality of layers forming the conductor and/or the ferromagnetic material.

BRIEF DESCRIPTION OF THE DRAWINGS

Various embodiments of the present invention are shown and described in reference to the numbered drawings wherein:

FIG. 2 shows a perspective view of a thermal surgical tool system in accordance with the present invention;

FIG. 3 shows a diagram of a thermal surgical tool system in accordance with the principles of the present invention;

FIG. 4D shows a side cross-sectional view of a portion of a thermal surgical tool system according to principles of the present invention;

FIG. 7A shows a close-up view of ferromagnetic coated conductor surgical tool tip with a loop geometry in accordance with one aspect of the present invention;

FIG. 7B shows a close-up view of a ferromagnetic coated conductor surgical tool tip with a generally square geometry in accordance with one aspect of the present invention;

FIG. 7C shows a close-up view of a ferromagnetic coated conductor surgical tool tip with a pointed geometry;

FIG. 7D shows a close-up view of a ferromagnetic coated conductor surgical tool tip with an asymmetrical loop geometry;

FIG. 7E shows a close-up view of a ferromagnetic coated conductor surgical tool tip with a hook geometry in which the concave portion may be used for therapeutic effect, including cutting;

FIG. 7F shows a close up view of a ferromagnetic coated conductor surgical tool tip with a hook geometry in which the convex portion may be used for therapeutic effect, including cutting;

FIG. 7G shows a close up view of a ferromagnetic coated conductor surgical tool tip with an angled geometry;

FIG. 18A shows a single edge ferromagnetic coated conductor surgical tool tip in accordance with one aspect of the invention;

FIG. 18B shows a double edge ferromagnetic coated conductor surgical tool tip;

FIG. 18C shows a three wire ferromagnetic coated conductor surgical tool tip;

FIG. 18D shows a receptacle for the tips shown in FIGS. 18A through 18C;

FIG. 20A shows a thermal surgical tool with a spatula shaped geometry;

FIG. 20B shows a thermal surgical tool with a spatula shaped geometry in a forceps configuration;

FIG. 20C shows a top view of the thermal surgical tool of FIG. 20A with a ferromagnetic coated conductor upon the primary geometry;

FIG. 20D shows a top view of the thermal surgical tool of FIG. 20A with a ferromagnetic coated conductor embedded within the primary geometry;

It will be appreciated that the drawings are illustrative and not limiting of the scope of the invention which is defined by the appended claims. The embodiments and configurations shown accomplish various aspects and objects of the invention. It is appreciated that it is not possible to clearly show each element and aspect of the invention in a single figure, and as such, multiple figures are presented to separately illustrate the various details of the invention in greater clarity. Similarly, not every embodiment need accomplish all advantages of the present invention.

DETAILED DESCRIPTION

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims. As used herein, the term "ferromagnetic," "ferromagnet," and "ferromagnetism" refers to any ferromagnetic-like material that is capable of producing heat via magnetic induction, including but not limited to ferromagnets and ferrimagnets. It is not intended that such materials must be heated exclusively by magnetic induction unless otherwise indicated and such may acquire heat from resistive heating, eddy currents, etc., in addition to magnetic induction.

Figure 1:
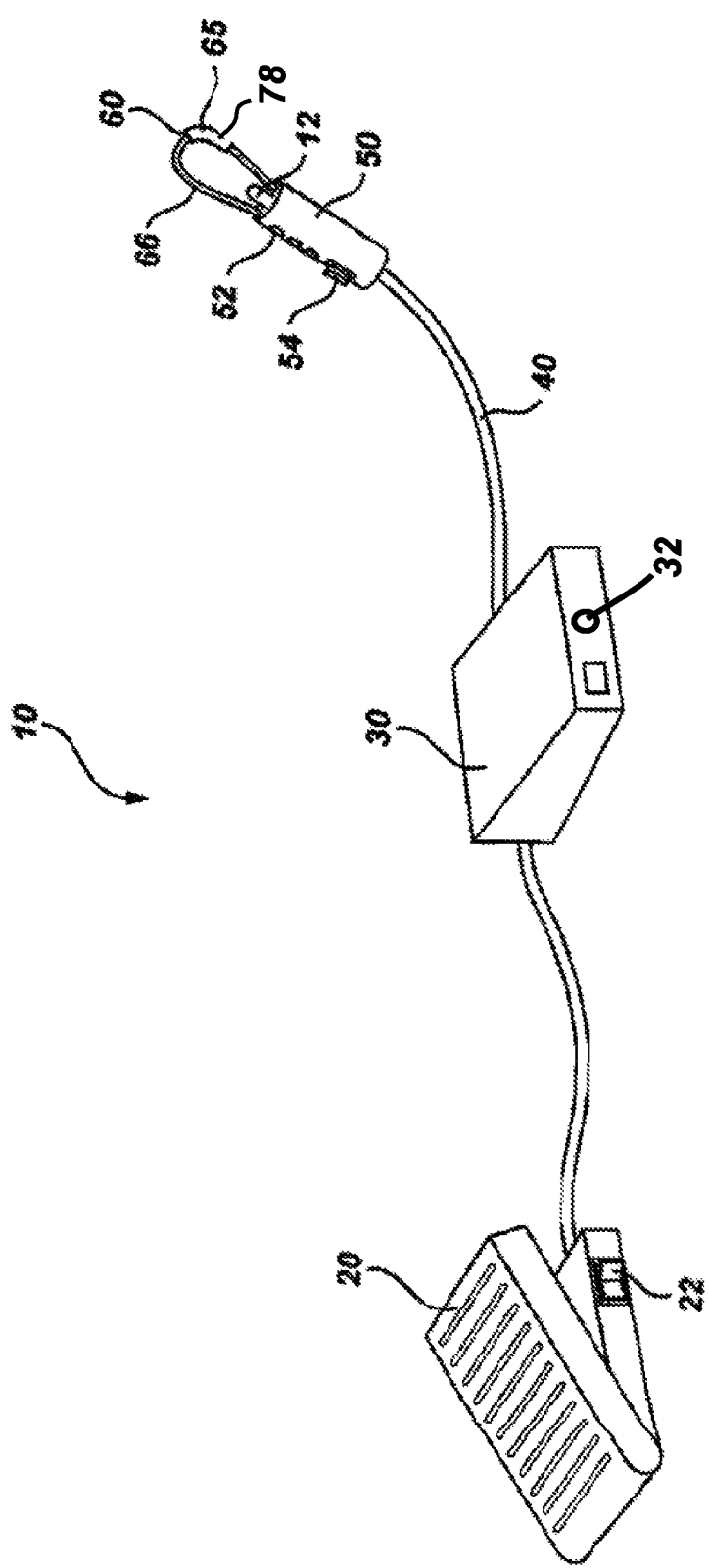
FIG. 1 shows a perspective view of a thermal surgical tool system in accordance with the principles of the present invention.

Turning now to FIG. 1, there is shown a perspective view of a thermal surgical tool system, generally indicated at 10. As will be discussed in additional detail below, the thermal tool system preferably uses a ferromagnetic coated conductor to treat or destroy tissue (i.e. cutting, endothelial tissue welding, homeostasis, ablation, etc.).

It will be appreciated that the thermal surgical tool uses heat to incise tissue and may not cut tissue in the sense of a sharp edge being drawn across the tissue as with a conventional scalpel. While the embodiments of the present invention could be made with a relatively sharp edge so as to form a cutting blade, such is not necessary as the heated coating discussed herein will separate tissue without the need for a cutting blade or sharp edge. However, for convenience, the term cutting is used when discussing separating tissue.

In thermal surgical tool system 10, a control mechanism, such as a foot pedal 20 is used to control output energy produced by a power subsystem 30. The energy from the power subsystem 30 may be sent via radio frequency (RF) or oscillating electrical energy along a cable 40 to a handheld surgical tool 50, which contains a conductor portion 60 having a section thereof circumferentially coated with a ferromagnetic portion 65. The ferromagnetic portion 65 may transfer the electrical energy into available thermal energy. This may be done, for example, via induction and corresponding hysteresis losses in the ferromagnetic material disposed around a conductor wire 66. (While conductor wire may be used for ease of reference, it will be appreciated that the conductor material need not be a wire and those skilled in the art will be familiar with multiple conductors which will work in light of the disclosure of the present invention. Additionally, as will be explained below, the conductor wire 66 may be include a support (either conductive or not) covered by a conductive coating).

Application of a magnetic field (or magnetizing) to the ferromagnetic coating may produce an open loop B-H curve (also known as an open hysteresis loop), resulting in hysteresis losses and the resultant thermal energy. Electrode-posited films, such as a nickel-iron coating like PERMALLOY™, may form an array of randomly aligned microcrystals, resulting in randomly aligned domains, which together may have an open loop hysteresis curve when a high frequency current is passed through the conductor.

The RF energy may travel along the conductor's surface in a manner known as the "skin effect". The current density is generally greatest at the surface and decreases in magnitude farther into the material where the electric field approaches zero. The depth at which the skin effect current is reduced to about 37 percent of its surface value is referred to as the skin depth and is a function of the electrical resistivity, the magnetic permeability of the material conducting the current, and the frequency of the applied alternating RF current.

The alternating RF current in the conductor's surface produces an alternating magnetic field, which may excite the domains in the ferromagnetic portion 65. As the domains realign with each oscillation of the current, hysteresis losses in the coating may cause inductive heating. Heating of the ferromagnetic portion 65 due to hysteresis loss ceases above the Curie point because the material loses its magnetic properties.

The RF conductor from the signal source up to and including the tip may form a resonant circuit at a specific frequency (also known as a tuned circuit). Changes in the tip "detune" the circuit. Thus, should the ferromagnetic portion 65 or the conductor 66 become damaged, the circuit may likely become detuned. This detuning should reduce the efficiency of the heating of the ferromagnetic portion 65 such that the temperature will be substantially reduced. The reduced temperature should ensure little or no tissue damage after breakage.

It should be understood that the surgical tool 50 may include indicia of the power being applied and may even include a mechanism for controlling the power. Thus, for example, a series of lights 52 could be used to indicate power level, or the handheld surgical tool 50 could include a switch, rotary dial, set of buttons, touchpad or slide 54 that communicates with the power source 30 to regulate power and thereby affect the temperature at the ferromagnetic portion 65 to having varying effects on tissue. While the controls are shown on the foot pedal 20 or the handheld surgical tool 50, they may also be included in the power subsystem 30 or even a separate control instrument. Safety features such as a button or touchpad that must be contacted to power the handheld surgical tool 50 may be employed, and may include a dead man's switch.

The ferromagnetic material 65, such as a ferromagnetic coating 78 may have a calculable Curie temperature. A Curie temperature is the temperature at which the material becomes paramagnetic, such that the magnetic properties of the coating are lost. When the material becomes paramagnetic, the ferromagnetic heating may be significantly reduced or even cease. Theoretically, this should cause the temperature of the ferromagnetic material 65 to stabilize around the Curie temperature if sufficient power is provided to reach the Curie temperature. However, it has been found that the temperature of the ferromagnetic material 65 may exceed its calculated Curie temperature under certain operational conditions. It has been observed that if sufficient power has been applied, the tip temperature can continue to rise due to resistive heating in the overall conductor and the tip can potentially exceed the Curie temperature. When this occurs, an increase in current is observed while operating at a constant power level. It is believed that this may be due, at least in part to an increase in the skin depth and a resulting drop in impedance above the Curie temperature. The increase may also be due to the resistance of the ferromagnetic coating dropping and raising the current level for a fixed power level. The increased current may then cause more resistive heating in the non-ferromagnetic portion of the conductor. Thus, it may be preferable to have a high conductivity in the conductor.

The thermal surgical tool system 10 allows the power output to be adjustable in order to adjust the temperature of the tool and its effect on tissue. This adjustability gives the surgeon precise control over the effects that may be achieved by the handheld surgical tool 50. Tissue effects such as cutting, hemostasis, tissue welding, tissue vaporization and tissue carbonization occur at different temperatures. By using the foot pedal 20 (or some other user control, such as a dial 32 on the power subsystem 30) to adjust the power output, the surgeon (or other physician, etc.) can adjust the power delivered to the ferromagnetic portion 65 and consequently control the tissue effects to achieve a desired result. The foot pedal 20 may also be configured only to provide on and off, with the dial controlling power level.

Thermal power delivery can be controlled by varying the amplitude, frequency or duty cycle of the alternating current waveform, or alteration of the circuit to affect the standing wave driving the ferromagnetic coated conductor, which may be achieved by input received by the foot pedal 20, the power subsystem 30, or the controls on the handheld surgical tool 50.

One additional advantage achieved by the inductive or other ferromagnetic heating is that the ferromagnetic material can be heated to a cutting temperature in a small fraction of a second (typically as short as one quarter of a second). Additionally, because of the relatively low mass of the coating, the small thermal mass of the conductor, and the localization of the heating to a small region due to construction of the handheld surgical tool 50, the material will also cool extremely rapidly (i.e. as low as approximately one half of a second). This provides a surgeon with a precise thermal tool while reducing accidental tissue damage caused by touching tissue when the thermal tool is not activated.

It will be appreciated that the time period required to heat and cool the handheld surgical tool 50 will depend, in part, on the relative dimensions of the conductor 60 and the ferromagnetic portion 65 and the heat capacity of the structure of the surgical tool. For example, the above time periods for heating and cooling of the handheld surgical tool 50 can be achieved with a tungsten conductor having a diameter of about 0.375 mm and a ferromagnetic coating of a Nickel Iron alloy (such as NIRON™ available from Enthone, Inc. of West Haven, Conn.) about the tungsten conductor about 0.0375 mm thick and two centimeters long.

One advantage of the present invention is that a sharp edge is not needed. When power is not being supplied to the surgical tool, the tool will not inadvertently cut tissue of the patient or of the surgeon if it is dropped or mishandled. If power is not being supplied to the conductor 66 and coating 78, the "cutting" portion of the tool may be touched without risk of injury. This is in sharp contrast to a cutting blade which may injure the patient or the surgeon if mishandled.

Other additions may also be placed on the handpiece in various locations. This may include a sensor stem 12 including a sensor to report temperature or a light to illuminate the surgical area.

Figure 1A:
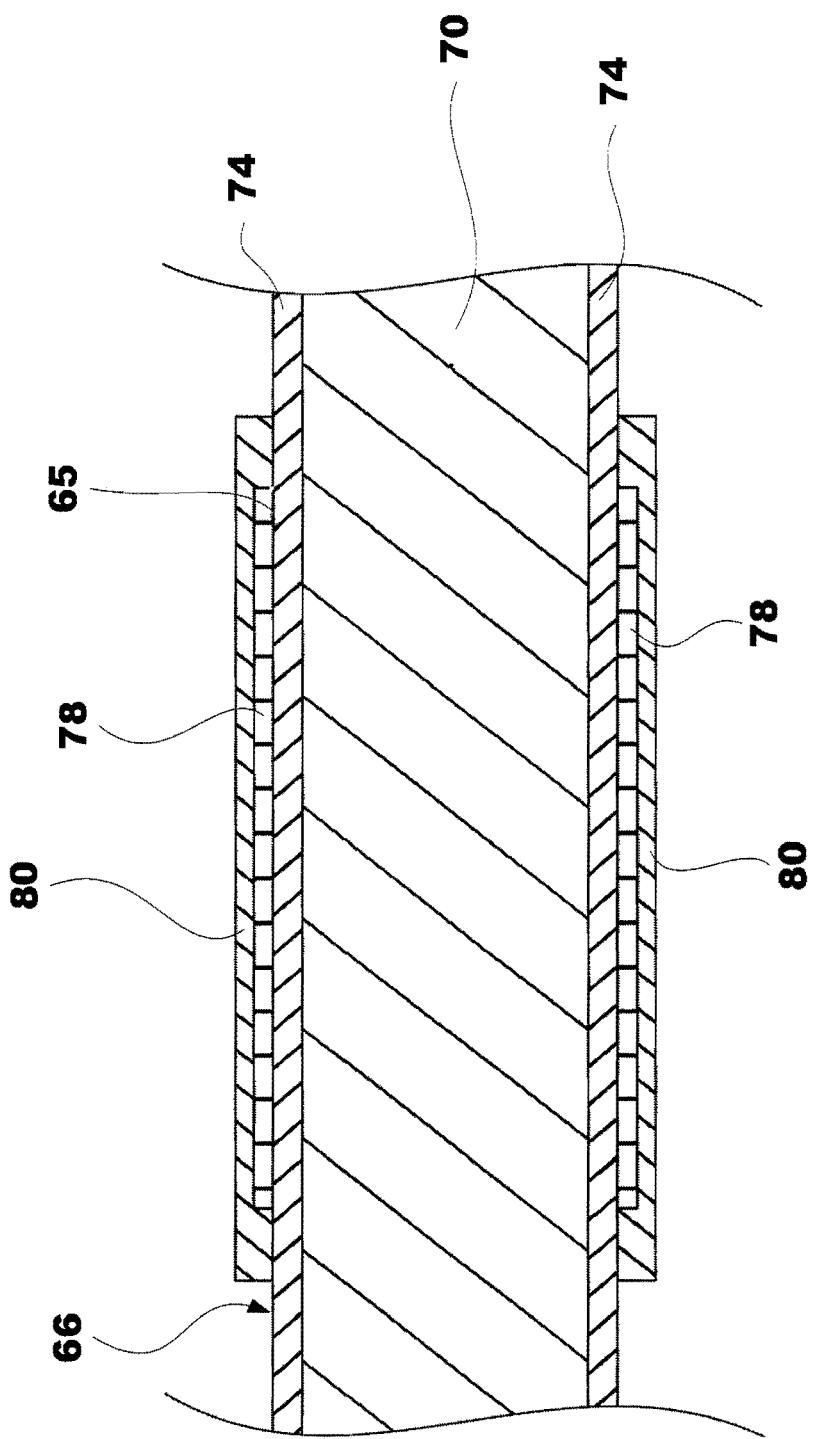
FIG. 1A shows a close-up cross-sectional view of a portion of a tip of the thermal surgical tool system of FIG. 1.

Turning now to FIG. 1A, there is shown a cross-sectional view of a portion of a surgical tip having a conductor 66, such as a conductor wire, in accordance with one aspect of the invention. It may be desirable that the conductor 66 have a relatively small diameter or cross-section so as to make precise cuts in tissue, or other materials. However, it is also desirable to have the conductor 66 be relatively stiff and resist bending when encountering tissue. To accomplish these ends, the conductor 66 may include a support 70 which will resist bending even when the support has a fairly small diameter or cross-section. Examples of metals having this property may include tungsten, titanium, stainless steel, Haynes 188, Haynes 25, etc.

In addition to the Young's Modulus of the support 70, other properties of the material used for the support 70 may be important. These properties may include the resistivity of the material, the thermal and electrical conductivity of the material, the material's heat capacity, the material's coefficient of thermal expansion, the annealing temperature of the material, and the ability to plate a second material to the material comprising the support 70.

In choosing a material to use as the support 70, it may be important that such material have the greatest amount of resistance to bending while having low resistivity to minimize heating of the conductor 66 due to resistance heating. Additionally, it may also be important that the material have a low heat capacity so that heat is not stored in the conductor 66 thus allowing the surgical tip to cool rapidly when not being used. This may help limit or prevent collateral damage to structures adjacent the surgical site.

Additionally, it is desirable that the support 70 be comprised of material having a sufficiently high annealing temperature. At times, the surgical tip may be operated at temperatures, for example, between 400 degrees Celsius and 450 degrees Celsius. Thus, to avoid alterations in the properties of the support 70, the annealing temperature of the material used as the support 70 should be sufficiently higher than the expected operating ranges of the surgical tip.

Furthermore, it may be desirable that the support 70 be comprised of a material having a coefficient of thermal expansion value that is close to the coefficient of thermal expansion of the ferromagnetic material 65, such as a ferromagnetic coating 78, to facilitate plating of the ferromagnetic coating 78 to the support 70 in some configurations.

It has been observed, however, that some materials having adequate resistance to bending (Young's modulus) during normal operation of the surgical tip may have a coefficient of thermal expansion that is too low for adequate plating integrity. Thus, one or more intervening layers having an intermediate coefficient of thermal expansion may be plated on the support 70 and then the ferromagnetic layer or coating 78 plated on the one or more intervening layers to provide for a transition to accommodate the difference between the coefficients of thermal expansion of the support 70 and the ferromagnetic material 65, as described in more detail below.

Another important factor regarding the material used for the support 70 is its ability to conduct electricity. There are multiple materials which provide adequate support, but which are not sufficiently conductive. Thus a conductor 66 may be comprised of multiple layers of different material so as to minimize any undesirable property or properties of the support 70.

For example, the support 70 may be conductive or non-conductive, and may have a one or more conductive intervening layers 74 disposed thereon, such as copper, silver, etc. or other conductive material. The intervening layer allows the energy to pass without significant resistive heating, thus allowing the tip to cool down more rapidly. (It will be appreciated that the cross-sectional view of FIG. 1A is not necessarily to scale and the support may be much larger in diameter than the thickness of the other layers discussed herein. Moreover, it will be appreciated that the conductive intervening layer 74 may extend the entire length of the conductor 66 as will be discussed in more detail below).

The material or substrate used as the support 70 may have an optimal thermal conductivity to allow for conductive cooling of the surgical tip when energy is not being delivered to the conductor 66. Furthermore, the support 70 will have a sufficiently high Young's modulus to resist bending when the surgical tool is being used to provide a thermal therapeutic effect to tissue during a procedure. For example, the support 70 may be comprised of a material having a Young's Modulus (modulus of elasticity) of greater than 17 psi (118 GPa). According to one aspect of the invention, the support 70 may be comprised of a material having a Young's Modulus of about 58 psi (400 GPa) or greater, such as tungsten.

Furthermore, it is desirable that the intervening layer 74 be readily attachable to the support 70. This may be accomplished by using a substrate as the support 70 that allows for electroplating of the intervening layer 74 thereto under reasonable commercial standards. For example, the substrate may be easily deoxidized ("activated") to facilitate plating of the intervening layer 74 to the support 70.

The one or more conductive intervening layers 74 may comprise a variety of materials, such as copper, silver, etc., having desired properties. The intervening layer 74 may be disposed along a portion of the support or substantially extend along the entire length of the support 70. An important property of the intervening layer 74 is that it be a good electrical conductor having low resistivity such that heating due to the resistance of the intervening layer 74 is minimized. Furthermore, it is desirable in some configurations that one of the intervening layer(s) 74 not only be readily attachable to the support 70, but also be a good substrate for attaching the ferromagnetic material 65, such as a ferromagnetic layer or coating 78 thereto. Like the support 70, this may be accomplished by using a substrate as the intervening layer 74 that allows for electroplating of a ferromagnetic coating 78 thereto under reasonable commercial standards, such as a substrate that is easily activated to facilitate plating of the ferromagnetic layer 78.

Another important property of the intervening layer 74 in some configurations may be malleability. If the coefficient of thermal expansion of the intervening layer 74 differs significantly from the coefficient of thermal expansion of the support 70, the intervening layer 74 may have to be sufficiently malleable so that the integrity of the intervening layer 74 is not easily compromised when subjected to the thermal conditions under which the surgical tip is operated. For example, a surgical tip including an intervening layer 74 comprised of copper having a linear coefficient of thermal expansion of approximately 17 μm/° C. attached to a support 70 comprised of tungsten having a linear coefficient of thermal expansion of approximate 4.5 μm/° C. may be sufficient to withstand the heat variability that the surgical tip undergoes under normal operation.

The conductor 66 of FIG. 1A also shows a ferromagnetic layer or coating 78 disposed adjacent to the intervening layer 74. As discussed above, the ferromagnetic layer of coating 78 may be plated on the intervening layer 74. The ferromagnetic material 78 may be located along a portion of the conductor 66 at a defined location (or locations) so as to provide for localized heating along the surgical tip only in an area where heating is desired. For example, the ferromagnetic layer or coating 78 may be located along less than about 90%, 50%, 10%, etc. of the length of the conductor 66 so as to provide localized heating in a desired area. In other words, the length which the ferromagnetic material extends may be less than the length of the conductor 66. The ferromagnetic coating 78 may have high permeability to facilitate inductive or other ferromagnetic heating of the ferromagnetic material, such as NIRON™, PERMALLOY™, Co, CrO2, etc. Additionally, the ferromagnetic coating 78 may have a relatively high thermal conductance and low heat capacity to facilitate rapid heating and cooling of the surgical tip.

According to one aspect of the invention the surgical tip may include a ferromagnetic material 65, such as a ferromagnetic coating 78, having a coefficient of thermal expansion that varies significantly from the coefficient of thermal expansion of the support 70. Such a surgical tip may also include at least one intervening layer 74 having a coefficient of thermal expansion with an intermediate value to accommodate the differences in the coefficient of thermal expansions of the ferromagnetic coating 78 and the support 70. Such a configuration may help maintain the integrity of the surgical tip under expected operating conditions.

The ferromagnetic coating 78 may be exposed or may be covered with an exterior coating 80 made from a biocompatible material to ensure that there is no reaction between the ferromagnetic coating 78 and the patient tissues. The exterior coating 80 may also act as a lubricant between the surgical tip and tissue which is being treated by reducing the attachment of biologic tissues to the surgical tip. For example, the exterior coating 80 may be titanium nitride (or one of its variants), TEFLON or a host of other biocompatible materials.

The exterior layer 80 may also act as an oxygen barrier to prevent oxidation of the layer of ferromagnetic material 65, any intervening layer 74, and/or the support 70. For example, it has been observed that oxidation of the support 70 may cause the support 70 to become brittle making the support 70 more susceptible to damage. It will be appreciated that the exterior layer 80 may be disposed on the conductor 66 so as to substantially cover the ferromagnetic material and the entire conductor 66. Alternatively, the exterior layer may be disposed on the conductor 66 so as to cover the ferromagnetic coating 78 and only a portion of the conductor 66.

According to one aspect of the invention, a conductor 66 (such as the one shown in FIG. 1A) may comprise a support 70 having a diameter of about 500-750 μm, an intervening layer 74 having a cross-sectional thickness of about 20-50 μm (or about 2-5 skin depths), and a ferromagnetic material 65 (e.g. a coating 78) having a cross-sectional thickness of about 2-10 µm. The thickness of the ferromagnetic material forming the layer or coating 78 may be selected as a function of the skin depths of the intervening layer 74, or the combined skin depths of multiple intervening layers if such are included in a surgical tip as described below. The antioxidation layer may be very thin, such as 1-3 µm.

Figure 1B:
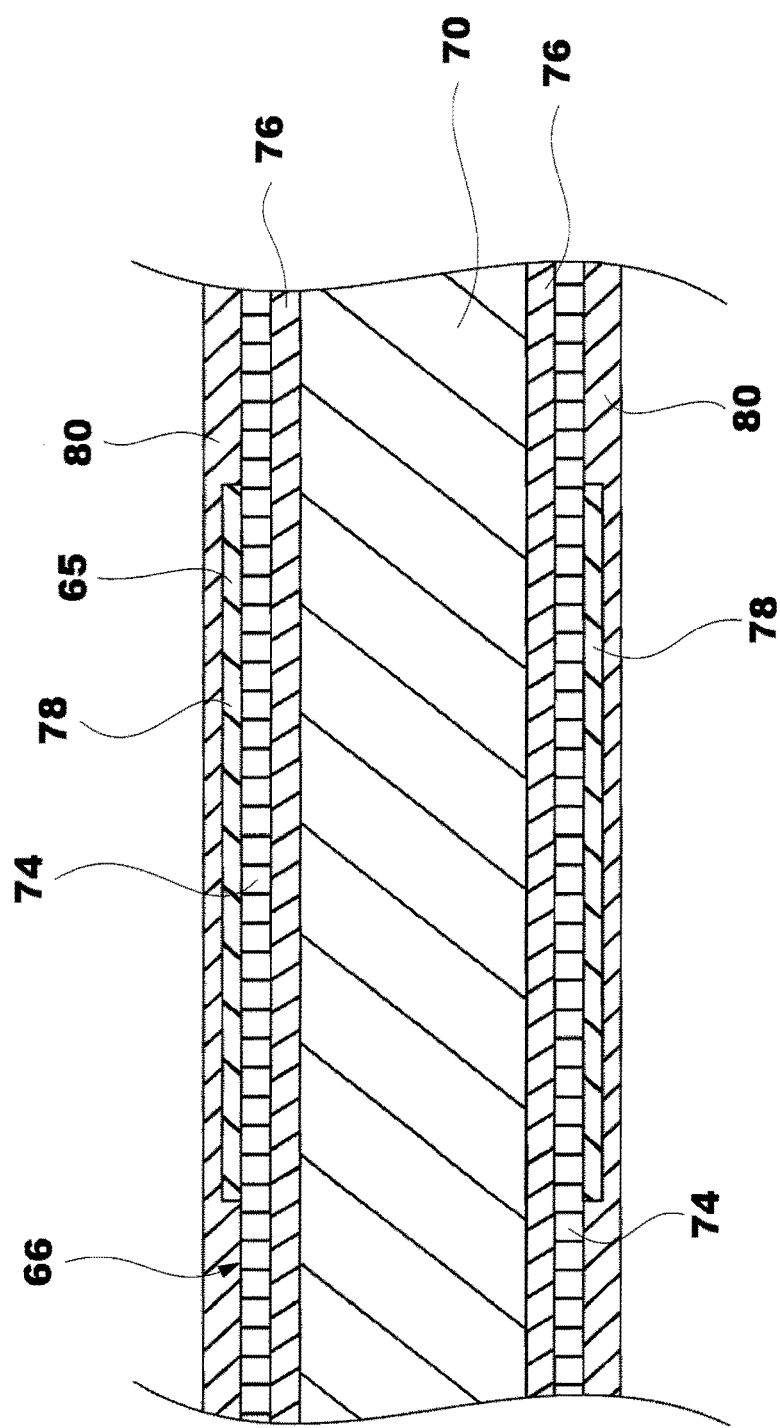
FIG. 1B shows a close-up cross-sectional view of a portion of another tip according to principles of the present invention.

Turning now to FIG. 1B, there is shown a close-up cross-sectional view of a portion of another surgical tip according to principles of the present invention. The tip in FIG. 1B is similar to the tip in FIG. 1A with the addition of a second intervening layer 76. The second intervening layer 76 may be a strike layer, such as nickel strike or gold flash, for facilitating plating of the first intervening layer 74 to the support. The second intervening layer 76 may be relatively thin, for example, about 1-2 µm. The second intervening layer 76 may provide for better attachment or bonding of the first intervening layer 74 to the support 70.

The second intervening layer 76 may have a coefficient of thermal expansion which provides a transition to accommodate any differences in the coefficient of thermal expansions between the support 70 and the ferromagnetic material 65 (typically a ferromagnetic coating 78), and any other intervening layers, such as the first intervening layer 74. It will be appreciated that taking into account the coefficients of thermal expansion of the different layers which may be used in constructing a surgical tip of the present invention may increase the durability of the surgical tip. It will also be appreciated that additional intervening layers, other than those shown, may be included to further provide for a more gradual transition of coefficients of thermal expansion between layers. For example, the conductor 66 may include a strike layer in addition to multiple intervening layers.

Figure 1C:
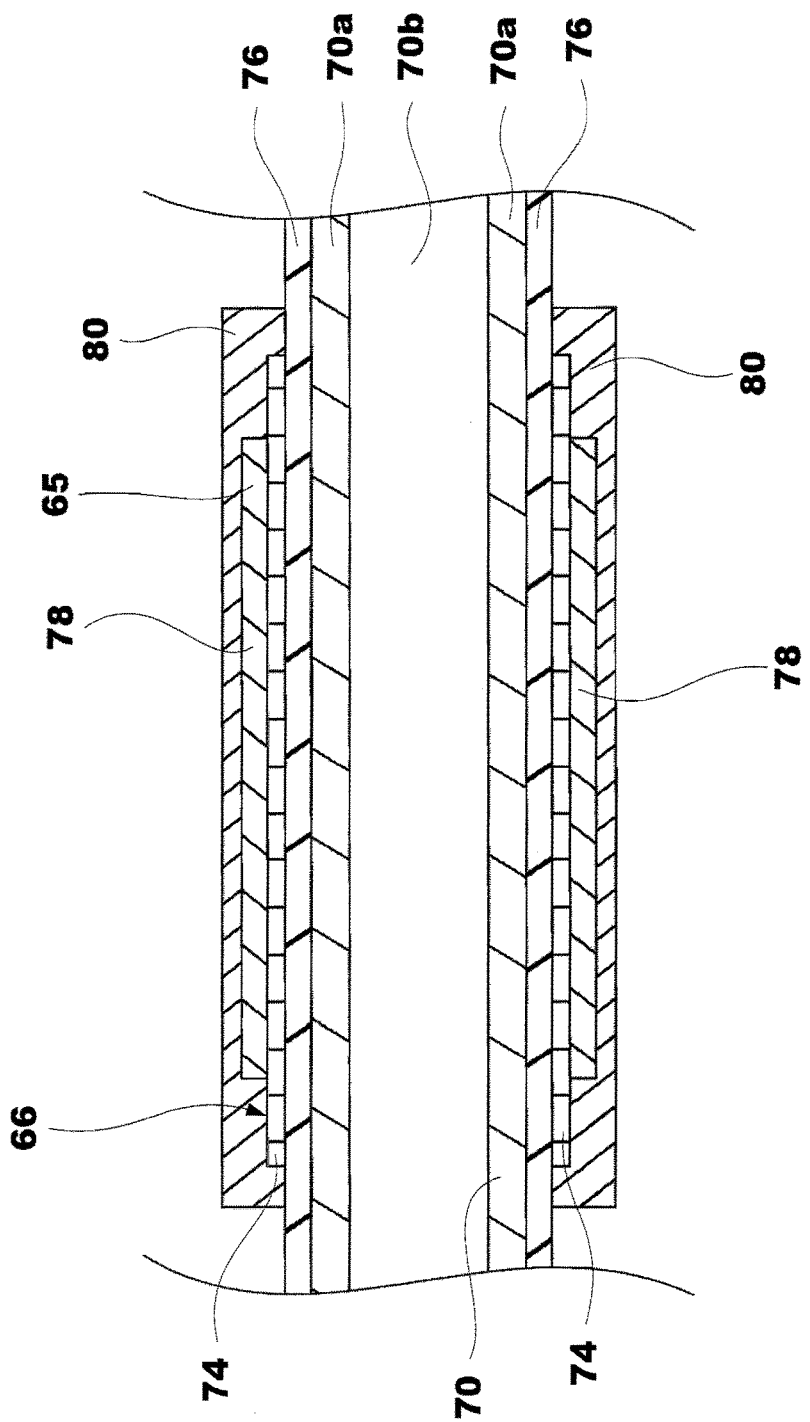
FIG. 1C shows a close-up cross-sectional view of a portion of another tip according to principles of the present invention.

Turning now to FIG. 1C, there is shown a close-up cross-sectional view of a portion of another surgical tip according to principles of the present invention. The surgical tip may comprise a conductor 66 having a support 70 that is tubular. Thus, in the cross-sectional view the wall 70a which circumscribes a void 70b of the support 70 can be seen. By using a tubular support 70 the amount of material comprising the support 70 is reduced. Thus, the heat capacity of the tubular support 70 will be reduced allowing the surgical tip to cool more rapidly. While the conductor 66 is shown as being generally linear, it will be appreciated that the conductor can be formed into a variety of shapes.

Figure 1D:
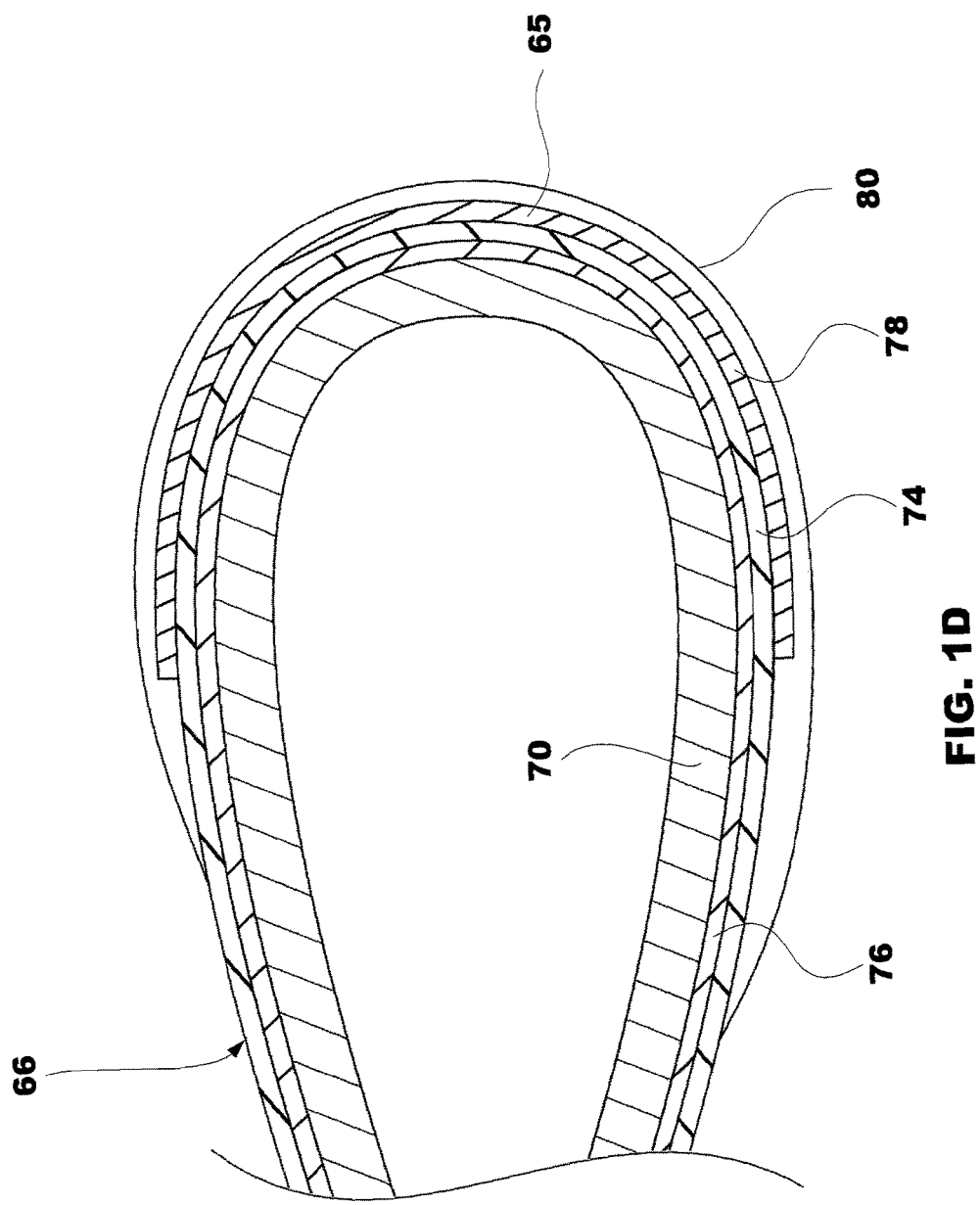
FIG. 1D shows a fragmented cross-sectional view of a tip having a loop geometry.

FIG. 1D shows a fragmented cross-sectional view of a portion of a surgical tip having loop geometry. As with the surgical tips shown in FIGS. 1A-1C, the surgical tip in FIG. 1D may include a conductor 66 having one or more intervening layers, a ferromagnetic material, and a biocompatible layer disposed thereon. (For ease of illustration the multiple layers are shown disposed on one side of the support 70, but it will be appreciated that one or more of the multiple layers shown may be circumferentially disposed on the support 70). The various layers which make up the surgical tip may be disposed on and extend along the support 70 at various lengths. For example, the second intervening layer 76 may substantially extend the entire length of the support 70. Likewise, the first intervening layer 74 (and/or any additional intervening layers) and a biocompatible layer 80 may substantially extend along the entire length of the support 70. In the alternative, the first intervening layer 74 and the biocompatible layer 80 may extend a short distance beyond the ferromagnetic material 65.

As discussed above, the ferromagnetic material 65 may be disposed along only a portion of the conductor 66 at a defined location (or locations) so as to provide for localized heating along the surgical tip only in an area(s) where heating is desired. The length of the ferromagnetic material may depend, in large part, on the desired use of the device.

The length at which each of the multiple layers is disposed along the substrate 70 may vary depending on the treatment for which the surgical tip formed by the conductor 66 is to be used. For example, in some situations, it may be desirable to have very localized heating in order to cause as little trauma to adjacent tissue as possible. Thus, if the surgical tip is trying to cut through a thin membrane without damaging tissue thereunder or conducting brain surgery, the ferromagnetic material may be half a centimeter or less in length to provide a very precise cutting region. In contrast, if the surgical tip is being used to cut through muscle, thicker tissue, or is being used as a loop to cut out and cauterize tissue, such as removing a large tumor, it may be desirable to have the ferromagnetic material be several centimeters long.

Turning now to FIG. 2, a perspective view of an alternate embodiment of a thermal surgical system 10 is shown. In FIG. 2, the power source 30 is contained within the foot pedal 20. Depending on the application and power required, the instrument may even be entirely battery powered for relatively low power applications. An alternate embodiment for low power requirements may include the battery, power adjustment and power delivery, all self-contained in the handle 51 of the handheld surgical tool 50. Furthermore, a wireless communication module can be employed to send and receive information from the handheld surgical tool 50, including status and control settings that would enable users to monitor system performance and alter power settings remotely from the handheld surgical tool 50 itself.

It is our understanding that this thermal solution may provide advantages over monopolar and bipolar electrical systems currently available because the thermal damage may remain very close to the ferromagnetic surface of the coated region, whereas monopolar and bipolar electrical tissue ablation may frequently cause tissue damage for a distance away from the point of contact. It is our understanding that this method may also overcome disadvantages of other thermal devices based upon resistive heating, which may require more time to heat and cool, and thus present greater patient risk, while potentially having higher voltage requirements at the point of heating.

Furthermore, the thin ferromagnetic portion 65, disposed along a small segment of the conductor, may reduce the heating of other non-target material in the body, such as blood when working within the heart in atrial ablation—which can lead to complications if a clot is formed. The small thermal mass of the conductor wire 66, the one or more intervening layers 74, 76, ferromagnetic coating 78 and exterior layer 80 (if any), as well as localization of the heating to a small region provided by the construction of the tool (i.e. ferromagnetic portion 65 and adjacent structures) provides a reduced thermal path for heat transfer in directions away from the location of the ferromagnetic portion 65. This reduced thermal path may result in the precise application of heat at only the point desired. As this technology alone does not employ a spark or an arc like monopolar or bipolar technology, risks of ignition, such as by anesthetic gasses within or around the patient by sparks, are also reduced.

The thermal surgical tool system 10 may be used for a variety of therapeutic means—including sealing, "cutting" or separating tissue, coagulation, or vaporization of tissue. In one configuration, the thermal surgical tool system 10 may be used like a knife or sealer, wherein the surgeon is actively "cutting" or sealing tissue by movement of the ferromagnetic portion 65 through tissue. The thermal action of the embodiments disclosed here may have distinct advantages including substantial reduction, if not elimination, of deep tissue effects compared with those associated with monopolar and bipolar RF energy devices.

In another configuration, the ferromagnetic coated conductor 60 may be inserted into a lesion and set to a specific power delivery or variable power delivery based on monitored temperature. The thermal effects on the lesion and surrounding tissue may be monitored until the desired thermal effect is achieved or undesired effects are noticed. One advantage of the application of the ferromagnetic coated conductor is that it may be cost-effective compared to microwave or thermal laser modalities and avoids the undesired tissue effects of microwave lesion destruction. Thus, for example, a surgeon can insert the ferromagnetic coated conductor into a tumor or other tissue to be destroyed and precisely control the tissue damage that is created by activating the handheld surgical tool 50.

Sensors may be used to monitor conditions of the handheld surgical tool 50 or the tissue, such as an infrared detector or sensor stem 12. For instance, the temperature of the device or tissue may be important in performing a procedure. A sensor in the form of a thermocouple, a junction of dissimilar metals, thermistor or other temperature sensor may detect the temperature at or near the ferromagnetic portion 65 or tissue. The sensor may be part of the device, such as a thermocouple placed as a part of the conductor or near the ferromagnetic coating, or separate from the handheld surgical tool 50, such as a separate tip placed near the tissue or ferromagnetic portion 65. The temperatures may also be correlated with tissue effects, seen in FIG. 27. Other useful conditions to monitor may include, but are not limited to, color, spectral absorption, spectral reflection, temperature range, water content, proximity, tissue type, transferred heat, tissue status, impedance, resistance, voltage and visual feedback (i.e. a camera, fiberoptic or other visualization device).

The handheld surgical tool 50 may be configured for repeat sterilization or single patient uses. More complex devices may be useful for repeat sterilization, while more simple devices may be more useful for single patient use.

A method for treating or cutting tissue may include the steps of: selecting a surgical tool having a cutting edge and a conductor disposed adjacent the cutting edge, at least a portion of which is coated with a ferromagnetic material; cutting tissue with the cutting edge; and applying oscillating electrical energy to the conductor to heat the ferromagnetic material and thereby treating the cut tissue.

Optional steps of the method may include the steps of: causing hemostasis within the cut tissue; using the heated ferromagnetic material to incise tissue; or using the heated ferromagnetic material to cause vascular endothelial welding.

Referring now to FIG. 3, a diagram of an embodiment of the adjustable thermal surgical tool system 10 is shown. The power delivery to the ferromagnetic portion 65 is controlled by a modulated high frequency waveform. The modulated waveform allows power delivery to be controlled in a manner that adjustably modifies, allows or blocks portions of the waveform based on the desired power delivery.

In FIG. 3, an initial waveform 110 is passed through a modulator 120 receiving commands from a foot pedal 20. The waveform is created by an oscillator 130 to the desired frequency, and modulated by the modulator 120, which may include, but is not limited to, one or more of amplitude, frequency or duty cycle modulation, including a combination thereof. The resultant signal is then amplified by an amplifier 140. The amplified signal is sent across a tuned cable 150, meaning that the cable is tuned to provide a standing wave with maximum current and minimum voltage at the location of the ferromagnetic portion 65 of the handheld surgical tool 50. Alternatively, the cable 150 may not be tuned, but a circuit may be placed in the handle 51 to impedance match the ferromagnetic coated conductor 60 as a load to the power source 30.

The thermal surgical tool system 10 may be tuned by specifying the location of the ferromagnetic portion 65 with respect to the amplifier 140 (such as cable length) and tuning the high frequency signal to approximately a resonant standing wave such that current is maximized at the location of the ferromagnetic portion 65.

It should be recognized that the surgical tool may operate in a dynamic environment. Thus when used herein, approximately a standing wave means that a circuit may be tuned such that the signal may be near an optimal standing wave but may not achieve it, may only achieve the wave for small amounts of time, or may successfully achieve a standing wave for longer periods of time. Similarly, any use of "standing wave" without the modifier of approximate should be understood to be approximate in the context of the thermal surgical tool.

One method for achieving such current maximization is to connect the ferromagnetic coated conductor 60 to a cable 150 that is an odd multiple of one-quarter wavelengths in length and connected to the output of the amplifier 140. The design of the circuit having a resonant standing wave is intended to optimize power delivery to the ferromagnetic coating. However, in one embodiment, the power source 30 could be positioned at the location of (or closely adjacent to) the ferromagnetic portion 65, and tuning could be achieved with electrical components, all within a single handheld, battery-powered instrument. Alternatively, electrical components necessary for impedance matching can be located at the output stage of the amplifier 140. Further, electrical components, such as a capacitor or inductor, can be connected in parallel or series to the ferromagnetic coated conductor 60 at the location of the connection of the conductor wire 66 to the cable 150, in order to complete a resonant circuit.

Dynamic load issues can be caused by the interaction of the ferromagnetic coated conductor 60 with various tissues. These issues may be minimized by the standing current wave being maximized at the load location. Multiple different frequencies can be used, including frequencies from 5 megahertz to 24 gigahertz, preferably between 40 MHz and 928 MHz. In some regulated countries it may be preferable choose frequencies in the ISM bands such as bands with the center frequencies of 6.78 MHz, 13.56 MHz, 27.12 MHz, 40.68 MHz, 433.92 MHz, 915 MHz, 2.45 GHz, 5.80 GHz, 24.125 GHz, 61.25 GHz, 122.5 GHz, 245 GHz. In one embodiment, the oscillator 130 uses an ISM Band frequency of 40.68 MHz, a class E amplifier 140, and a length of coaxial cable 150, all of which may be optimized for power delivery to a ferromagnetic coated tungsten conductor 60 with a ferromagnetic portion 65 consisting of a thickness of between 0.05 micrometer and 500 micrometers, and preferably between 1 micrometer and 50 micrometers. A useful estimate may be to start the ferromagnetic coating thickness at 10% of the conductor diameter, and up to 5 cm long. However, the ferromagnetic coating may be disposed as far along the length or along multiple regions of the conductor as where heating may be desired. (The ferromagnetic portion 65 may be formed from a Nickel Iron (NiFe) alloy, such as NIRON™ from Enthone, Inc. of West Haven, Conn., or other ferromagnetic coatings, including, but not limited to Co, Fe, $FeOFe_2O_3$, $NiOFe_2O_3$, $CuOFe_2O_3$, $MgOFe_2O_3$, MnBi, Ni, MnSb, $MnOFe_2O_3$, $Y_3Fe_5O_{12}$, $CrO_2$, MnAs, Gd, Dy, EuO, magnetite, yttrium iron garnet, aluminum, PERMALLOY™, zinc, etc.)

The size of the conductor (which may include a support having one or more intervening layers disposed thereon), size of the ferromagnetic coating, associated thicknesses, shape, primary geometry, composition, power supply and other attributes may be selected based on the type of procedure and surgeon preferences. For example, a brain surgeon may desire a small instrument in light handheld package designed for quick application within the brain, while an orthopedic surgeon may require a larger device with more available power for operation on muscle.

The conductor may be comprised of one or more metals, wherein connection of two dissimilar metals may form a thermocouple. If the thermocouple were placed in the vicinity of or within of the ferromagnetic coating, the thermocouple may provide a temperature feedback mechanism for the device. Further, some conductors, or parts of the conductor, may have a resistivity that correlates to temperature, which may also be used to measure temperature.

The tuning of the power source 30 also reduces the amount of high frequency energy radiating into the patient to near zero, as voltage is low, and ideally zero, at the location of the ferromagnetic portion 65. This is in contrast to monopolar devices, which require a grounding pad to be applied to the patient, or bipolar devices, both of which pass current through the tissue itself. The disadvantages of these effects are well known in the literature.

In many of these embodiments discussed herein, the combination of cable length, frequency, capacitance and inductance may also be used to adjust efficiency and tool geometry by tuning the power source 30 to deliver maximum power to the ferromagnetic portion 65, and therefore, maximum heat to the tissue. A tuned system also provides for inherent safety benefits; if the conductor were to be damaged, the system would become detuned, causing the power delivery efficiency to drop, and may even shut down if monitored by an appropriate safety circuit.

The amount of power delivered to the patient tissue may be modified by several means to provide precise control of tissue effects. The power source 30 may incorporate a modulator 120 for power delivery as described above. Another embodiment uses modification of the magnetic field by altering the geometry of the conductor wire 66 and the ferromagnetic portion 65 through which it passes, such as would be caused by a magnet. Placement of the magnet nearby the ferromagnetic portion 65 would similarly alter the induction effect and thereby change the thermal effect.

While modulation has been discussed as a method to control power delivery, other methods may be used to control power delivery. In one embodiment, the output power, and correspondingly the temperature, of the tool is controlled by tuning or detuning the drive circuit, including the conductor wire 66 and ferromagnetic coated conductor 60.

Figure 4A:
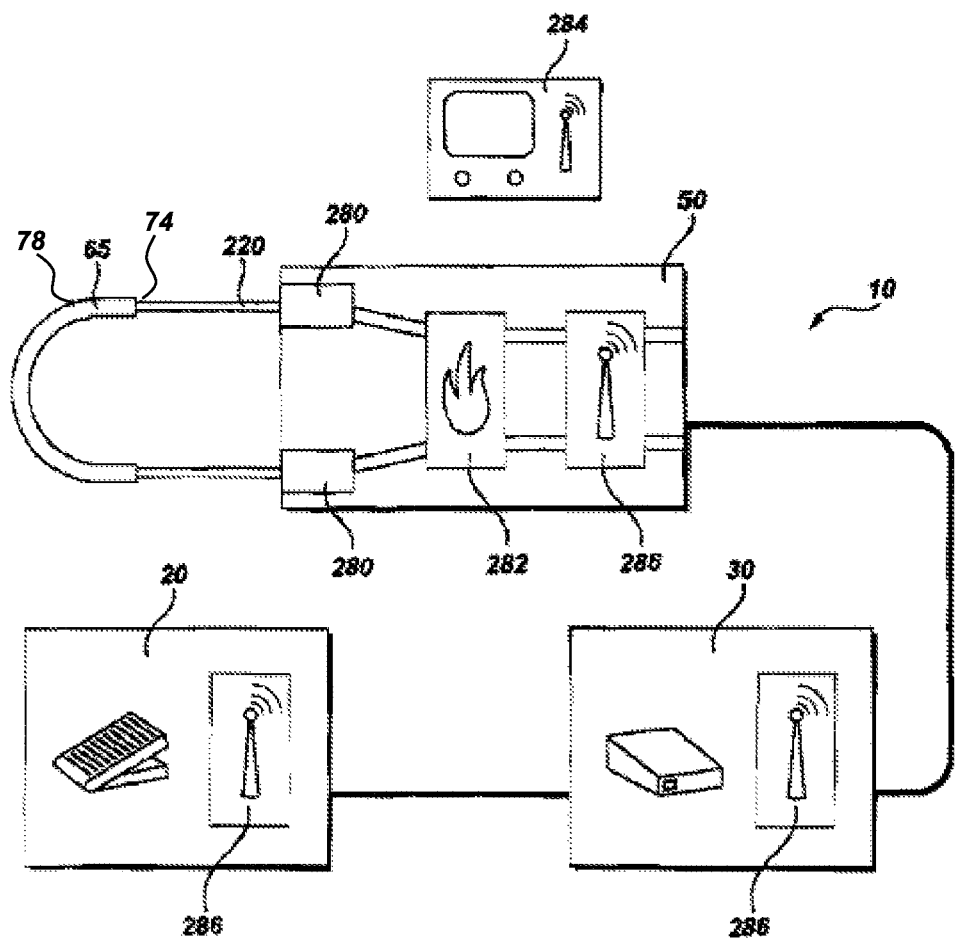
FIG. 4A shows a thermal surgical tool system with heat prevention terminals, heat sink, and wireless communication devices.

Turning now to FIG. 4A, a thermal surgical tool system 10 with connectors which attach to opposing first and second ends of a conductor is shown. (It will be appreciated that the conductor may be a wire conductor or other configuration as discussed herein). The conductors as shown in FIG. 4A may be formed by heat prevention terminals 280, such as crimp connectors that provide thermal isolation. One or more heat sinks 282, and wireless communication devices 286 may also be included. The conductor 220 may be connected to the handheld surgical tool 50 by terminals 280 and/or a heat sink 282 at opposing first and second ends of the conductor. Portions of the conductor may extend into the handle into terminals, while the ferromagnetic coating portion of the conductor may extend beyond the handle. The terminals 280 may have a poor thermal conductance such that the terminals 280 reduce the heat transfer from the conductor into the handheld surgical tool 50. In contrast, the heat sink 282 may draw any residual heat from the terminals 280 and dissipate the heat into other mediums, including the air. Connectors and connections may also be achieved by wire bonding, spot and other welding, in addition to crimping.

Preventing thermal spread may be desirable because the other heated portions of the handheld surgical tool 50 may cause undesired burns, even to the operator of the handheld surgical tool 50. In one embodiment, terminals 280 are used to conduct the electric current, but prevent or reduce thermal conduction beyond the ferromagnetic coated conductor.

The thermal surgical tool may also communicate wirelessly. In one embodiment, the user interface for monitoring and adjusting power levels may be housed in a remote, wirelessly coupled device 284. The wirelessly coupled device may communicate with a wireless module 286 contained within the thermal surgical tool system 10, including the handheld surgical tool 50, the control system (such as footpedal 20), and/or the power subsystem 30. By housing the control interface and display in a separate device, the cost of the handheld surgical tool 50 portion may be decreased. Similarly, the external device may be equipped with more processing power, storage and, consequently, better control and data analysis algorithms.

Figure 4B:
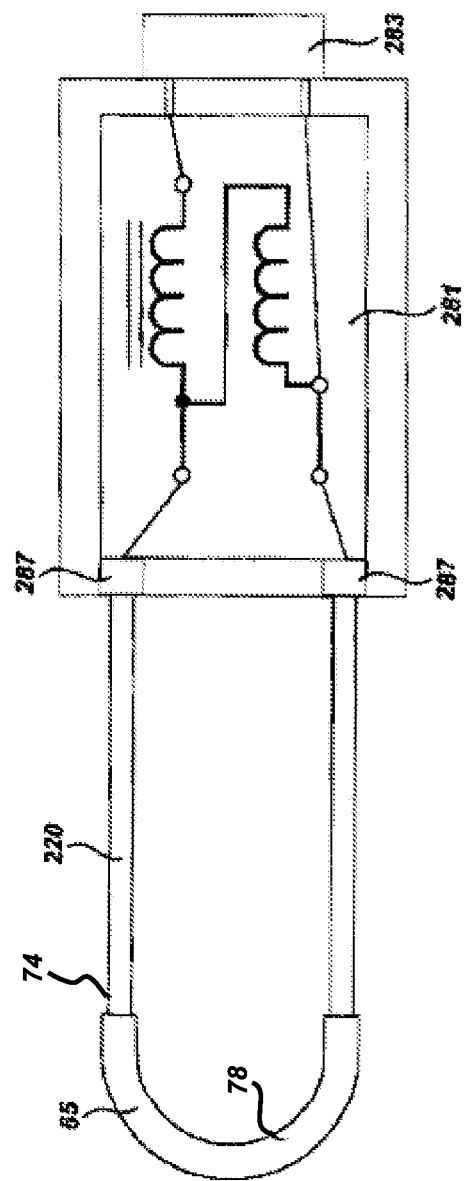
FIG. 4B shows a portion of a thermal surgical tool system with an impedance matching network.

Turning now to FIG. 4B, a thermal surgical tool system with impedance matching network is shown. The impedance matching network may match the output impedance of the signal source to the input impedance of the load. This impedance matching may aid in maximizing power and minimizing reflections from the load.

In one embodiment, the impedance matching network may be a balun 281. This may aid in power transfer as the balun 281 may match the impedance of the ferromagnetic coated conductor terminals 287 to the amplifier cable terminals 283 (shown here as a coaxial cable connection). In such a configuration, some baluns may be able to act as a heat sink and provide thermal isolation to prevent thermal spread from the thermal energy at the ferromagnetic portion 65 transferred by the conductor 220 to terminals 287. The appropriate matching circuitry may also be placed on a ceramic substrate to further sink heat away or isolate heat away from the rest of the system, depending on the composition of the substrate.

It should be recognized that these elements discussed in FIGS. 4A and 4B can be used in conjunction with any of the embodiments shown herein.

Figure 4C:
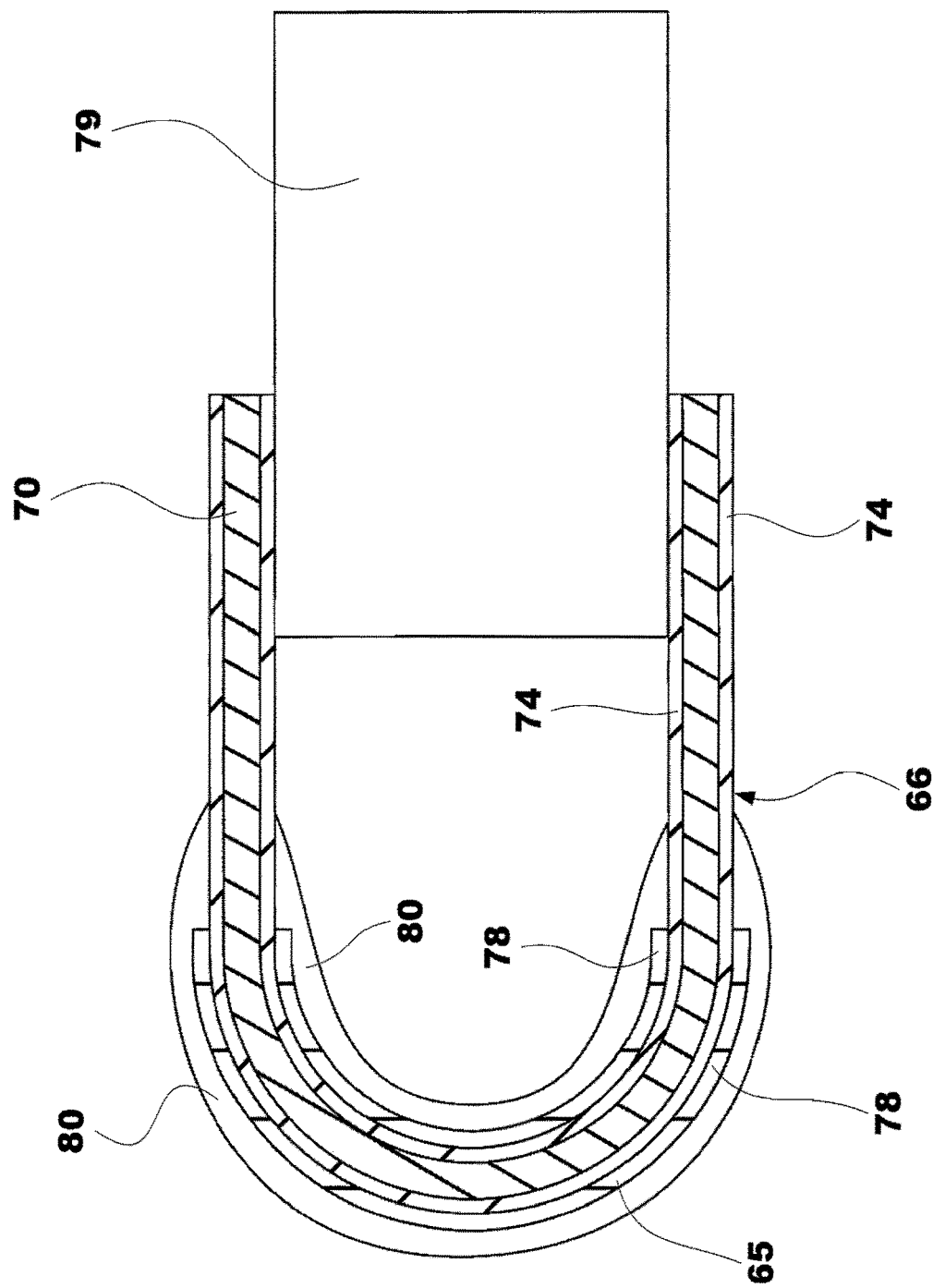
FIG. 4C shows a side cross-sectional view of a portion of a thermal surgical tool system according to principles of the present invention.

Turning now to FIG. 4C, there is shown a portion of a thermal surgical tool system according to principles of the present invention. The thermal surgical tool system may include a conductor 66 comprising a support 70 and one or more intervening layers 74 (including a strike layer 76 shown in FIG. 1B), a ferromagnetic portion 65 (typically formed by a ferromagnetic layer 78), and a biocompatible layer 80. The conductor 66 of the thermal surgical tool system may be attached to a printed circuit board 79. Depending on the material used as the support 70, attachment of the conductor to the printed circuit board 79 may be facilitated by conductively connecting the conductor to the printed circuit board 79 via the intervening layer 74. For example, an intervening layer 74 comprised of copper may be more readily attachable to the printed circuit board 79 than a support comprised of tungsten. Additionally, the support 70 could be attached mechanically and have an intervening layer to connect the conductor 66 to the printed circuit board electrically.

Alternatively, a sleeve 75 may be disposed on the support 70 to facilitate attachment of the conductor 66 to the printed circuit board 79 as is shown in FIG. 4D. The sleeve 75 may be attached to the support 70, for example by TIG welding the sleeve 75 to the support 70. The sleeve 75 may be disposed on the support 70 such that the sleeve 75 is in contact with or connected to the intervening layer 74, as indicated by location 71, so that electrical energy may be transferred from the sleeve 75 to the intervening layer 74 and thereby cause heating of the ferromagnetic portion 65. Thus, in contrast to the intervening layer 74 shown in FIG. 4C, the intervening layer 74 shown in FIG. 4D does not extend along the entire length of the support.

Figure 5:
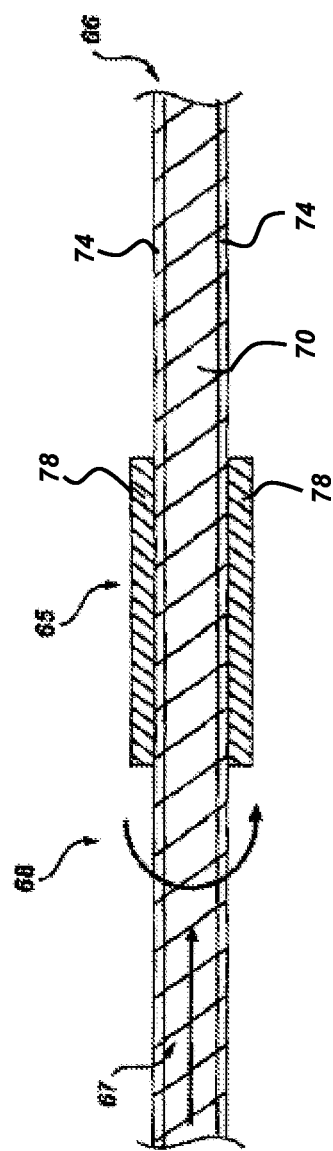
FIG. 5 shows a close-up, side cross-sectional view of a single layer ferromagnetic coated conductor tip in accordance with one aspect of the present invention.

Turning now to FIG. 5, a longitudinal cross section of a ferromagnetic coated conductor according to principles of the present invention is shown. As an alternating current 67 is passed through conductor 66, a time varying magnetic field 68 is induced around conductor 66. According to one aspect of the invention, a majority of the alternating current may travel through one or more conductive layers 74 and, in some embodiments, a strike layer as described in more detail above. The time varying magnetic field 68 is resisted by the ferromagnetic portion 65, causing the ferromagnetic coating 78 to dissipate the inductive resistance to the time varying magnetic field 68 as heat. Should the ferromagnetic coating 78 reach it's Curie point, the magnetic resistive properties of ferromagnetic coating 78 become substantially reduced, resulting in substantially decreased resistance to time varying magnetic field 68. As there is very little mass to the ferromagnetic coating 78, the magnetic field causes the ferromagnetic portion 65 to quickly heat. Similarly, the ferromagnetic coating 78 is small in mass compared to conductor wire 66 and therefore heat will quickly dissipate therefrom due to thermal transfer from the hot ferromagnetic coating 78 to the cooler and larger conductor 66 and other structures, as well as from the ferromagnetic coating 78 to the surrounding environment.

It should be appreciated that while the figures show a solid circular cross-section, the conductor cross-section may have various geometries. For instance, the conductor may be a hollow tubing such that it reduces thermal mass as is shown in FIG. 1C. Whether solid or hollow, the conductor may also be shaped such that it has an oval, triangular, square or rectangular cross-section.

As is also evident from FIG. 5, the ferromagnetic coating may be between a first section (or proximal portion) and a second section (or distal portion) of the conductor. This may provide the advantage of limiting the active heating to a small area, instead of the entire conductor. A power supply may also connect to the conductor 66 via the first and second section to include the ferromagnetic coating within a circuit providing power.

A method of forming the surgical tool may include the steps of: selecting a conductor and plating a ferromagnetic coating upon the conductor, or plating one or more intervening layers and then plating the ferromagnetic coating on one of the intervening layers as was discussed above.

Optional steps to the method may include: selecting a size of a conductor having a ferromagnetic coating disposed on a portion thereof according to a desired procedure; selecting a thermal mass of a conductor having a ferromagnetic coating disposed on a portion thereof according to a desired procedure; selecting a conductor from the group of loop, solid loop, square, pointed, hook and angled; configuring the oscillating electrical signal to heat the coating to between 37 and 600 degrees Centigrade; configuring the oscillating electrical signal to heat the coating to between 40 and 500 degrees Centigrade; causing the coating to heat to between about 58-62 degrees Centigrade to cause vascular endothelial welding; causing the coating to heat to between about 70-80 degrees Centigrade to promote tissue hemostasis; causing the coating to heat to between about 80-200 degrees Centigrade to promote tissue searing and sealing; causing the coating to heat to between about 200-400 degrees Centigrade to create tissue incisions; or causing the coating to heat to between about 400-500 degrees Centigrade to cause tissue ablation and vaporization. Treatment may include incising tissue, causing hemostasis, ablating tissue, or vascular endothelial welding.

While several of the previous figures have shown the coating around a generally straight conductor, it will be appreciated that the conductor and the ferromagnetic coating can be configured in a wide variety of shapes. These may include, for example, loops, hooks, snares, and a variety of other shapes may be used.

Figure 6:
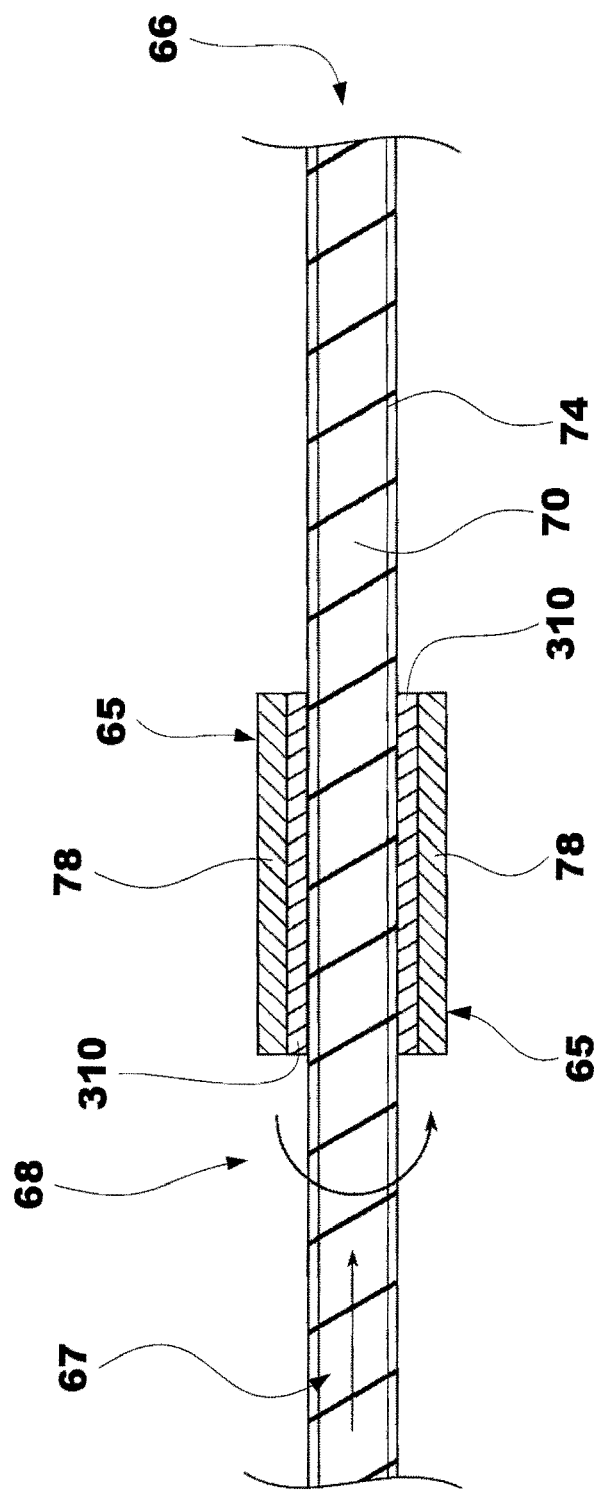
FIG. 6 shows a close-up, side cross-sectional view of a single layer ferromagnetic coated conductor tip with a thermal insulator in accordance with one aspect of the present invention.

Turning now to FIG. 6, a close-up, longitudinal cross-sectional view of a conductor 66 with a thermal insulator 310 is shown. A layer of thermal insulator 310 may be placed between the ferromagnetic coating 78 and the conductor wire 66. Putting a layer of thermal insulator 310 may aid in the quick heating and cool-down (also known as thermal response time) of the tool by reducing the thermal mass by limiting the heat transfer to the conductor wire 66. (It will be appreciated that a surgical tip of the present invention may include a non-conductive or conductive support 70, one or more conductive intervening layer 74 (which may include a strike layer 76 shown in FIG. 1B), an insulative intervening layer 310, the ferromagnetic coating 78, and/or a biocompatible layer (not shown)).

The thickness and composition of the thermal insulator may be adjusted to change the power delivery and thermal response time characteristics to a desired application. A thicker coating of thermal insulator 310 may better insulate the conductor 66 from the ferromagnetic coating 78, but may require increased power compared with a thinner coating of thermal insulator 310 in order to induce a magnetic field sufficient to cause the ferromagnetic coating to heat.

In the embodiments shown in FIGS. 7A-7G a plurality of surgical tips 210a-210g are shown in which the surgical tip has a conductor 220 and a ferromagnetic portion 65 which may be formed by relatively thin layer of ferromagnetic coating 78. The conductor 220 of the surgical tip 210 may include a non-conductive or conductive support, one or more conductive intervening layers (which may include a strike layer), and/or a biocompatible layer (which are shown in FIGS. 1A-1B above). Thus, conductor 220 may be substantially the same as conductor 66 as discussed above. As shown in FIGS. 7A-7G, the ferromagnetic coating 78 (or a layer forming the ferromagnetic portion 65) may be a circumferential coating around a conductor 220. When the conductor 220 is excited by a high frequency oscillator, the ferromagnetic coating 78 will heat according to the power delivered, via induction or other means with a limitation being provided in some configurations by its Curie temperature. Because of the small thickness of ferromagnetic coating 78 and the tuned efficiency of high frequency electrical conduction of the wire at the position of the ferromagnetic layer or coating 78, the ferromagnetic portion 65 will heat very quickly (i.e. a small fraction of a second) when the current is directed through the conductor 220, and cool down quickly (i.e. a fraction of a second) when the current is stopped.

Turning now to FIGS. 7A, 7B, 7C, 7D, 7E, 7F and 7G specifically, ferromagnetic coated conductor surgical tips 210a, 210b, 210c, 210d, 210e, 210f and 210g are shown. In each of these embodiments, a portion of conductor 220 (which may be formed similar to conductor 66 discussed above) is bent or formed and coated with a ferromagnetic portion 65 (typically a coating) such that the ferromagnetic coating 78 is only exposed to tissue (or covered with an outer layer) where the desired heating is to occur. FIGS. 7A and 7B are loop shapes that can be used for tissue cutting or excision, depending upon the orientation of the tool to the tissue. FIG. 7A shows a rounded geometry, while FIG. 7B shows a squared geometry. FIG. 7C shows a pointed geometry for heated tip applications that can be made very small because the process of tissue dissection, ablation, and hemostasis requires only a small contact point. FIG. 7D shows an asymmetric tool with a loop geometry, where the ferromagnetic coating 78 is only disposed on one side of the tool. FIG. 7E shows a hook geometry where the ferromagnetic coating 78 is disposed on the concave portion of the hook. FIG. 7F shows a hook geometry where the ferromagnetic coating 78 is disposed on the convex portion of the hook. FIG. 7G shows an angled geometry, which may be used in similar situations as a scalpel. Use of these various geometries of ferromagnetic coating 78 upon a conductor 220 may allow the surgical tip to act very precisely when active and to be atraumatic when non-active.

In one representative embodiment, the electrical conductor may have a diameter of 0.01 millimeter to 1 millimeter and preferably 0.125 to 0.5 millimeters, and a similar sized support can be used and coated with a thin layer of conductor. The electrical conductor or coating on the support may be tungsten, copper, other metals and conductive non-metals, or a combination such as two dissimilar metals joined to also form a thermocouple for temperature measurement. The electrical conductor may also be a thin coating of conductor, such as copper, dispersed around a non-metallic rod, fiber or tube, such as glass or high-temperature plastic or other materials having desired firmness/flexibility and heat dissipation characteristics. The conductive material, in-turn, may be coated with a thin layer of ferromagnetic material. The magnetic film forms a closed magnetic path around the electrically conductive wire. The thin magnetic film may have a thickness about 0.01-50% and preferably about 0.1% to 20% of the cross-sectional diameter of the wire. Due to the close proximity of the coating to the wire, a small current can produce high magnetic fields in the coating and result in significant temperatures. Since the magnetic permeability of this film is high and it is tightly coupled to the electrical conductor, low levels of current can result in significant hysteresis losses.

It is therefore possible to operate at high frequencies with low alternating current levels to achieve rapid inductive heating up to the Curie point. The same minimal thermal mass allows rapid decay of heat into tissue and/or the conductor with cessation of current. The tool, having low thermal mass, provides a rapid means for temperature regulation across a therapeutic range between about 37 degrees Celsius and 600 degrees Celsius, and preferably between 40 and 500 degrees Celsius.

While Curie point has been previously described as a temperature cap, instead, a material with a Curie point beyond the anticipated therapeutic need may be selected and the temperature can be regulated below the Curie point.

While some tip geometries are shown in FIGS. 7A through 7G, it is anticipated that multiple different geometries of the ferromagnetic coated conductor 66 or 220 may be used.

Figure 8:
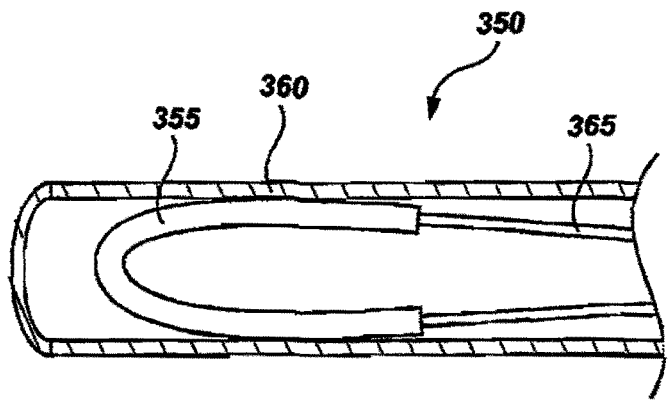
FIG. 8 shows a cut-away view of a retracted snare.

Turning now to FIG. 8, a cut-away view of a snare 350 in a retracted position is orientation is shown. A ferromagnetic coating 355 is placed on a conductor which is formed as a snare and then placed within a sheath 360. It will be appreciated that the conductor 365 may be a solid conductor, a hollow conductor or a conductor coated support as discussed above. Additionally, the ferromagnetic coating 355 may be exposed, or may be covered by a biocompatible material.

While retracted, the snare loop 350 may rest within a sheath 360 (or some other applicator, including a tube, ring or other geometry designed to reduce the width of the snare when retracted). The sheath 360 compresses the snare loop 350 within its hollow body. The sheath 360 may then be inserted into a cavity where the target tissue may be present. Once the sheath 360 reaches the desired location, the snare loop 350 may be extended outside the sheath 360, and end up deployed similar to FIG. 9A. In one embodiment, the conductor 365 may pushed or pulled to cause extension and retraction of the snare loop 355.

Figure 9A:
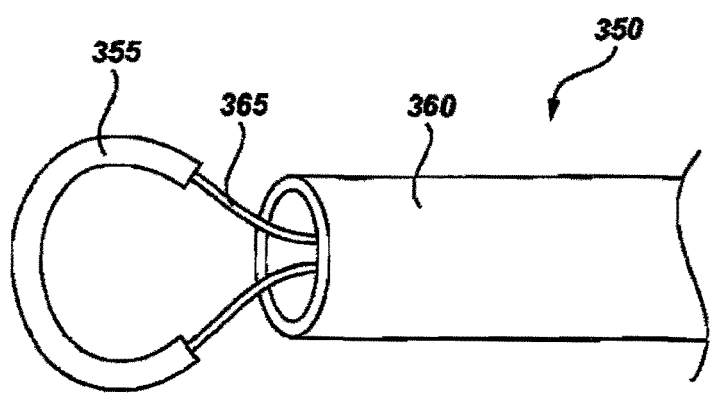
FIG. 9A shows a side view of an extended snare.

Turning now to FIG. 9A a side views of a snare 350 in an extended position is shown. The conductor 365 of the snare 350 may comprise a non-conductive or conductive support, one or more conductive intervening layers 74 (including a strike layer), and/or a biocompatible layer (as shown in FIGS. 1A-1D above). It is desirable that the conductor 365 of the snare 350 be made from a material that is relatively flexible and can "spring" into the loop shape when deployed from the sheath 360. Additionally, the material used as the conductor 365 should have a sufficiently high annealing temperature as it may be subjected to high temperature during normal operation of the snare 350. Thus, suitable materials which may be used as the conductor 365, or one or more layers of the conductor 365, include, but are not limited to, Nichrome alloys or Haynes alloys.

Once extended, the snare 350 loop may be used in several different ways. In one embodiment, the snare loop 350 may be placed substantially around the target tissue, such that the tissue is within the snare loop 350. The ferromagnetic coating 355 may then be caused to be inductively heated (and/or heated by skin effect and/or eddy currents) as discussed above. The snare loop 350 is then retracted back into the sheath 360 such that the target tissue is separated and removed from tissue adjacent the target tissue. The desired temperature range or power level may be selected for hemostasis, increased tissue separation effectiveness or other desired setting. For example, in one embodiment, the snare 350 is configured for nasal cavity polyp removal.

In another use, the snare 350 may be configured for tissue destruction. Once within the desired cavity, the snare may be extended such that a portion of the snare loop 350 touches the target tissue. The snare loop 350 may then be inductively heated such that a desired tissue effect occurs. For example, in one embodiment, the sheath may be placed near or in the heart and the snare loop 350 inductively heated to cause an interruption of abnormal areas of conduction in the heart, such as in atrial ablation.

Figure 9B:
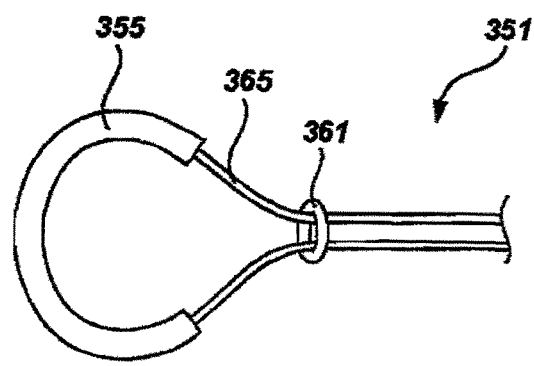
FIG. 9B shows an alternate embodiment of an extended snare.

Turning now to FIG. 9B, an alternate embodiment of a snare 351 is shown. The applicator may be a ring 361 instead of a sheath as in FIG. 9A. Similar to the sheath, the ring 361 may be used to force the loop into an elongated position.

Various devices could be used to hold the ring in place during use. As with the previous configurations, the conductor 365 could be a solid conductor, or could be a conductive covered support. Likewise, the ferromagnetic material may be exposed or covered by a biocompatible material depending on the particular situation.

A method of separating tissue may include the steps of: selecting a conductor having a ferromagnetic coating disposed on a portion thereof; placing the portion of the conductor having the ferromagnetic coating within a tube; inserting the tube into a cavity; deploying the portion of the conductor having the ferromagnetic coating within the cavity; and delivering an oscillating electrical signal to the conductor so as to heat the ferromagnetic coating while the heated ferromagnetic coating is in contact with a target tissue.

Optional steps may include: deploying step further comprises placing the ferromagnetic coating substantially around the target tissue; retracting the ferromagnetic coating portion of the conductor into the tube; causing hemostasis in the target tissue; forming the conductor into a bent geometry such that a portion of the conductor remains within the tube; and touching a ferromagnetic covered portion of the bent geometry to the target tissue.

A method of removing tissue may include the steps of: selecting a conductor having at least one portion having a ferromagnetic conductor disposed thereon; and placing the ferromagnetic conductor around at least a portion of the tissue and pulling the ferromagnetic conductor into contact with the tissue so that the ferromagnetic conductor cuts the tissue.

Optional steps may include: using a conductor having a plurality of ferromagnetic conductors in an array or passing an oscillating electrical signal through the conductor while the ferromagnetic material is in contact with the tissue.

Figure 10A:
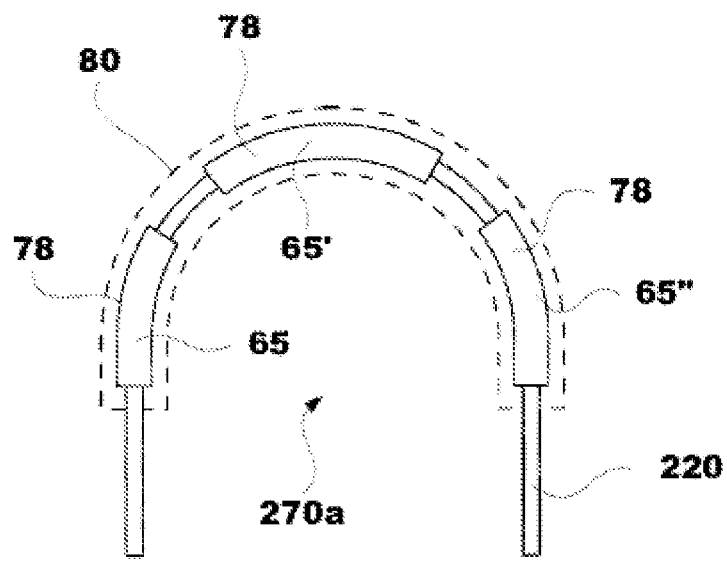
FIG. 10A shows a close-up view of a ferromagnetic coated conductor surgical tool with a loop geometry and linear array of coatings.

Turning now to FIG. 10A, a close-up view of a cutting tip with a loop geometry and linear array of coatings is shown. While the above embodiments have disclosed a continuous ferromagnetic coating on a conductor, in another embodiment, there is more than one coating separated by gaps on a single conductor. This is termed a linear array of ferromagnetic elements (an example of a parallel array of ferromagnetic elements can be seen in FIGS. 18A-18C).

In one embodiment, a loop geometry 270a may have multiple ferromagnetic portions 65, 65', and 65" which are separated by gaps on a conductor 220 (which may be formed as conductor 66 discussed above). If desired, the ferromagnetic portions formed by the ferromagnetic layers or coatings 78 may be covered with a biocompatible material, etc.

Figure 10B:
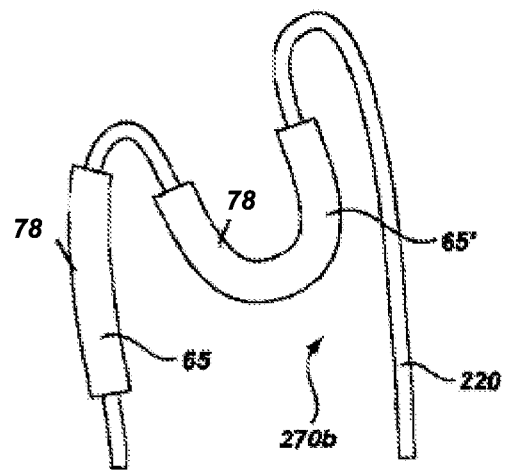
FIG. 10B shows a close up view of a ferromagnetic coated conductor surgical tool with an alternate hook geometry and linear array.

In another embodiment shown in FIG. 10B, a close up view of a cutting tip with an alternate hook geometry 270b and linear array of ferromagnetic portions 65 and 65' is shown on a conductor 220. The linear array may include the advantage of allowing flexibility in building a desired thermal geometry.

The conductor 220 which may be formed of an alloy having shape memory, such as Nitinol (nickel titanium alloy). A Nitinol or other shape memory alloy conductor can be bent into one shape at one temperature, and then return to its original shape when heated above its transformation temperature. Thus, a physician could deform it for a particular use at a lower temperature and then use the ferromagnetic coating to heat the conductor to return it to its original configuration. For example, a shape memory alloy conductor could be used to form a snare which changes shape when heated. Likewise, a serpentine shape conductor can be made of Nitinol or other shape memory alloy to have one shape during use at a given temperature and a second shape at a higher temperature. Another example would be for a conductor which would change shape when heated to expel itself from a catheter or endoscope, and then enable retraction when cooled.

In another embodiment, the ferromagnetic portions may be formed in such a way that an individual coating among the linear array may receive more power by tuning the oscillating electrical energy. The tuning may be accomplished by adjusting the frequency and/or load matching performed by the power source to specific ferromagnetic coatings.

Figure 11:
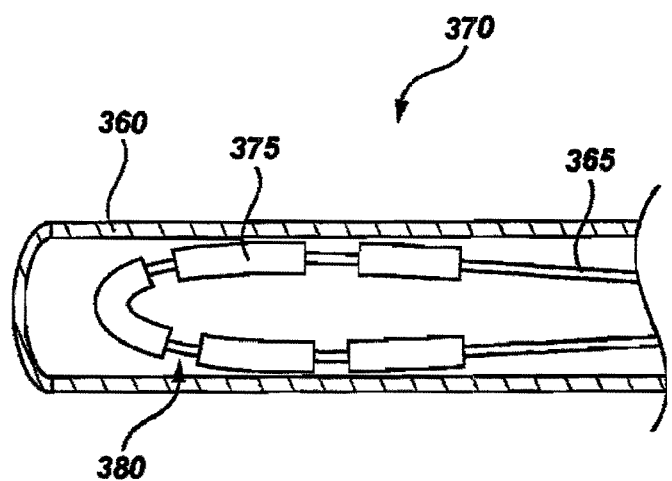
FIG. 11 shows a cut-away view of a retracted snare with an array of coatings.

Turning now to FIG. 11, a cut-away view of a snare tool 370 with a linear array of coatings in a retracted position is shown. In some embodiments, some ferromagnetic portions may lack the elasticity to effectively bend into a retracted position. Therefore, individual ferromagnetic segments 375 may be separated by gaps 380 such that the conductor 365 may be flexed while the ferromagnetic segments 375 may remain rigid. For example, a number of small segments of ferromagnetic material may be used and then covered with a more flexible outer layer which would convey the heat to the tissue to be treated.

Figure 12:
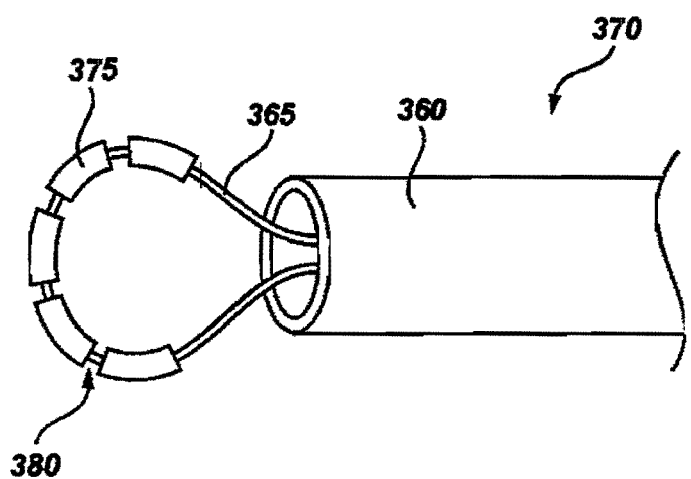
FIG. 12 shows a side view of an extended snare with an array of coatings.

Similarly, the snare tool 370 may be extended, as seen in FIG. 12. The gaps 380 between the ferromagnetic segments 375 may be adjusted such that the heating effect will be similar in the gaps 380 as the segments. Thus, the snare tool 370 with linear array may act similar to the snare with flexible coating in FIGS. 8 and 9.

Figure 13:
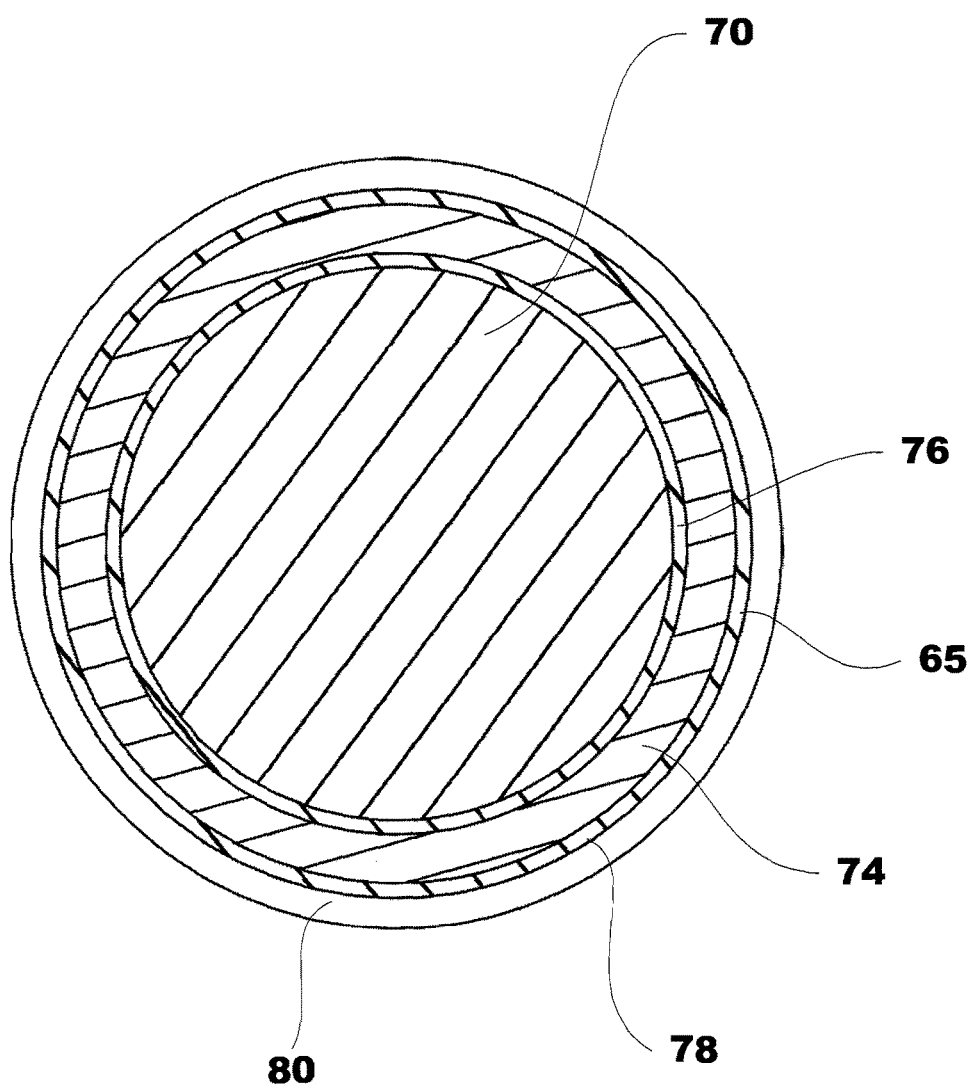
FIG. 13 shows an axial cross-sectional view of a single layer ferromagnetic coated conductor surgical tool in the ferromagnetic-coated region.

Turning now to FIG. 13, a cross-sectional view of a surgical tip in the ferromagnetic-portion is shown. The ferromagnetic portion 65 may be disposed circumferentially about a conductor 220. The surgical tip may be constructed of multiple layers. Each of the multiple layers may comprise a different material, or combinations of the same or different materials, so as to take advantage of the different properties of the various materials when used as a surgical tip. For example, the conductor 220 may include a support 70 which may be comprised of a material having high a Young's modulus, i.e. strength to resist bending. The conductor 220 may also include an the intervening layer 76, which may be a strike layer to facilitate attachment of additional layers, and an intervening layer 74, which may comprise one or more layers of copper, silver, or other material which is highly conductive. The ferromagnetic material 65, which may be a thin layer or coating 78 is then attached to the intervening layer 74 and a biocompatible material 80 may be disposed over substantially all or a portion of the length of the conductor 220.

Additionally, the ferromagnetic coating 78 of the ferromagnetic portion 65 may provide several advantages. First, the ferromagnetic coating 78 is less fragile when subjected to thermal stress than ferrite beads, which have a tendency to crack when heated and then immersed in liquid. The ferromagnetic coated conductor 60 has been observed to survive repeated liquid immersion without damage. Further, the ferromagnetic portion 65 has a quick heating and quick cooling quality. This is likely because of the small amount of ferromagnetic coating 78 that is acted upon by the magnetic field, such that the power is concentrated over a small area. The quick cooling is likely because of the small amount of thermal mass that is active during the heating. Also, the composition of the ferromagnetic coating 78 may be altered to achieve a different Curie temperature, which would provide a maximum self-limiting thermal ceiling attribute to the device.

Figure 14A:
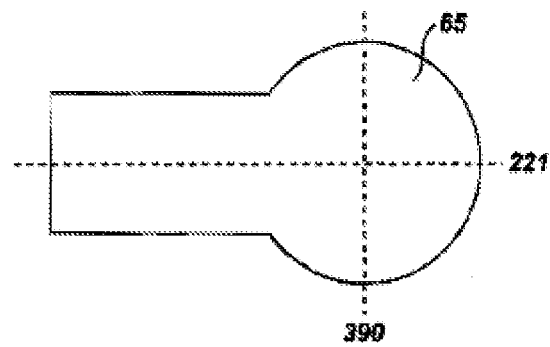
FIG. 14A shows a perspective view of a multi-layer ferromagnetic coated conductor surgical tool tip.
Figure 14B:
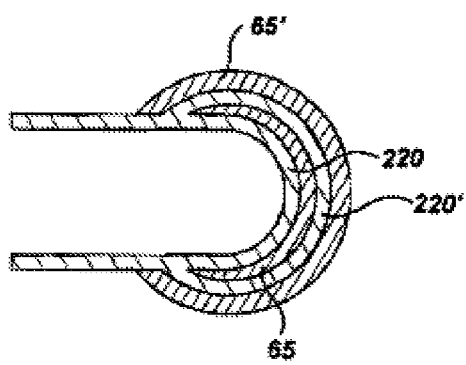
FIG. 14B shows a side cross-sectional view of a multi-layer ferromagnetic coated conductor surgical tool tip shown in 14A.
Figure 15:
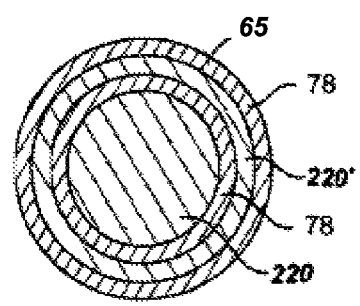
FIG. 15 shows an axial cross-section of the multi-layer ferromagnetic coated conductor surgical tool tip shown in FIG. 14A.

Turning now to FIGS. 14A, 14B and 15, a multilayer surgical tool tip is shown. A cross section of 14A along the 221 line may result in FIG. 14B which shows alternating layers of conductor 220 and 220' and ferromagnetic layers or coatings 78 at ferromagnetic portions 65 and 65'. Heating capacity may be increased by layering thin layers of alternating conductor material 220 and 220' and ferromagnetic coating 78 at portions 65 and 65', while still maintaining quick heating and cooling advantages. FIG. 15 shows an axial cross-sectional view from FIG. 14A along the 390 line (For clarity purposes, intervening layers and the biocompatible layer have been omitted from FIGS. 14A, 14B and 15). The alternating layers of conductor 220 and 220', and ferromagnetic coatings 78 and 78 may also be seen.

Figure 16:
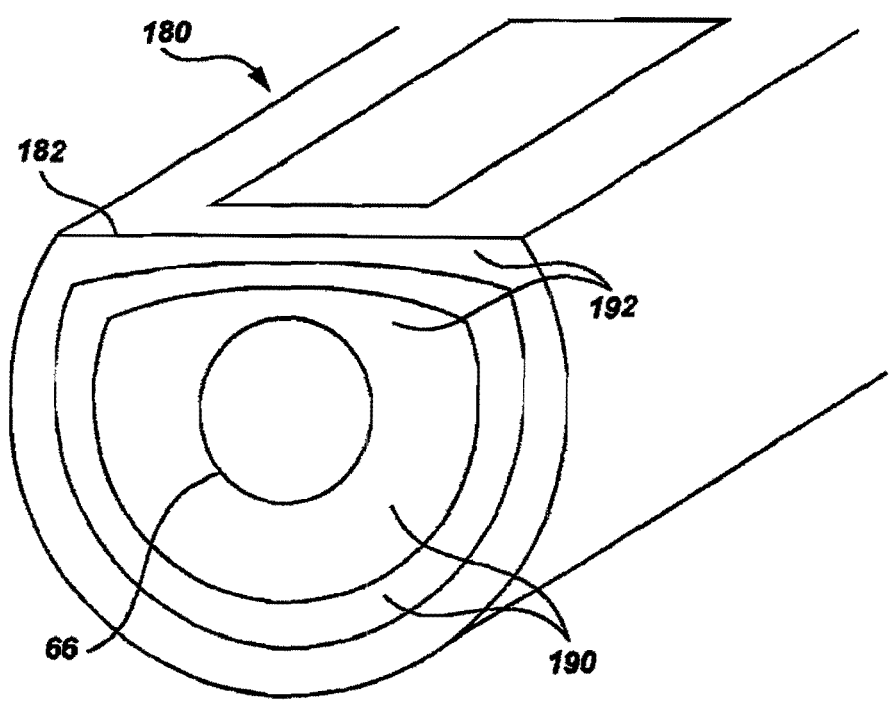
FIG. 16 shows a cross-sectional view of a flattened side cylindrical geometry ferromagnetic coated conductor showing electromagnetic lines of flux.

Turning now to FIG. 16, a flattened side cylindrical geometry is shown. The flat surface 180 can be manufactured to cause a thin plating 182 of ferromagnetic coating on the conductor 66 relative to the thicker plating around the rest of the conductor 66. This thin plating 182 may result in selective first onset heating in this flat surface 180. Inductive heating may be proportional to flux density within the magnetically permeable coating. In one embodiment, an asymmetrically thinned coating has a small cross sectional thickness and may generate higher hysteresis losses in the form of heat. Thus, a therapeutic temperature may be achieved with yet lower power at the flat surface 180 with higher flux density 192 compared to a cooler opposite side with a diminished flux density 190. An advantage is that fast temporal response and distributed optimal heating at the tissue interface may be enhanced.

Figure 17:
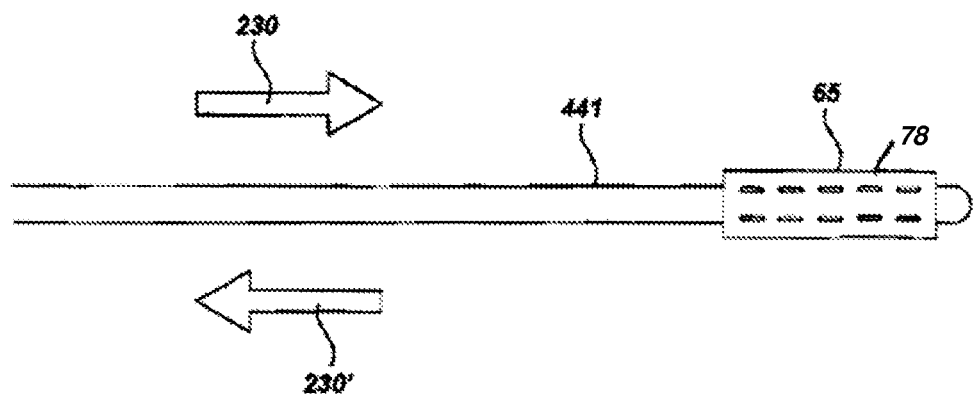
FIG. 17 shows a closed conductor tip in accordance with another aspect of the present invention.

Turning now to FIG. 17, the ferromagnetic portion 65 may also be configured to focus the temperature increase on the outside of the ferromagnetic layer or coating 78 of the ferromagnetic portion, further reducing the time needed to cool the ferromagnetic portion 65 in a relatively high power application. An example of such a configuration is shown in FIG. 17, wherein the fields generated by the current flow 230 and 230' (the arrows) may have a cancelling effect with respect to each other within the ferromagnetic layer or coating 78 surrounding both conductors, keeping the ferromagnetic material between the looped conductor 441 cooler than the ferromagnetic material at the perimeter.

Turning now to FIGS. 18A-18D, several surgical tip 194 geometries are demonstrated. In FIG. 18A, a surgical tip 194a with a single small diameter electrically conductive wire plated with the thin film magnetic material 196 is shown. In FIG. 18B, the surgical tip 194b with two small diameter electrically conductive wires plated with the thin film magnetic material 196' is shown. In FIG. 18C, a surgical tip 194c with three small diameter electrically conductive wires plated with the thin film magnetic material 196" are shown. It is thus contemplated that a tip geometry may consist of a plurality of small diameter electrically conductive wires plated with the thin film magnetic material. Such a design maintains the temporal heat responsiveness (rapid onset, rapid offset) essential to the dynamic surgical environment due to minimal mass of the ferromagnetic coated conductor. It is thus possible to configure a flat tine with two or more spaced wires as a practical monothermal or multi-thermal tool. Further, the tips 194a, 194b and 194c may also be exchangeable as seen in FIG. 18D, which has a receptacle 198 for the tips 194 in FIGS. 18A-18C. It will be appreciated that the generator system may be configured to adjust the power jointly delivered to two or more of the conductors and that a user control (as shown in other figures) can be provided for that purpose.

The ferromagnetic coating 78 can be used to contact the tissue directly, or, a non-stick coating, such as TEFLON (PTFE), or similar material, could be applied over the ferromagnetic coating and conductor around the ferromagnetic portion 65 to prevent sticking to the tissue. Alternatively, the ferromagnetic coating could be coated with another material, such as gold, to improve biocompatibility, and/or polished, to reduce drag force when drawing through tissue. The ferromagnetic coating could also be coated by a thermally-conductive material to improve heat transfer. In fact, a single coating may be selected to have multiple desirable properties.

Turning now to FIGS. 19 to 22, the ferromagnetic coated conductor may be attached to a primary geometry. The primary geometry may provide an attachment surface or an internal site for the conductor with a ferromagnetic coating. Thus the advantages of the ferromagnetic coating on a conductor may be combined with the advantages of the primary geometry and its corresponding material. The primary geometry may be selected for various reasons, including but not limited to, material strength, rigidity, heat conduction, resistance to thermal heat transfer, surface area, or additional functionality.

As used herein, a primary geometry means a structure to which a ferromagnetic coated conductor may be attached and which defines the shape of the tool. For example, a primary geometry could be a scalpel, tines of forceps, the face of a spatula, or a ball shape at the end of a probe. The conductor geometry, therefore, may be disposed upon the primary geometry, may extend through a hole in the primary geometry, and/or be embedded in the primary geometry. For example, a primary geometry may be a scalpel, while the conductor geometry may be the serpentine shape of a ferromagnetic coated wire upon the primary geometry.

Figure 19A:
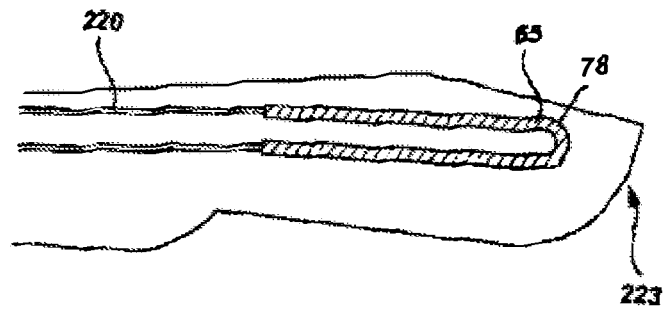
FIG. 19A shows a normally cold cutting scalpel with alternate ferromagnetic thermal function.
Figure 19B:
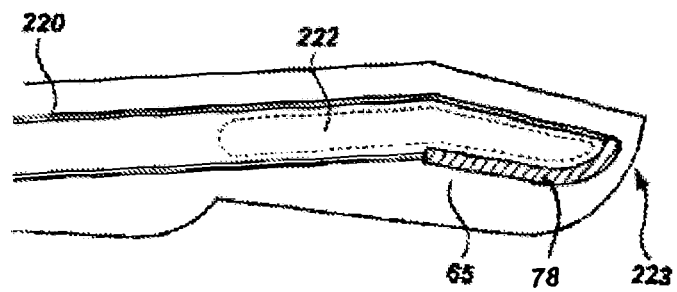
FIG. 19B shows a normally cold cutting scalpel with alternate ferromagnetic thermal function.

Turning now to FIGS. 19A and 19B, a cold cutting scalpel 223 with alternate inductive ferromagnetic thermal function is shown. The cold cutting scalpel 223 may be used for cutting through the application of a blade having a cutting edge and having a secondary thermal function activated when required, such as for coagulation. In the embodiments shown in FIGS. 19A and 19B, this is achieved by placing a ferromagnetic coated conductor 220 upon the side of a scalpel shaped primary geometry, which can cut tissue without activation of the conductor or ferromagnetic portion 65. The cold cutting scalpel 223 may be used classically to make incisions in tissue. However, if the patient begins to bleed, the cold cutting scalpel 223 operator may activate the ferromagnetic coated conductor and place the side of the cold cutting scalpel 223 (and correspondingly, the ferromagnetic coated conductor) upon the bleeding tissue. The thermal effect may then cause the tissue to seal and cease bleeding. After deactivation of the ferromagnetic coated conductor, the scalpel operator may then return to making incisions with the benefits of a cold cutting scalpel.

There are several advantages with using such a cold cutting scalpel 223. The dual-use tool does not require the cold cutting scalpel 223 operator to remove one tool and replace it with another, causing risk of further damage and delay. Due to the ferromagnetic coating 78, the cold cutting scalpel 223 may also have a quick thermal response time (the heat-up and cool-down time) in the ferromagnetic portion 65 such that the cold cutting scalpel 223 may be used on the targeted area and reduce waiting time. In cases where it may be desirable to heat the entire cold cutting scalpel, thermal response time may be further reduced by removing a center portion 222 of the blade (as seen in FIG. 19B), resulting in a non-contiguous portion of the blade that may occur between or adjacent to the conductor path. Removing the center portion 222 of the blade may further reduce the thermal mass and correspondingly the thermal response time.

In one embodiment, related to FIG. 19B, the ferromagnetic coating may be limited to a defined part or parts of the scalpel, such as the tip of the cold cutting scalpel 223. This limiting would cause only the tip to heat, while the remaining portions of the primary geometry would remain at a lower temperature. This limiting of the heating to a portion of the primary geometry in proximity to the ferromagnetic coating may provide a higher degree of accuracy and usefulness in smaller spaces. Similarly, the ferromagnetic coated conductor 220 may form a pattern, such as a zigzag or serpentine pattern, across the surface of the cold cutting scalpel 223 to increase the heating coverage of the surface.

Scalpel effects may also be enhanced by the thermal effects of the ferromagnetic coated conductor 220. In one embodiment, the scalpel may have multiple parts with different temperature ranges addressable to each part. For example, energy to the scalpel blade may be used to cut, while energy to the sides of the blade may be used to coagulate tissue walls. In another embodiment, the ferromagnetic coated conductor 220 may be activated to provide additional cutting ability when moving through more difficult tissue. In another embodiment, the ferromagnetic coated conductor may be activated to provide a more smooth cutting process in conjunction with the scalpel blade. A user control may be used to select a power setting to be delivered by a power source, which may be correlated with a desired temperature or tissue effect.

Turning now to FIG. 20A, a thermal surgical tool with a spatula shaped geometry is shown. The spatula 224 may have a ferromagnetic portion 65 with a ferromagnetic coating 78 on a conductor 220 (or intervening layer forming part of the conductor) that follows the perimeter of the spatula shape as shown. In an alternate embodiment, the ferromagnetic coated portion of the conductor 220 may form a pattern across the surface of the geometry such that the surface is more evenly covered by the ferromagnetic portion 65 of the conductor 220.

A spatula geometry may be useful for various tissue effects and procedures. In one embodiment, the spatula is used for hemostasis or tissue welding during surgery. After an incision has been made, if needed, the spatula may be applied to the incised tissue to achieve hemostasis or even tissue welding. In another embodiment, the spatula pressed into tissue and thermal energy is used for tissue ablation.

Turning now to FIG. 20B, the thermal surgical tool with a spatula shaped geometry is shown in forceps form. The spatula forceps 225 may be used in combination such that each spatula has a separate power control or the forceps may have a power control in common. Such a tool can be used to clamp vessels to stop blood flow, and then cause hemostasis and cutting of the vessels with heat.

Turning now to FIGS. 20C and 20D, a side view of FIG. 20A is shown in two different embodiments. The ferromagnetic coating and conductor may be attached to the primary geometry in several ways. In one embodiment shown in 20C, the ferromagnetic coating 78 and conductor may be attached to the surface of the primary geometry. Alternatively in 20D, the ferromagnetic portion 65 and conductor may be embedded within the primary geometry. Depending upon the desired effect, the tools depicted in FIGS. 20A, 20B, 20C and 20D can be applied to tissue in such a manner that the side of the tool on which the ferromagnetic coated conductor 65 is located can contact the tissue, or the opposite side can be applied to the tissue.

Figure 20E:
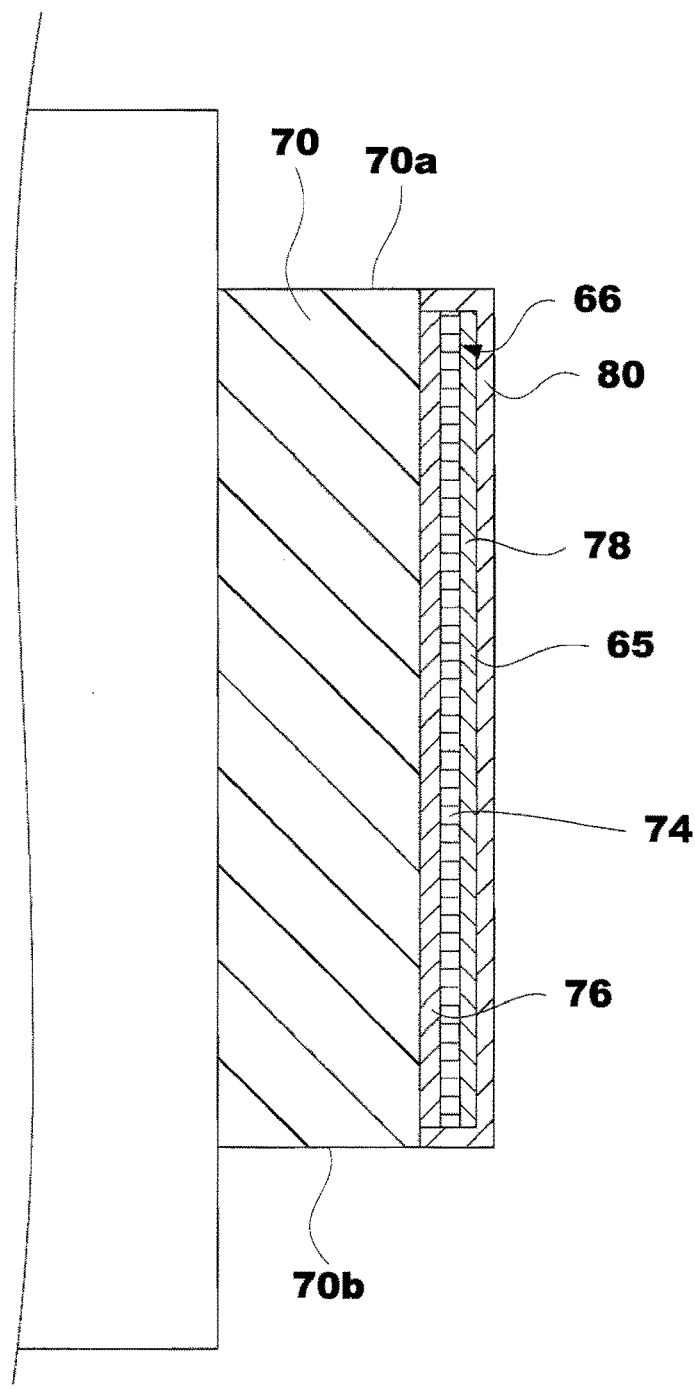
FIG. 20E shows a close-up, side cross-sectional view of a thermal surgical tool with a ferromagnetic coated conductor disposed thereon.
Figure 20F:
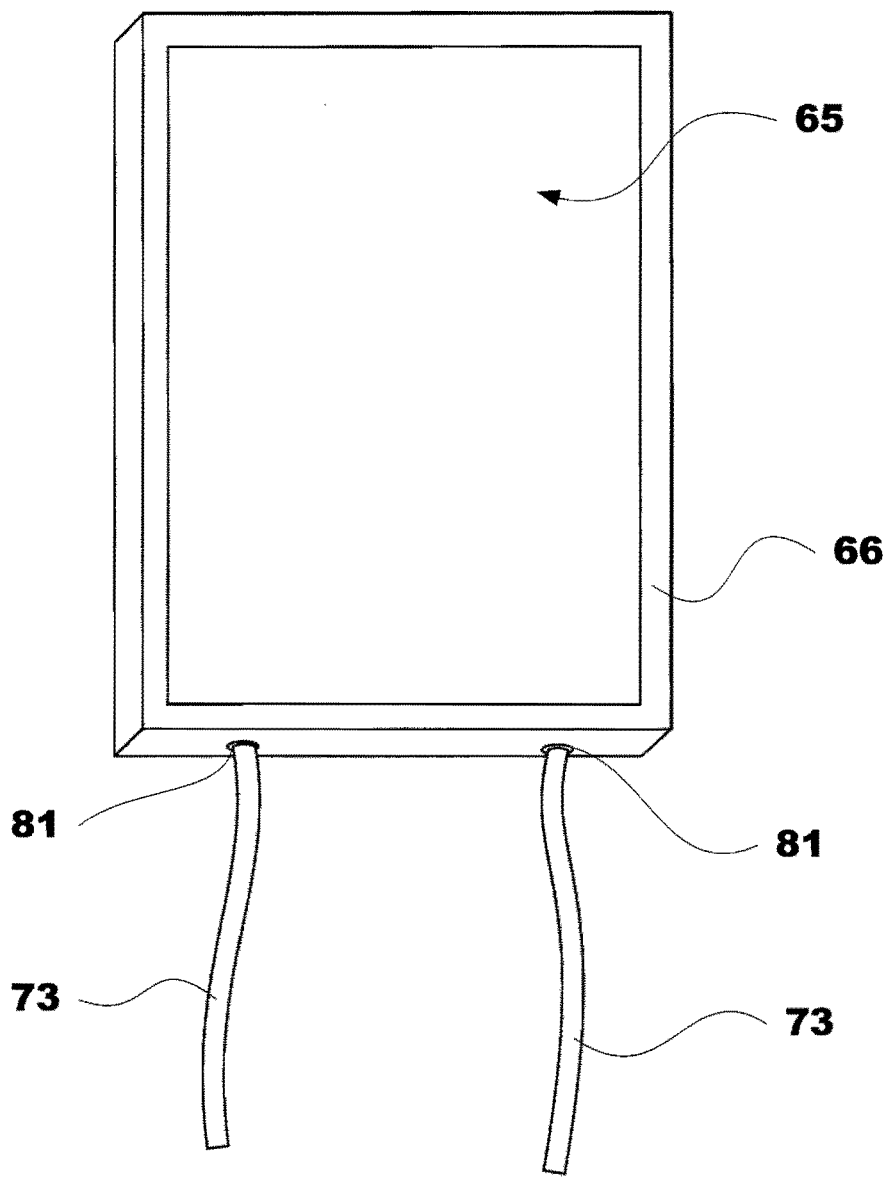
FIG. 20F shows a perspective view of a heating element of the present invention that may be disposed on a primary geometry.

Turning now to FIGS. 20E and 20F, a close-up, side cross-section view of a thermal heating element comprising a ferromagnetic coated conductor is shown in FIG. 20E. The heating element may be formed on or attached to a surgical tool, such as the configurations shown in FIGS. 20C and 20D, or a variety of other tools discussed herein.

As described above, a ferromagnetic heating element 227 may comprise multiple layers of different materials. The material comprising each of the layers may be selected to enhance construction and/or provide a desired property to ensure efficient operation of the heating element.

The heating element may include a support 70 to provide rigidity to the heating element. However, the need to select a material having a high resistance to bending for support 70 may be diminished because the heating element is attached to the primary geometry, which also tends to support the other layers of the heating element. Attached to the support 70 may be one or more intervening layers 74, 76. The intervening layer 76 may be a strike layer for enhancing the ability of outer layers of the heating element to attach to the support 70. The intervening layer 74 may comprise a highly conductive material through which a majority of the electrical current that is applied to the heating element passes. A ferromagnetic portion 65, such as a thin layer or coating 78 of ferromagnetic material, may be attached to one of the intervening layers 74 or 76. A biocompatible layer 80 may cover all or a portion of the heating element including the ferromagnetic layer or coating 78, which is attached to the intervening layer 74. The biocompatible layer 80 may prevent oxidation of the underlying layers of the heating element and also substantially prevent biological materials from sticking to the surface of the heating element when in use. The biocompatible layer 80 may also extend along the surfaces 70a, 70b of the support to prevent oxidation at the surfaces 70a, 70b and provide a lubricant-like property to those surfaces. FIG. 20F shows a perspective view of a heating element of the present invention that may be disposed on a primary geometry. The heating element may be constructed similarly to the heating element disposed on the primary geometry shown in FIG. 20E. The electrical conductor 66 may include connection site(s) 81 for connecting to an electrical power source independent the ferromagnetic portion 65. The conductor 66 may be connectable to the power source via leads 73. When the heating element is actuated, electrical current may pass through the conductor 66 and cause the ferromagnetic portion 65 to inductively heat. The heating element may be disposed on a variety of primary geometries so as to allow a surgeon to provide a thermal therapeutic effect to tissue during a procedure. Although the heating element is shown as generally rectangular in shape, it will be appreciated that the shape of the heating element may be constructed in a variety of shapes. For example, the heating element may be constructed so as to conform to the contours of a primary geometry such as a scalpel or forceps having a pointed end.

Figure 21A:
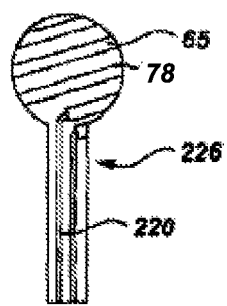
FIG. 21A shows a thermal surgical tool with a ball shaped geometry and horizontal winding.
Figure 21B:
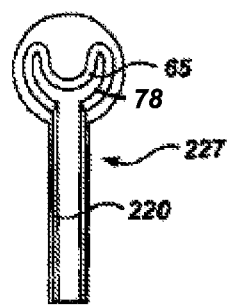
FIG. 21B shows an alternate embodiment of a thermal surgical tool with a ball shaped geometry and horseshoe configuration.
Figure 21C:
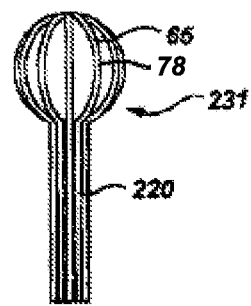
FIG. 21C shows an alternate embodiment of a thermal surgical tool with a ball shaped geometry and vertical orientation.

Turning now to FIGS. 21A, 21B and 21C, a thermal surgical tool with a ball shaped geometry is shown. In one embodiment, a horizontally wrapped ball 226 or a vertically wrapped ball 231 may be internally or externally wrapped with a conductor 220 with a ferromagnetic portion 65 having a ferromagnetic coating 78 as seen in FIG. 21A and FIG. 21C. In another embodiment, shown in FIG. 21B, a ball geometry 227 may contain a conductor 220 with a ferromagnetic coating prepared in another shape, such as a horseshoe shape. In the embodiments, a ball-shaped heating element may be formed which can be used to coagulate or provide a therapeutic effect over a large surface area of tissue. The ball may also be effective in tissue ablation, as it may radiate thermal energy in most, if not all, directions.

Figure 22A:
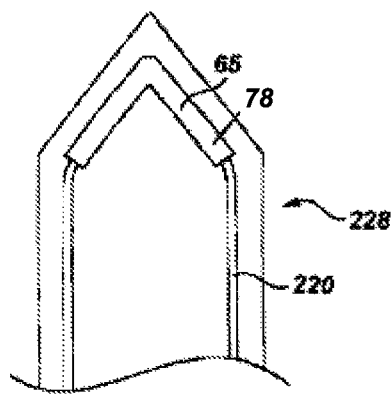
FIG. 22A shows a thermal surgical tool with a pointed geometry.

Turning now to FIG. 22A, a thermal surgical tool with a pointed geometry is shown. The pointed tool 228 may have a ferromagnetic portion 65 with a ferromagnetic coating or layer 78 on a conductor 220 that follows the perimeter of the pointed tool shape as shown. In an alternate embodiment, the ferromagnetic coated portion of the conductor 220 may form a pattern across the point surface of the geometry such that the point surface is more evenly covered by the ferromagnetic coated portion of the conductor 220. The pointed tool 228 may be particularly useful for making incisions that penetrate layers of tissue, providing a means for coagulation while cutting, such as coagulation of tissue around the site of trocar insertion for laparoscopic surgery.

Figure 22B:
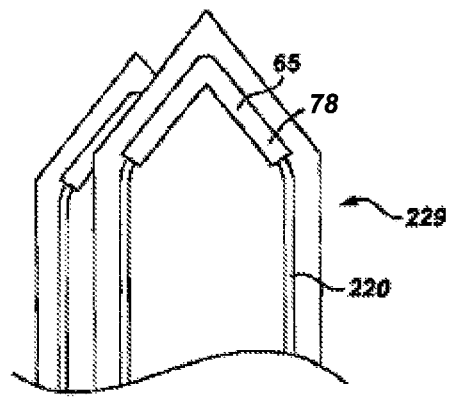
FIG. 22B shows a thermal surgical tool with a pointed geometry in a forceps configuration.

Turning now to FIG. 22B, the thermal surgical tool with a pointed geometry is shown in forceps form. The pointed forceps 229 may be used in combination such that each pointed geometry has a separate power control or the forceps may have a power control in common. Such a tool can be configured for achieving hemostasis and cutting in small vessel ligation.

While some primary geometries have been shown in singular form, the primary geometries may be used in combination. This may include two or more of the same primary geometry or differing primary geometries, including forceps applications. Each primary geometry may be commonly controlled for power or have separate power controls for each primary geometry. Furthermore, solid primary geometries may be altered similar to the scalpel primary geometry shown above such that portions of the primary geometries may be removed to reduce thermal mass and correspondingly, thermal response time.

While some of the primary geometries have been shown to have symmetrical construction, the primary geometries may have asymmetrical or directional construction such that only a portion of the primary geometry would be active. This may be accomplished by placing the ferromagnetic coating only on the portion of conductor wire residing on the area of the primary geometry desired to be active. For example, the spatula geometry may be configured to be active in one area if the ferromagnetic coated conductor is not symmetrically positioned on the spatula structure. This may be further enhanced by providing a pattern, such as a zigzag or serpentine pattern, on the desired active portion of the geometry.

Figure 22C:
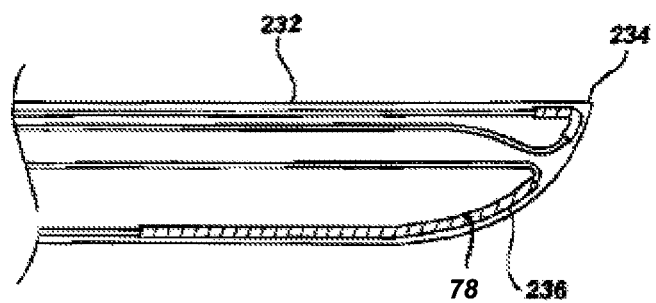
FIG. 22C shows a thermal surgical tool having two different activatable thermal zones.

In another embodiment, a portion of the primary geometry may be activated. By using multiple conductors with a ferromagnetic portion 65 having a ferromagnetic coating or layer attached to different portions of a primary geometry, a portion of the primary geometry may be selectively activated. For example, a scalpel geometry 232 may be divided into a tip portion 234 and a face portion 236 as shown in FIG. 22C. A scalpel operator may then choose whether to activate only the tip or the tip in conjunction with the face of the scalpel geometry, depending on the surface area desired. Similarly, in a forceps application, the forceps may be divided into inside and outside portions. If the forceps operator desires to remove something that may be surrounded by the forceps, such as a polyp, the internal portions may be activated while the external portions remain deactivated. If opposing sides of a void need to be sealed, the outside surfaces of the forceps may be activated.

By using multiple conductors with a ferromagnetic coating 78 attached to different portions of a primary geometry and separately controlled power sources, different portions of the primary geometry may be activated at the same time for different uses or effects. For example, an edge portion of a primary geometry may be activated for cutting while the blade portion may be activated for hemostasis.

A method of treating tissue may thus include the steps of: selecting a primary geometry having a conductor disposed thereon, the conductor having a ferromagnetic coating disposed on a portion thereof; disposing the ferromagnetic coating into contact with the tissue; and delivering an oscillating electrical signal to the conductor so as to heat the ferromagnetic coating and treat the tissue.

Optional steps of the method may include choosing a primary geometry selected from the group of scalpel, spatula, ball and pointed geometry. Treating of the tissue may include incising, causing hemostasis, ablating or vascular endothelial welding.

A method for tissue destruction may include the steps of selecting a conductor having a ferromagnetic coating disposed on a portion thereof; and delivering an oscillating electrical signal to the conductor so as to heat the ferromagnetic coating and destroy tissue.

Optional steps of the method may include monitoring the tissue and ceasing delivery of the oscillating electrical signal to the conductor when the desired tissue destruction has occurred or undesired tissue effects are to be prevented.

A method for forming a surgical instrument may include the steps of: selecting a primary geometry; coating a conductor with ferromagnetic material; and disposing the conductor on the primary geometry.

Optional steps of the method may include providing electrical connections on the conductor configured for receiving oscillating electrical energy.

Figure 23A:
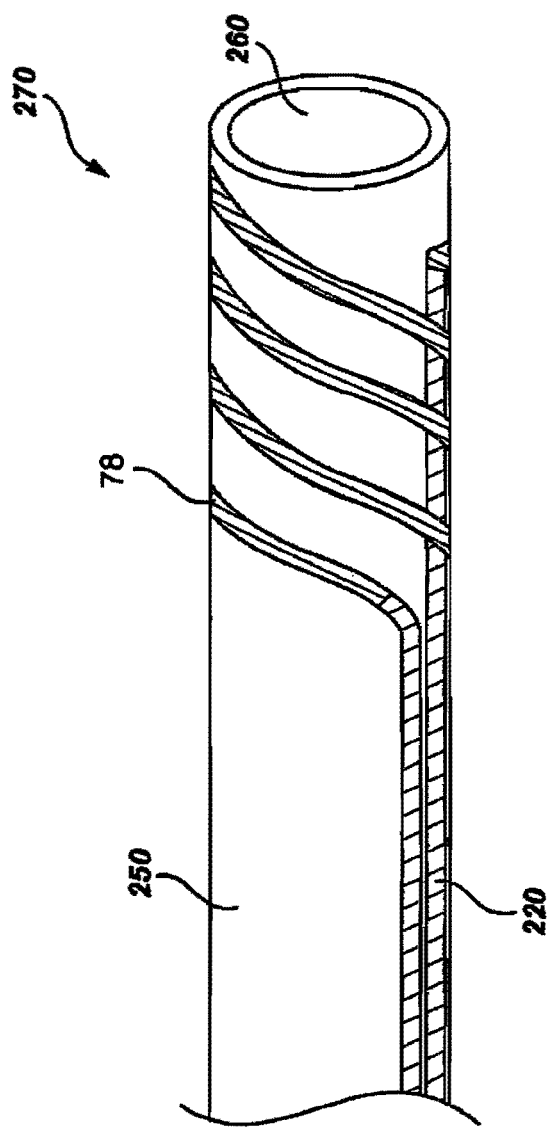
FIG. 23A shows a perspective view of a catheter having a coil of ferromagnetic coated conductor disposed around the tip of the catheter.

Turning now to FIG. 23A, a catheter 270 having a conductor 220 which is at least partially coated with ferromagnetic material disposed around the tip of the catheter is shown. Depending upon the therapeutic effect desired, the location of the coil of ferromagnetic coating 78 could instead be inside the catheter tip, or a single loop of ferromagnetic coated conductor having a circumference which approximates that of the catheter central channel 260 could be located at the end of the catheter tip.

Figure 23B:
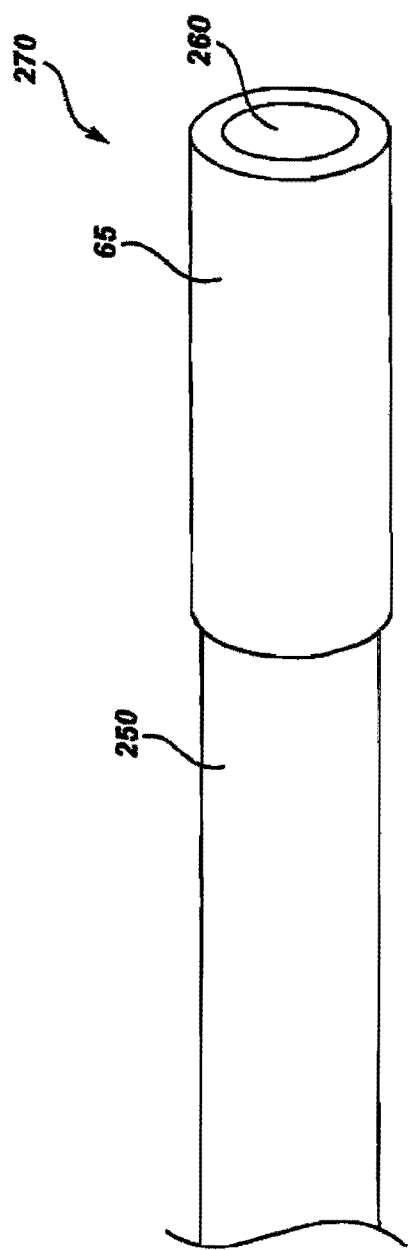
FIG. 23B shows a perspective view of an ferromagnetic coated conductor surgical tool catheter tip.

In FIG. 23B, another ferromagnetic coated catheter 270 is shown. While in some embodiments the conductor may be a wire, coil, or annular structure, a ferromagnetic coated catheter 270 could also be formed which would serve as an alternate conductor 250 with a ferromagnetic portion 65. In this embodiment, the catheter could consist of two coaxial conductors, separated by an insulator. At the distal tip of the catheter 270, a conductive coating can be applied such that a continuous electrical path is created by the coaxial conductors. The ferromagnetic coating can be dispersed about the external diameter surface near the distal tip of the catheter, as shown in FIG. 23B, or, upon the end of the catheter, on the annular surface connecting the coaxial conductors. This would allow the ferromagnetic coated catheter 270 to perform other functions, such as irrigation, aspiration, sensing, or, to allow viewing access via optical fibers, through a central channel 260, as is common in many interventional as well as open and minimally invasive surgical procedures. Furthermore, the central lumen of the catheter could be used to provide access to other sensing modalities, including, but not limited to, impedance and pH.

While not discussed in detail with each FIG. for brevity, it will be appreciated that any of the configurations discussed herein may use a conductor which may be formed with a support and/or which may include intervening layers to promote attachment and/or serve as a conductive layer. Likewise a covering of biocompatible or other material could be used over the ferromagnetic portion as discussed in detail with respect to FIGS. 1A-1D, 4C-4D, etc.

Figure 24:
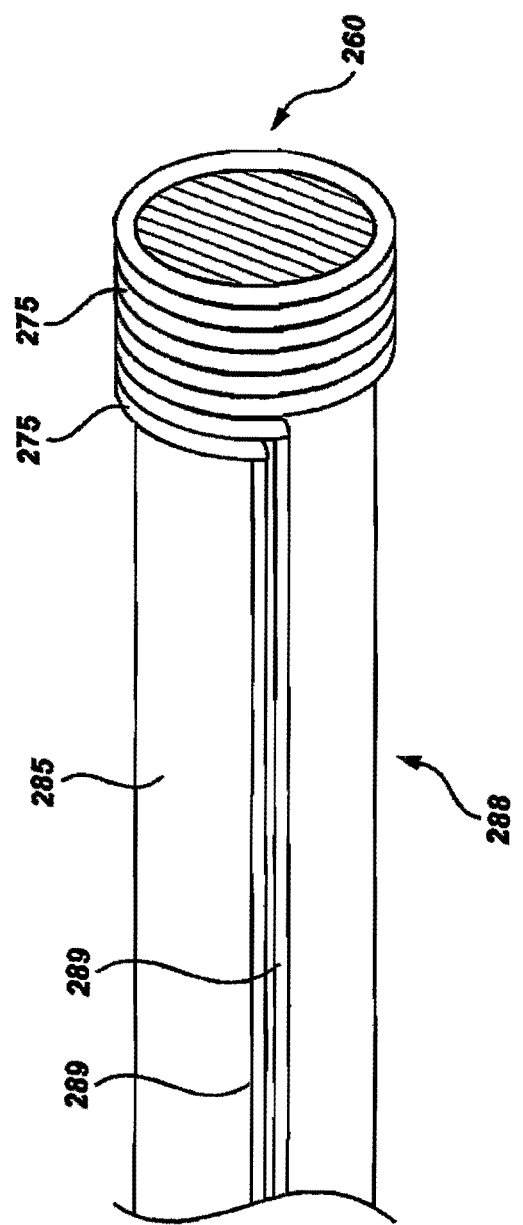
FIG. 24 shows a side view of an alternate embodiment of an ferromagnetic coated conductor surgical tool catheter tip.

Turning now to FIG. 24, a side view of an alternate embodiment of a ferromagnetic coated conductor surgical tool catheter tip 288 is shown. In one embodiment, the conductor may consist of a ferromagnetic coated conductor positioned on a substrate 285 forming a body with a central channel. The ferromagnetic coating may consist of a plated ferromagnetic coating 275 on top of a conductor 289. The conductor 289 may be comprised of one or more intervening layers and/or a biocompatible layer. The conductor 289 may be placed on the outside of the substrate 285 such that the thermal effects are directed externally. This may allow the catheter tip to apply thermal tissue effects to tissue walls.

In another embodiment, the inside of the substrate may contain the conductor 289 and ferromagnetic layer or coating 275 such that the thermal effects are directed internally. An internal coating may allow delivery of a meltable solid to a desired area, such as in fallopian tube sealing and osteosynthesis applications.

Alternatively, the ferromagnetic layer or coating 275 may surround the entrance to the central channel 260, such that the thermal effects may be directed in front of the tip. Having the thermal energy be directed in front of the central channel 260 entrance may aid in taking a tissue sample or removal of material, such as a polyp.

The plating may be accomplished through multiple methods. The substrate 285 may be extruded, molded or formed from various materials including high temperature thermoplastic, glass, or other suitable substrate material. The actual plating may be accomplished through electroplating, electroless plating, vapor deposition, or etching, or some combination thereof. Thus through the plating process, a catheter tip 288 may be formed with a ferromagnetic layer or coating 275 on a conductor 280 with a continuous path.

The catheter may also have multiple channels. One channel may be a deployment channel for the ferromagnetic coated conductor. Another channel may be used for one or more sensors or sources, or even each sensor or source in its own channel—such as a temperature sensor, illumination source and endoscope. Other channels may include delivery, irrigation or aspiration of substances, including those associated with treatment, such as in osteosynthesis or fallopian tube sealing. In fact, the ferromagnetic coating may aid in the melting of such substances.

Figure 25:
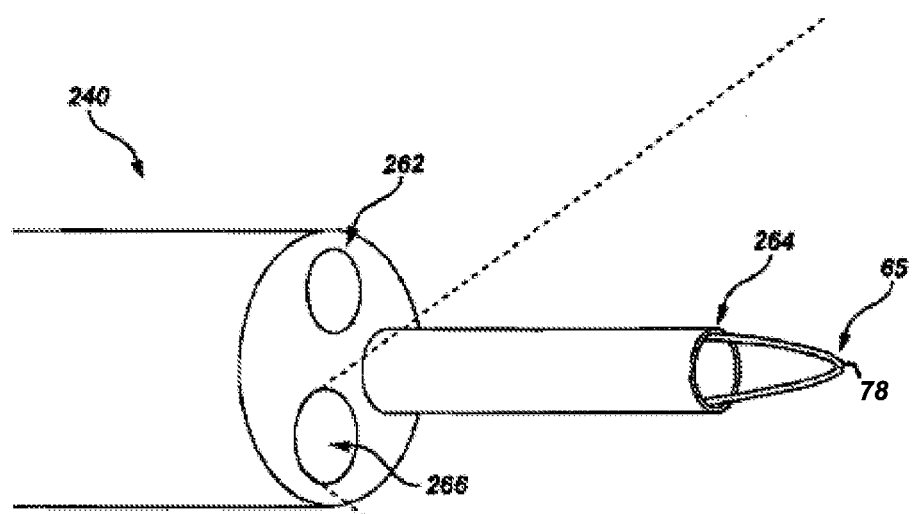
FIG. 25 shows an alternate embodiment of a ferromagnetic coated conductor surgical tool ferromagnetic tip disposed within an endoscope.

Turning now to FIG. 25, an endoscope 240 with a viewing channel 262 of rod lens type or organized fiber bundle type aside a light emitting source 266 is shown. A loop coagulator/cutter 264 is shown which consists of the ferromagnetic coated conductor 65. Such an adaptation is contemplated in snare applications such as colon polypectomy or sealing and cutting applications in various laparoscopic procedures. Other sensing modalities include near field tumor cell detection or infrared heat monitoring. Tool configurations similar to the described endoscope 240 can be embodied in tools that can be delivered to target tissue through the lumen of a catheter.

In one embodiment, tumor cells are caused to be tagged with materials that fluoresce when exposed to ultra-violet light. The endoscope 240 may contain a light source 266, and sensor or optics within the channel 262 that return the detected florescence. The ferromagnetic portion 65 portion of the endoscope 240 may then be directed at the tagged tissue for destruction.

In another embodiment, materials are deposited around target tissue or bone in a solidified condition. Once delivered, the materials are melted to conformation at the site by activation by the endoscope 240 described above. Examples of use of this embodiment include fallopian tube sealing and osteosynthesis. Furthermore, such materials could be removed by melting with the same or similar endoscope 240, and aspirated through a central lumen of the endoscope 240. In yet further applications, materials may be delivered in liquid form, and cured by a thermal heating process induced by the endoscope 240.

Alternatively, the conductor may be part of a bundle of fibers. The fibers may be contained within a catheter or otherwise bundled together. The conductor may have a ferromagnetic coating, while the other fibers may have other purposes that include visual observation, sensing, aspiration, or irrigation.

A method of tissue ablation may include the steps of: selecting a catheter with a ferromagnetic covered conductor; causing the ferromagnetic covered conductor to touch tissue to be ablated; and delivering power to the ferromagnetic covered conductor.

Optional steps may include: directing the catheter to the tissue through the aid of an endoscope; selecting a ferromagnetic coated conductor disposed on the catheter; selecting a ferromagnetic coated conductor contained within the catheter; causing the ferromagnetic coated conductor to be deployed from the catheter; or touching the ferromagnetic coated conductor to the tissue to be ablated.

A method of delivering a substance into a body may include the steps of: selecting a catheter with a ferromagnetic coated conductor; placing a substance in the catheter; inserting the catheter into a body; and causing power to be sent to the ferromagnetic coated conductor.

Optional steps may include: selecting a substance for osteosynthesis; selecting a substance for fallopian tube sealing; or melting the substance in the catheter.

A method of treating tissue may include the steps of: selecting a catheter with a ferromagnetic coated conductor; placing the catheter in contact with tissue; and selecting a power setting. The temperature range may correspond to a temperature range or desired tissue effect. The desired tissue effect may be selected from the group of vascular endothelial welding, hemostasis, searing, sealing, incision, ablation, or vaporization. In fact, the power setting may correspond to a desired tissue effect.

Figure 26:
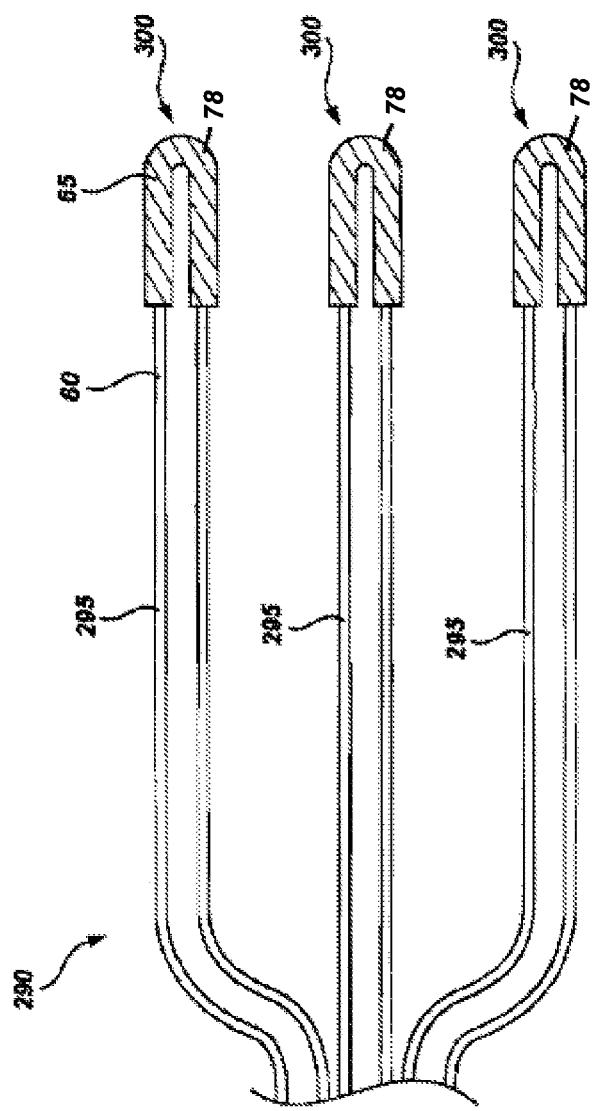
FIG. 26 shows a tissue ablation tool.

Turning now to FIG. 26, a tissue ablation tool 290 is shown. In typical applications of tissue ablation, an arm or tine 295 is inserted into undesired tissue. One or more tips 300 may be activated such that the tissue temperature is raised to a desired level for a desired amount of time. After the activation has succeed in holding a temperature for a desired amount of time, or undesired effects are noticed, the one or more tips 300 may be deactivated and removed from the tissue.

In one embodiment, a conductor may be contained in one or more arms or tines 295 with tips 300 that may contain ferromagnetic coatings 65. The tips 300 may be inserted into tissue and temperature controlled until tissue destruction occurs or one or more undesired tissue effects occur. The tissue effects may be monitored through sensors in the tines 295 or externally.

Sensors may be placed in multiple ways. In one embodiment, the sensor is placed in the tine and away from a ferromagnetic coated tip 300. In another embodiment, one tip 300 may have a ferromagnetic coating, while an alternate tip 300 may have no coating, but a sensor contained within.

The sensors may monitor tissue effects or return signals to be observed or processed. This may include sensors such as temperature sensors, cameras and remote imaging. In another embodiment, the temperature may be monitored through external imaging.

The sensor may thus form part of a feedback loop. By monitoring one or more tissue effects, the ablation tool may self-adjust power settings. This self-adjustment may allow the system to operate below the Curie point and still maintain a desired tissue effect and/or temperature range.

In the case where more than one tip 300 is used, the tips 300 with a ferromagnetic portion 65 having a ferromagnetic layer or coating 78 may be individually controlled such that the thermal profile is concentrated in the desired area. This may also allow a second tine to monitor tissue effects, while a primary tine is used to perform the thermal function.

While a diagram has been shown of a multi-tip tissue ablation tool in FIG. 26, a single tissue ablation tool may be made in a configuration similar to FIG. 7C.

Besides the advantages of uses in tissue, the surgical tool may also be self-cleaning. In one embodiment, when activated in air, the tool may achieve a temperature sufficient to carbonize or vaporize tissue debris.

Figure 27:
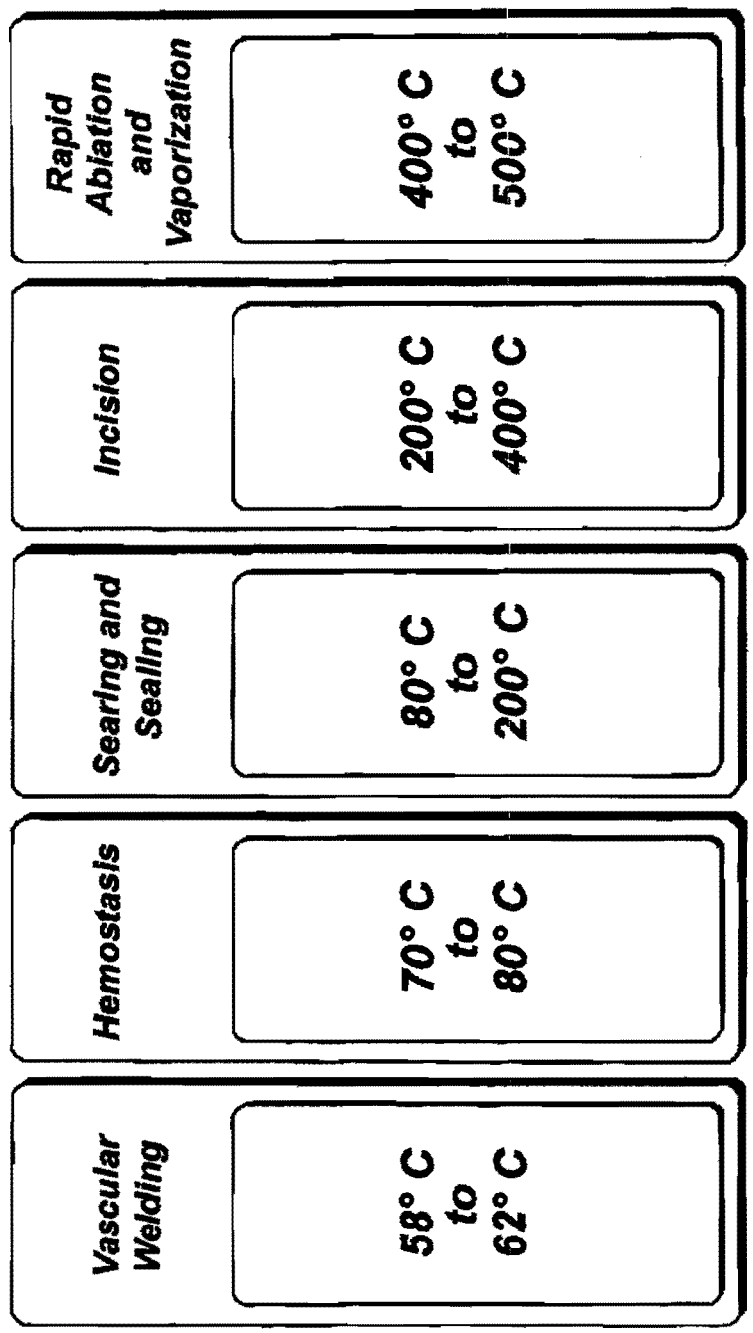
FIG. 27 shows a thermal spectrum as related to tissue effects.

Turning now to FIG. 27, a temperature spectrum is disclosed. Tissue may react differently at different temperatures with a tissue treatment element (such as a ferromagnetic coated conductor) and thus temperature ranges will result in different treatments for tissue. Specific tissue treatments are somewhat variable due to inconsistencies including tissue type and patient differences. The following temperatures have been found to be useful. Vascular endothelial welding may be optimal at 58-62 degrees Centigrade. Tissue hemostasis without sticking may be achieved at 70-80 degrees Centigrade. At higher temperatures, tissue searing and sealing may occur more quickly, but coagulum may build-up on the instrument. Tissue incision may be achieved at 200 degrees Centigrade with some drag due to tissue adhesion at the edges. Tissue ablation and vaporization may occur rapidly in the 400-500 degree Centigrade range. Thus, by controlling the temperature the "treatment" of tissue which the device delivers can be controlled, be it vascular endothelial welding, tissue incision, hemostasis or tissue ablation.

Besides the advantages of uses in tissue, the surgical tool may also be self-cleaning. In one embodiment, when activated in air, the tool may achieve a temperature sufficient to carbonize or vaporize tissue debris.

According to the spectrum disclosed above, power delivery settings corresponding to the desired temperature range may be included in the power delivery switch. In one embodiment, the foot pedal may have several stops that indicate to the surgeon the likely tip temperature range of the current setting.

It will be appreciated that the thermal surgical tool system in accordance with the present invention will have a wide variety of uses. Not only can it be used on humans, it can also be use to cut tissue of other animals, such as in the context of a veterinarian or simply cutting tissues or biomaterials, such as those used for implantation, into smaller pieces for other uses.

Certain embodiments of the surgical system may have broad application within surgery as well. A loop geometry may have advantages in cutting, coagulation and biopsy applications. A blade geometry may have advantages for cutting and hemostasis applications. The point geometry may have advantages in dissection and coagulation applications, and in particular, neurodissection and coagulation. However, the application of a geometry may be further configured and tailored to an application by diameter, length, material characteristics and other characteristics discussed above.

While the present invention has been described principally in the area of surgical tools and the treatment of live tissue (though it can be used on dead tissue as well), it will be understood that a tool made in accordance with the present invention and the methods discussed herein may have other uses. For example, a cutting tool could be formed for butchering meat. Whether the meat is fresh or frozen, the tool can be useful. For example, a cutting blade which is heated to a high temperature will cut through frozen meat. However, when power is no longer supplied, the "cutting" edge is safe to the touch. Likewise, cutting meat with a hemostasis setting would slightly sear the exterior of the meat, locking in juices. Other uses of the instruments discussed herein will be understood by those skilled in the art in light of the present description.

There is thus disclosed an improved thermally adjustable surgical tool. It will be appreciated that numerous changes may be made to the present invention without departing from the scope of the claims.

We claim:

1. A method for manufacturing a thermal surgical tool comprising:
   forming an electrical conductor by attaching an electrically conductive intervening layer to a metallic support; and
   coating the electrical conductor with a ferromagnetic material by electroplating;
   wherein the intervening layer is disposed between the metallic support and the ferromagnetic coating.

2. The method according to claim 1, further comprising providing the electrical conductor with connection sites for connecting the electrical conductor to a power source independent of the ferromagnetic material.

3. The method according to claim 1, further comprising disposing an exterior layer over the ferromagnetic material and at least a portion of the electrical conductor.

4. The method according to claim 1, comprising:
   disposing a second intervening layer between the metallic support and the electrically conductive intervening layer, wherein the second intervening layer comprises a strike layer that extends substantially a full length of the metallic support.

5. The method of claim 4 wherein attaching the electrically conductive intervening layer to the metallic support includes electroplating the electrically conductive intervening layer to the metallic support.

6. The method of claim 5 wherein the strike layer includes at least one of nickel or gold.

7. The method according to claim 1, wherein the metallic support is at least partially hollow.

8. The method according to claim 7, wherein the metallic support has a coefficient of thermal expansion which is less than a coefficient of thermal expansion of the ferromagnetic material, and a coefficient of thermal expansion of the intervening layer is greater than the coefficient of thermal expansion of the support and less than the coefficient of thermal expansion of the ferromagnetic material.

9. The method according to claim 1, wherein the ferromagnetic material extends a length along the metallic support, the length of the ferromagnetic material being less than about 90 percent of a length of the metallic support.

10. The method according to claim 1, comprising:
disposing a first sleeve on a first end of the metallic support; and
disposing a second sleeve on a second end of the metallic support, the first sleeve and the second sleeve being in electrical communication with the electrically conductive intervening layer.

11. The method according to claim 1, wherein the metallic support has a diameter within a range of 500 μm to 750 μm, the electrically conductive intervening layer has a thickness within a range of 20 μm to 50 μm, and the ferromagnetic material has a thickness within a range of 2 μm to 10 μm.

12. The method according to claim 1, wherein the metallic support has a Young's modulus in excess of 17 psi.

13. The method according to claim 1, wherein the metallic support has a Young's modulus greater than about 58 psi.

14. The method of claim 1 wherein the metallic support comprises at least one of tungsten, titanium, stainless steel, or an alloy thereof.

15. The method of claim 1, comprising:
electrically connecting a first end of the electrical conductor to a printed circuit board at a first position; and
electrically connecting a second end of the electrical conductor to the printed circuit board at a second position.

16. A method of treating tissue comprising:
selecting a thermal surgical tool comprising a conductor having a metallic support and an electrically conductive intervening layer on the metallic support, the thermal surgical tool further including a coating of a ferromagnetic material electroplated on the conductor, wherein the conductor is connectable to an electric power source independent of the ferromagnetic material;
disposing the ferromagnetic material adjacent to the tissue;
treating the tissue by directing oscillating electrical energy through the conductor to cause the ferromagnetic material to inductively heat;
wherein the electrically conductive intervening layer is disposed between the metallic support and the ferromagnetic material.

17. The method according to claim 2, comprising:
electrically connecting the electric power source to the electrical conductor; and
supplying the oscillating electrical energy to the conductor.

18. The method according to claim 17, wherein a majority of the oscillating electrical energy passes through the electrically conductive intervening layer.

* * * * *